(12) United States Patent
Brittain et al.

(10) Patent No.: US 9,572,785 B2
(45) Date of Patent: *Feb. 21, 2017

(54) DP2 ANTAGONIST AND USES THEREOF

(71) Applicant: Brickell Biotech, Inc., Miami, FL (US)

(72) Inventors: Jason Edward Brittain, El Cajon, CA (US); Brian Andrew Stearns, Encinitas, CA (US); Christopher David King, Carlsbad, CA (US); Kevin Ross Holme, San Diego, CA (US)

(73) Assignee: Brickell Biotech, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/468,183

(22) Filed: Aug. 25, 2014

(65) Prior Publication Data

US 2016/0136119 A1    May 19, 2016

Related U.S. Application Data

(63) Continuation of application No. 12/846,690, filed on Jul. 29, 2010, now Pat. No. 8,815,917.

(60) Provisional application No. 61/231,660, filed on Aug. 5, 2009.

(51) Int. Cl.
*A61K 31/4418* (2006.01)
*A61K 31/195* (2006.01)
*C07D 213/64* (2006.01)
*C07C 229/00* (2006.01)

(52) U.S. Cl.
CPC .................... *A61K 31/195* (2013.01)

(58) Field of Classification Search
None
See application file for complete search history.

(56) References Cited

U.S. PATENT DOCUMENTS

| | | | |
|---|---|---|---|
| 8,067,445 B2 * | 11/2011 | Hutchinson | A61K 31/5375 514/351 |
| 8,168,678 B2 * | 5/2012 | Hutchinson | A61K 31/5375 514/564 |
| 8,338,484 B2 * | 12/2012 | Hutchinson | A61K 31/5375 514/564 |
| 8,362,044 B2 * | 1/2013 | Hutchinson | A61K 31/5375 514/351 |

* cited by examiner

*Primary Examiner* — Jeffrey S Lundgren
*Assistant Examiner* — Michael Schmitt
(74) *Attorney, Agent, or Firm* — Ted W. Whitlock

(57) ABSTRACT

Described herein is the $DP_2$ antagonist [2'-(3-benzyl-1-ethyl-ureidomethyl)-6-methoxy-4'-trifluoromethyl-biphenyl-3-yl]-acetic acid, or a pharmaceutically acceptable salt thereof. Also described are methods of preparing the DP2 antagonist, or a pharmaceutically acceptable salt thereof. Also described herein are pharmaceutical compositions suitable for administration to a mammal that include the $DP_2$ antagonist, or a pharmaceutically acceptable salt thereof, and methods of using such pharmaceutical compositions for treating respiratory diseases or conditions, allergic diseases or conditions, inflammatory diseases or conditions, as well as other prostaglandin $D_2$-dependent or prostaglandin $D_2$-mediated diseases or conditions.

13 Claims, 4 Drawing Sheets

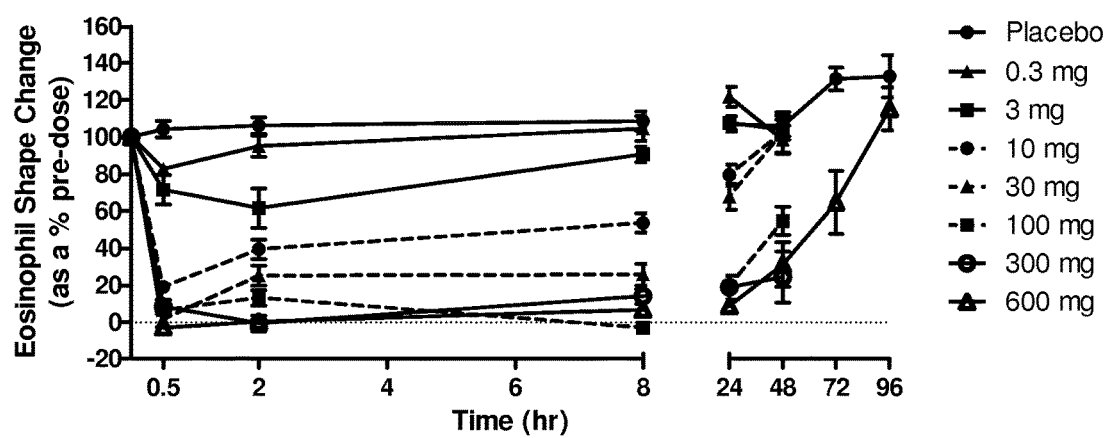
FIG. 1. Single Ascending Dose data for humans dosed with Compound 2

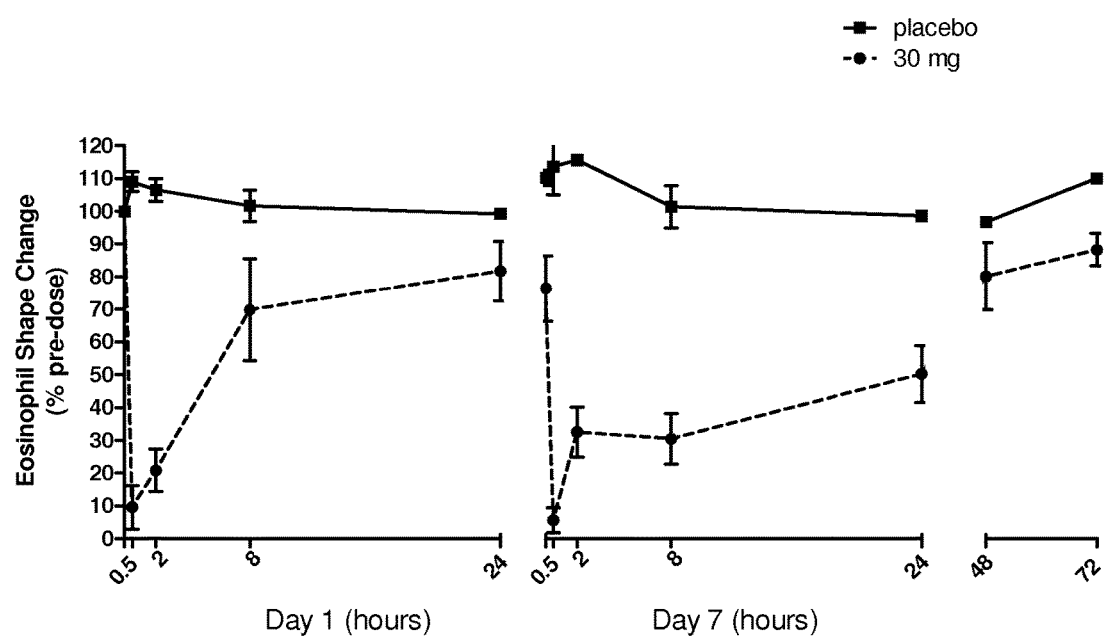
FIG. 2. Multiple Dose data for humans dosed with Compound 2

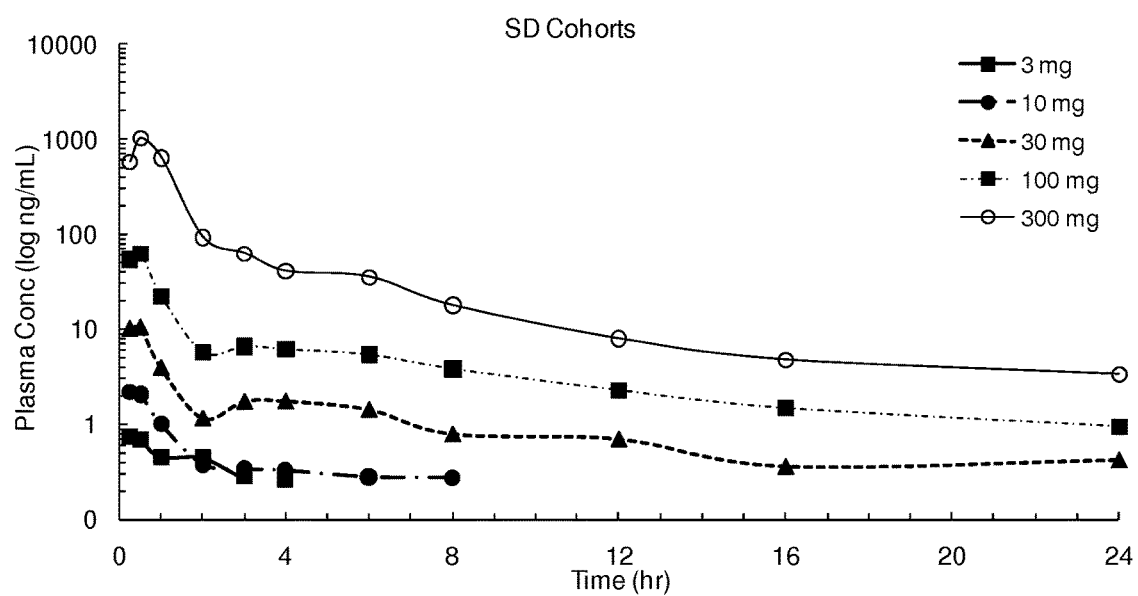
FIG. 3. Single ascending dose plasma levels of Compound 1.

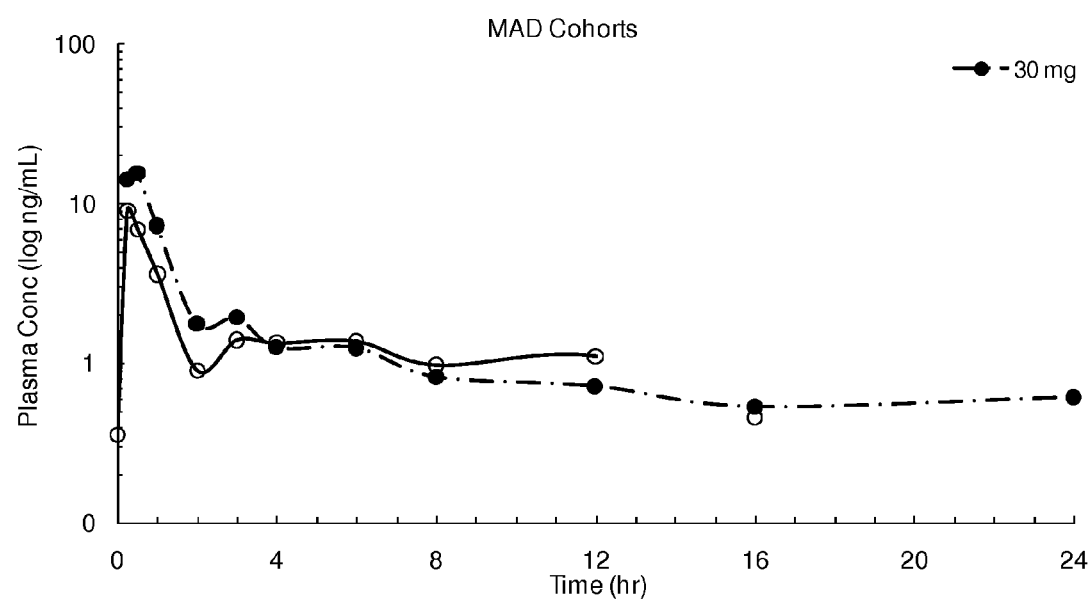
FIG. 4. Multiple dose plasma levels of Compound 1 on days 1 and 7.

DP2 ANTAGONIST AND USES THEREOF

RELATED APPLICATIONS

This application is a Continuation of U.S. application Ser. No. 12/846,690, filed Jul. 29, 2010, which claims the benefit of U.S. provisional patent application No. 61/231,660 entitled "DP2 ANTAGONIST AND USES THEREOF" filed on Aug. 5, 2009, each of which are incorporated by reference in their entirety.

FIELD OF THE INVENTION

Described herein is the $DP_2$ antagonist [2'-(3-benzyl-1-ethyl-ureidomethyl)-6-methoxy-4'-trifluoromethyl-biphenyl-3-yl]-acetic acid (Compound 1), pharmaceutically acceptable salts and metabolites thereof, as well as pharmaceutical compositions thereof, and methods of use thereof in the treatment or prevention of diseases or conditions associated with $DP_2$ activity.

BACKGROUND OF THE INVENTION

Prostaglandins are acidic lipids derived from the metabolism of arachidonic acid by the action of cyclooxygenase enzymes and downstream synthases. Prostaglandins have a diverse range of activities and have a well recognized role in a variety of disease or conditions, such as allergic diseases or conditions, inflammatory diseases or conditions, and respiratory diseases or conditions. Prostaglandin $D_2$ ($PGD_2$) is an acidic lipid mediator derived from the metabolism of arachidonic acid by cyclooxygenases and $PGD_2$ synthases. $PGD_2$ is produced by mast cells, macrophages and Th2 lymphocytes in response to local tissue damage as well as allergic inflammation in diseases such as asthma, rhinitis, and atopic dermatitis. Exogenous $PGD_2$ applied to bronchial airways elucidates many characteristics of an asthmatic response suggesting that $PGD_2$ plays an important pro-inflammatory role in allergic diseases.

$PGD_2$ binds to a number of receptors, which include the thromboxane-type prostanoid (TP) receptor, $PGD_2$ receptor (DP, also known as $DP_1$) and chemoattractant receptor-homologous molecule expressed on Th2 cells (CRTH2; also known as $DP_2$). $DP_2$ is associated with promoting chemotaxis and activation of Th2 lymphocytes, eosinophils and basophils. In particular, $PGD_2$ binds to $DP_2$, and mediates its effects through a $G_i$-dependant elevation in calcium levels and reduction of intracellular cyclic AMP. In Th2 lymphocytes, IL4, IL5 and IL13 cytokine production is stimulated. These cytokines have been implicated in numerous biological actions including, by way of example only, immunoglobulin E production, airway response, mucous secretion, and eosinophil recruitment.

SUMMARY OF THE INVENTION

Described herein is [2'-(3-benzyl-1-ethyl-ureidomethyl)-6-methoxy-4'-trifluoromethyl-biphenyl-3-yl]-acetic acid (Compound 1) including all pharmaceutically acceptable solvates (including hydrates), prodrugs, and metabolites thereof or a pharmaceutically acceptable salt of Compound 1 including (including hydrates), prodrugs, and metabolites thereof, and methods of uses thereof. Compound 1, as well as the pharmaceutically acceptable solvates thereof, are used in the manufacture of medicaments for the treatment or prevention of prostaglandin $D_2$ mediated and/or prostaglandin $D_2$ dependent diseases, disorders, or conditions. Also described are pharmacokinetic and pharmacodynamic properties of such formulations in mammals, including humans. Compound 1 is a DP2 antagonist.

Described herein are pharmaceutical compositions comprising Compound 1, or a pharmaceutically acceptable salt thereof (e.g. the sodium salt) as the active ingredient in the pharmaceutical composition; and at least one pharmaceutically acceptable inactive ingredient selected from among excipients, diluents, and carriers.

In one aspect, provided is a pharmaceutically acceptable salt of [2'-(3-benzyl-1-ethyl-ureidomethyl)-6-methoxy-4'-trifluoromethyl-biphenyl-3-yl]-acetic acid (Compound 1), wherein the pharmaceutically acceptable salt is a calcium salt, potassium salt, sodium salt, magnesium salt, ammonium salt, L-arginine salt, L-lysine salt, or a N-methyl-D-glucamine salt. In some embodiments, the pharmaceutically acceptable salt is a sodium salt. In some embodiments, the pharmaceutically acceptable salt of Compound 1 is Compound 2.

In some embodiments, Compound 2 is amorphous. In some embodiments, Compound 1 is amorphous.

In some embodiments, Compound 2 is hydrated.

In some embodiments, Compound 2 was obtained from a solution comprising heptane and ethanol. In some embodiments, Compound 2 comprises a detectable amount of heptane, ethanol or a combination of heptane and ethanol.

In some embodiments, a sample of Compound 1 comprises a detectable amount of palladium that is less than 20 ppm. In some embodiments, a sample of Compound 1 comprises a detectable amount of palladium that is less than 10 ppm. In some embodiments, a sample of Compound 1 comprises a detectable amount of palladium that is less than 2 ppm. In some embodiments, a sample of Compound 1 does not include palladium. In some embodiments, a sample of Compound 2 comprises a detectable amount of palladium that is less than 20 ppm. In some embodiments, a sample of Compound 2 comprises a detectable amount of palladium that is less than 10 ppm. In some embodiments, a sample of Compound 2 comprises a detectable amount of palladium that is less than 2 ppm. In some embodiments, a sample of Compound 2 does not include palladium.

Described herein are pharmaceutical compositions comprising Compound 1 and/or pharmaceutically acceptable salts thereof. In some embodiments, the pharmaceutical compositions comprise Compound 1. In other embodiments, the pharmaceutical compositions comprise a pharmaceutically acceptable salt of Compound 1. In some embodiments, the pharmaceutically acceptable salt of Compound 1 is Compound 2. In some embodiments, the pharmaceutical compositions further comprise at least one pharmaceutically acceptable inactive ingredient selected from among excipients, diluents, and carriers.

In one aspect, provided herein is a pharmaceutical composition comprising: a. Compound 1 or a pharmaceutically acceptable salt of Compound 1; and b. at least one pharmaceutically acceptable excipient. In some embodiments, the pharmaceutical composition comprises Compound 1. In some embodiments, the pharmaceutical composition comprises Compound 2. In one aspect, provided herein is a pharmaceutical composition comprising: a. a pharmaceutically acceptable salt of Compound 1; and b. at least one pharmaceutically acceptable excipient.

In some embodiments, Compound 1 is greater than 96% pure. In some embodiments, Compound 1 is greater than 97% pure. In some embodiments, Compound 1 is greater than 98% pure. In some embodiments, Compound 1 is greater than 99% pure. In some embodiments, Compound 2 is greater than 96% pure. In some embodiments, Compound 2 is greater than 97% pure. In some embodiments, Compound 2 is greater than 98% pure. In some embodiments, Compound 2 is greater than 99% pure.

In some embodiments the pharmaceutical compositions described herein comprise less than 10 ppm of palladium. In some embodiments, the pharmaceutical compositions described herein comprise less than 5 ppm of palladium. In some embodiments, the pharmaceutical compositions described herein comprise less than 2 ppm of palladium. In some embodiments, the pharmaceutical compositions described herein comprise less than 1 ppm of palladium. In some embodiments, the pharmaceutical compositions described herein do not include palladium.

In some embodiments, the pharmaceutical composition is in a form suitable for oral administration to a mammal. In some embodiments, the pharmaceutical composition is in the form of a pill, capsule, tablet, aqueous solution, aqueous suspension, non-aqueous solution, or non-aqueous suspension.

In some embodiments, the pharmaceutical composition is in the form of a tablet. In some embodiments, the pharmaceutical composition is in the form of an immediate release tablet, an enteric coated tablet, or a sustained release tablet. In some embodiments, the pharmaceutical composition is in the form of a moisture barrier coated tablet.

In some embodiments, the pharmaceutical composition is in the form of a capsule.

In some embodiments, the pharmaceutical composition is in the form of an aqueous solution or aqueous suspension.

In some embodiments, a single dose of the pharmaceutical composition comprises about 0.3 mg to about 600 mg of Compound 1. In some embodiments, a single dose of the pharmaceutical composition comprises about 0.3 mg to about 600 mg of a pharmaceutically acceptable salt of Compound 1. In some embodiments, a single dose of the pharmaceutical composition comprises about 0.3 mg to about 600 mg of Compound 2.

In some embodiments, a single dose of the pharmaceutical composition when administered to healthy adult human subjects in the fasted state provides 80-100% inhibition of ex vivo $PGD_2$-stimulated eosinophil shape change in whole blood at $C_{max}$.

In some embodiments, a single dose of the pharmaceutical composition when administered to healthy adult human subjects in the fasted state provides about 25-100% inhibition of ex vivo $PGD_2$-stimulated eosinophil shape change in whole blood after about 24 hours following administration.

In some embodiments, a single dose of the pharmaceutical composition when administered to healthy adult human subjects in the fasted state provides about 30-70% inhibition of ex vivo $PGD_2$-stimulated eosinophil shape change in whole blood after about 24 hours following administration.

In one aspect, provided is an oral solid dosage form pharmaceutical composition comprising: a) Compound 1 or a pharmaceutically acceptable salt of [2'-(3-benzyl-1-ethyl-ureidomethyl)-6-methoxy-4'-trifluoromethyl-biphenyl-3-yl]-acetic acid (Compound 1); and b) at least one inactive pharmaceutical ingredient. In one aspect, provided is an oral solid dosage form pharmaceutical composition comprising: a) Compound 1; and b) at least one inactive pharmaceutical ingredient. In one aspect, provided is an oral solid dosage form pharmaceutical composition comprising: a) a pharmaceutically acceptable salt of [2'-(3-benzyl-1-ethyl-ureidomethyl)-6-methoxy-4'-trifluoromethyl-biphenyl-3-yl]-acetic acid (Compound 1), wherein the pharmaceutically acceptable salt is a calcium salt, potassium salt, sodium salt, magnesium salt, ammonium salt, L-arginine salt, L-lysine salt, or a N-methyl-D-glucamine salt; and b) at least one inactive pharmaceutical ingredient.

In some embodiments, the pharmaceutically acceptable salt of [2'-(3-benzyl-1-ethyl-ureidomethyl)-6-methoxy-4'-trifluoromethyl-biphenyl-3-yl]-acetic acid (Compound 1) is [2'-(3-benzyl-1-ethyl-ureidomethyl)-6-methoxy-4'-trifluoromethyl-biphenyl-3-yl]-acetic acid, sodium salt (Compound 2).

In some embodiments, the oral solid dosage form is in the form of a tablet, pill or capsule.

In some embodiments, the pharmaceutical composition comprises about 1 mg, about 3 mg, about 10 mg, about 30 mg, about 60 mg, about 100 mg, about 200 mg, about 250 mg, about 300 mg or about 600 mg of Compound 1 or a pharmaceutically acceptable salt thereof. In some embodiments, the pharmaceutical composition comprises about 1 mg, about 3 mg, about 10 mg, about 30 mg, about 60 mg, about 100 mg, about 200 mg, about 250 mg, about 300 mg or about 600 mg of Compound 1. In some embodiments, the pharmaceutical composition comprises about 1 mg, about 3 mg, about 10 mg, about 30 mg, about 60 mg, about 100 mg, about 200 mg, about 250 mg, about 300 mg or about 600 mg of Compound 2.

In some embodiments, the oral solid dosage form is in the form of a tablet. In some embodiments, the oral solid dosage form is in the form of an immediate release tablet, an enteric coated tablet, or a sustained release tablet. In some embodiments, the oral solid dosage form is in the form of an immediate release tablet. In some embodiments, the oral solid dosage form is in the form of a moisture barrier coated tablet.

In some embodiments, the oral solid dosage form pharmaceutical composition comprises from about 10% by weight to about 20% by weight of Compound 1 or a pharmaceutically acceptable salt thereof. In some embodiments, the oral solid dosage form pharmaceutical composition comprises from about 10% by weight to about 20% by weight of Compound 1. In some embodiments, the oral solid dosage form pharmaceutical composition comprises from about 10% by weight to about 20% by weight of Compound 2.

In some embodiments, the oral solid dosage form pharmaceutical composition is in the form of a capsule.

In some embodiments, the capsule is in the form of a hard gelatine capsule or hypromellose (HPMC) capsule. In some embodiments, the capsule comprises at least one excipient in addition to the hard gelatine capsule or hypromellose (HPMC) capsule.

In one aspect, provided is a pharmaceutical composition that provides at least one metabolite of [2'-(3-benzyl-1-ethyl-ureidomethyl)-6-methoxy-4'-trifluoromethyl-biphenyl-3-yl]-acetic acid (Compound 1) after administration to a mammal. In some embodiments, the at least one metabolite is selected from among: 2-(2'-((ethylamino)methyl)-6-methoxy-4'-(trifluoromethyl)biphenyl-3-yl)acetic acid (M1); the acyl gluconuride of [2'-(3-benzyl-1-ethyl-ureidomethyl)-6-methoxy-4'-trifluoromethyl-biphenyl-3-yl]-acetic acid (M2); [2'-(1-ethyl-ureidomethyl)-6-methoxy-4'-trifluoromethyl-biphenyl-3-yl]-acetic acid (M3); [2'-(3-benzyl-ureidomethyl)-6-methoxy-4'-trifluoromethyl-biphenyl-3-yl]-acetic acid (M6); [2'-(3-benzyl-1-ethyl-ureidomethyl)-6-hydroxy-4'-trifluoromethyl-biphenyl-3-yl]-acetic acid (M8); or combinations thereof. In some embodiments, the least one metabolite is the acyl gluconuride of [2'-(3-benzyl-1-ethyl-ureidomethyl)-6-methoxy-4'-trifluoromethyl-biphenyl-3-yl]-acetic acid. In some embodiments, the pharmaceutical composition is a pharmaceutical composition as described herein.

Also provided is a method of treating or preventing a respiratory disease or condition, an inflammatory disease or condition or an allergic disease or condition, or combinations thereof, in a mammal comprising administering to the mammal an oral pharmaceutical composition as described herein.

In some embodiments, the respiratory disease or condition, inflammatory disease or condition or allergic disease or condition is asthma, adult respiratory distress syndrome, isocapnic hyperventilation, rhinitis, chronic obstructive pulmonary disease, chronic bronchitis, emphysema, pulmonary hypertension, cystic fibrosis, an allergic ocular disease or condition, an inflammatory ocular disease or condition, an allergic skin disease or condition, or an inflammatory skin disease or condition.

In some embodiments, the respiratory disease or condition, inflammatory disease or condition or allergic disease or condition is asthma, rhinitis, dermatitis, ocular inflammation, or conjunctivitis.

Also provided is a method of treating or preventing asthma in a mammal comprising administering to the mammal an oral pharmaceutical composition as described herein. In some embodiments, the asthma is allergic asthma, non-allergic asthma, acute severe asthma, chronic asthma, clinical asthma, nocturnal asthma, allergen-induced asthma, aspirin-sensitive asthma, exercise-induced asthma, child-onset asthma, adult-onset asthma, cough-variant asthma, neutrophilic asthma, occupational asthma, steroid-resistant asthma, or seasonal asthma.

Also provided is a method of treating rhinitis in a mammal comprising administering to the mammal an oral pharmaceutical composition as described herein. In some embodiments, the rhinitis is allergic rhinitis, non-allergic rhinitis, chronic rhinitis, allergen-induced rhinitis, aspirin-sensitive rhinitis, child-onset rhinitis, adult-onset rhinitis, occupational rhinitis, steroid-resistant rhinitis, seasonal rhinitis, perennial rhinitis, rhinosinusitis, or rhinopolyposis. In some embodiments, the rhinitis is allergic rhinitis.

Also provided is a method of treating chronic obstructive pulmonary disease (COPD) in a mammal comprising administering to the mammal an oral pharmaceutical composition as described herein.

In some embodiments, the mammal is a human.

In some embodiments, the method further comprises administering the mammal at least one additional pharmaceutical agent selected from inhaled corticosteroids, short acting beta-agonists, long acting beta-agonists, leukotriene modulators, and antihistamines.

In some embodiments, the pharmaceutical composition further comprises at least one additional pharmaceutical agent selected from inhaled corticosteroids, short acting beta-agonists, long acting beta-agonists, leukotriene modulators, and antihistamines.

Also provided is an article of manufacture comprising multiple unit doses of the oral solid dosage form pharmaceutical composition described herein in a high-density polyethylene (HDPE) bottle equipped with a high-density polyethylene (HDPE) cap.

In some embodiments, high-density polyethylene (HDPE) bottle further comprises an aluminum foil induction seal and silica gel desiccant.

Also provided is the use of Compound 1 or a pharmaceutically acceptable salt thereof (e.g. Compound 2) for the manufacture of a medicament for the treatment or prevention of a respiratory disease or condition in a human.

Also provided is the use of Compound 1 or a pharmaceutically acceptable salt thereof (e.g. Compound 2) for the manufacture of a medicament for the treatment of asthma in a human. In some embodiments, the asthma is persistent, uncontrolled asthma.

Also provided is the use of Compound 1 or a pharmaceutically acceptable salt thereof (e.g. Compound 2) for the manufacture of a medicament for the treatment or prevention of rhinitis in a human. In some embodiments, the rhinitis is allergic rhinitis.

Also provided is the use of Compound 1 or a pharmaceutically acceptable salt thereof (e.g. Compound 2) for the manufacture of a medicament for the treatment of chronic obstructive pulmonary disease in a human Also provided is the use of Compound 1 or a pharmaceutically acceptable salt thereof (e.g. Compound 2) for the manufacture of a medicament for the treatment of an ocular disease or condition in a human. In some embodiments, the ocular disease or condition is conjunctivitis.

Also provided is the use of Compound 1 or a pharmaceutically acceptable salt thereof (e.g. Compound 2) for the manufacture for the treatment of a skin disease or condition in a human. In some embodiments, the skin disease or condition is dermatitis.

Described in certain embodiments herein is a pharmaceutical composition comprising an active ingredient that antagonizes $DP_2$ receptors in a mammal and does not substantially inhibit at least one Cytochrome P450 enzyme selected from CYP 3A4, CYP 1A2, CYP 2A6, CYP 2B6, CYP 2C8, CYP 2C9, CYP 2C19, CYP 2D6, and CYP 2E1 at doses up to 40 µM or 50 µM. In some embodiments, the pharmaceutical composition does not substantially induce Cytochrome P450 CYP 3A4, CYP 2C9, CYP 1A2, CYP 2C19, or CYP 2D6 at doses up to 40 µM, or up to 50 µM. In certain embodiments, the active ingredient is Compound 1, or a pharmaceutically acceptable salt thereof. In a specific embodiment, the active ingredient is Compound 1. In another specific embodiment, the active ingredient is Compound 2.

Described in certain embodiments herein is an oral solid dosage form pharmaceutical composition comprising: (a) Compound 2; and (b) optionally at least one inactive pharmaceutical ingredient. In specific embodiments, the oral solid dosage form pharmaceutical composition is in the form of a capsule. In more specific embodiments, the capsule is a hard gelatine capsule or hypromellose (HPMC) capsule. In various embodiments, the capsules described herein comprise at least one excipient or no excipients.

In one aspect provided are methods for treating $PGD_2$-dependent or $PGD_2$-mediated diseases or conditions in a mammal, comprising administering to the mammal at least once an effective amount of Compound 1, or a pharmaceutically acceptable salt thereof (e.g. Compound 2).

In one aspect provided are methods for treating mammals with an inflammatory and/or allergic condition comprising administering to the mammal at least once an effective amount of Compound 1, or a pharmaceutically acceptable salt thereof (e.g. Compound 2).

In one aspect, provided herein is an oral pharmaceutical composition as described herein comprising Compound 1 or a pharmaceutically acceptable salt thereof as the active ingredient for use in the treatment or prevention of an inflammatory and/or allergic condition in a mammal. In some embodiments, the active ingredient is Compound 1. In other embodiments, the active ingredient is Compound 2.

In one aspect are methods for treating inflammation in a mammal comprising administering to the mammal at least once an effective amount of Compound 1, or a pharmaceutically acceptable salt thereof (e.g. Compound 2).

In one aspect are methods for treating respiratory diseases in a mammal comprising administering to the mammal at least once an effective amount of Compound 1, or a pharmaceutically acceptable salt thereof (e.g. Compound 2). Respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, allergic rhinitis, vasomotor rhinitis, vascular responses, endotoxin shock, fibrogenesis, pulmonary fibrosis, allergic diseases, chronic inflammation, and adult respiratory distress syndrome. In a specific embodiment of this aspect, the respiratory disease is asthma.

In one aspect are methods for treating or preventing rhinitis in a mammal comprising administering to the mammal at least once an effective amount of Compound 1, or a pharmaceutically acceptable salt thereof (e.g. Compound 2). Rhinitis includes: allergic rhinitis, non-allergic rhinitis, chronic rhinitis, allergen-induced rhinitis, aspirin-sensitive rhinitis, child-onset rhinitis, adult-onset rhinitis, occupational rhinitis, steroid-resistant rhinitis, seasonal rhinitis, perennial rhinitis, rhinosinusitis, and rhinopolyposis.

In one aspect are methods for treating chronic obstructive pulmonary disease in a mammal comprising administering to the mammal at least once an effective amount of Compound 1, or a pharmaceutically acceptable salt thereof (e.g. Compound 2). Chronic obstructive pulmonary disease includes, but is not limited to, chronic bronchitis or emphysema, pulmonary hypertension, interstitial lung fibrosis and/or airway inflammation and cystic fibrosis.

In one aspect are methods for preventing increased mucosal secretion and/or edema in a mammal comprising administering to the mammal at least once an effective amount of Compound 1, or a pharmaceutically acceptable salt thereof (e.g. Compound 2).

In one aspect are methods for preventing eosinophil and/or basophil and/or dendritic cell and/or neutrophil and/or monocyte recruitment in a mammal comprising administering to the mammal at least once an effective amount of Compound 1, or a pharmaceutically acceptable salt thereof (e.g. Compound 2).

In another aspect are methods for preventing ocular disease (for example, ocular inflammation, allergic conjunctivitis, vernal keratoconjunctivitis and papillary conjunctivitis) in a mammal comprising administering to the mammal at least once an effective amount of Compound 1, or a pharmaceutically acceptable salt thereof (e.g. Compound 2).

In another aspect are methods for preventing or treating acute or chronic disorders involving recruitment or activation of eosinophils in a mammal comprising administering to the mammal at least once an effective amount of Compound 1, or a pharmaceutically acceptable salt thereof (e.g. Compound 2).

In any of the aforementioned aspects, the mammal is a human. In any of the aforementioned aspects, the mammal is a human, including embodiments wherein (a) the human has an asthmatic condition or one or more other condition(s) selected from the group consisting of allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, child-onset asthma, adult-onset asthma, cough-variant asthma, occupational asthma, steroid-resistant asthma, seasonal asthma, allergic rhinitis, non-allergic rhinitis, chronic rhinitis, allergen-induced rhinitis, aspirin-sensitive rhinitis, child-onset rhinitis, adult-onset rhinitis, occupational rhinitis, steroid-resistant rhinitis, seasonal rhinitis, perennial rhinitis, rhinosinusitis, rhinopolyposis, and chronic obstructive pulmonary disease.

In any of the aforementioned aspects are further embodiments comprising single administrations of the effective amount of Compound 1, or a pharmaceutically acceptable salt thereof (e.g. Compound 2), including further embodiments in which Compound 1, or a pharmaceutically acceptable salt thereof (e.g. Compound 2) is (i) administered once-a-day; (ii) is administered twice-a-day; or (iii) is administered multiple times over the span of one day.

In any of the aforementioned aspects are further embodiments comprising multiple administrations of the effective amount of the compound, including further embodiments in which (i) the compound is administered in a single dose; (ii) the time between multiple administrations is every 6 hours; (iii) the time between multiple administrations is every 8 hours; (iv) the time between multiple administrations is every 12 hours.

In some embodiments, the pharmaceutical composition is administered daily to the mammal.

In some embodiments, the pharmaceutical composition is administered in treatment cycles comprising: (a) a first period during which Compound 2 is administered daily to the mammal; and (b) a second period of at least seven days during which the Compound 1, or a pharmaceutically acceptable salt thereof (e.g. Compound 2) is administered to the mammal in a reduced amount as compared to (a).

In some embodiments, the methods of treatment or prevention disclosed herein comprise a drug holiday, wherein the administration of Compound 1, or a pharmaceutically acceptable salt thereof (e.g. Compound 2) is temporarily suspended or the dose being administered is temporarily reduced; at the end of the drug holiday dosing is resumed. In some embodiments, the length of the drug holiday varies from 2 days to 1 year.

In one aspect, Compound 1, or a pharmaceutically acceptable salt thereof (e.g. Compound 2) is used in the manufacture of medicaments for the treatment of a $PGD_2$-dependent or $PGD_2$-mediated respiratory disease or condition in a mammal whose symptoms of the respiratory disease or condition are not adequately controlled by corticosteroids. In a specific embodiment, the respiratory disease or condition is asthma.

Compound 1, or a pharmaceutically acceptable salt thereof (e.g. Compound 2) for treating any of the diseases or conditions disclosed herein.

A pharmaceutical composition comprising Compound 1, or a pharmaceutically acceptable salt thereof (e.g. Compound 2) for use in any of the uses and methods disclosed herein.

Use of Compound 1, or a pharmaceutically acceptable salt thereof (e.g. Compound 2) in the manufacture of a medicament for treating or preventing any of the diseases disclosed herein in a mammal. In one aspect, Compound 1 or a pharmaceutically acceptable salt thereof (e.g. Compound 2) is used in the treatment of a respiratory disease or condition in a mammal.

In one aspect is the use of Compound 1 or a pharmaceutically acceptable salt thereof (e.g. Compound 2) for the manufacture of a medicament for the treatment of asthma in a human. In one aspect is the use of Compound 1 or a pharmaceutically acceptable salt thereof (e.g. Compound 2) for the manufacture of a medicament for the treatment or prevention of allergic rhinitis in a human. In one aspect is the use of Compound 1 or a pharmaceutically acceptable salt thereof (e.g. Compound 2) for the manufacture of a medicament for the treatment of chronic obstructive pulmonary disease in a human. In one aspect is the use of Compound 1 or a pharmaceutically acceptable salt thereof (e.g. Compound 2) for the manufacture of a medicament for the treatment of ocular disease in a human. In one aspect is the use of Compound 1 or a pharmaceutically acceptable salt thereof (e.g. Compound 2) for the manufacture of a medicament for the treatment of skin disease in a human.

In one aspect, described herein is a method of increasing the bioavailability of an orally administered dose of Compound 1, or a pharmaceutically acceptable salt thereof (e.g. Compound 2) in healthy human patients comprising orally administering to a mammal: (1) a dose of Compound 1, or a pharmaceutically acceptable salt thereof (e.g. Compound 2); and (2) an inhibitor of a UDP-glucuronosyltransferase enzyme normally present in the mammal.

In any of the aforementioned aspects involving the prevention or treatment of inflammation are further embodiments comprising: (a) monitoring inflammation in a mammal; (b) measuring bronchoconstriction in a mammal; (c) measuring eosinophil and/or basophil and/or dendritic cell and/or neutrophil and/or monocyte and/or lymphocyte recruitment in a mammal; (d) monitoring mucosal secretion in a mammal; (e) measuring mucosal edema in a mammal; and/or (e) measuring inhibition of $PGD_2$-induced eosinophil shape change (ESC) in a mammal; and/or (f) measuring Th2 cytokine levels in a mammal.

Also described herein are process for the preparation of Compound 1 and pharmaceutically acceptable salts thereof. In one aspect, the pharmaceutically acceptable salt of Compound 1 is Compound 2.

In one aspect, described is a process for the preparation of amorphous Compound 2 comprising the steps of:
(1) concentrating Compound 2 from ethanol to obtain solids of Compound 2;
(2) adding heptane to Compound 2 of step (1) to form a filterable slurry; and
(2) isolating the solids that are formed from step (2) to provide amorphous Compound 2.

In one embodiment, described herein is a process for the synthesis of [2'-(3-benzyl-1-ethyl-ureidomethyl)-6-methoxy-4'-trifluoromethyl-biphenyl-3-yl]-acetic acid (Compound 1) comprising the steps of:
(1) reacting a compound of Formula V, or a salt thereof:

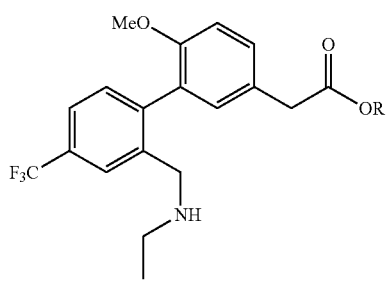

Formula V wherein, R is $C_1$-$C_6$alkyl,
with (i) benzylisocyanate, or (ii) phosgene followed by benzylamine, to provide a compound of Formula VI:

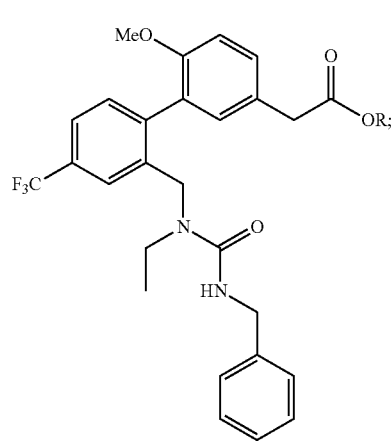

Formula VI (2) hydrolysis of the ester group of the compound of Formula VI to provide Compound 1.

In some embodiments, step (2) comprises treatment of the compound of Formula VI with a suitable base in a suitable solvent followed by a pH adjustment. In some embodiments, the suitable base for the hydrolysis reaction is sodium hydroxide or lithium hydroxide. In some embodiments, the suitable base for the hydrolysis reaction is sodium hydroxide. In some embodiments, the pH is adjusted with hydrochloric acid. Suitable solvents for the hydrolysis include, but are not limited to, water, methanol, ethanol, tetrahydrofuran, methyl tert-butyl ether, or combinations thereof. Compound 1 is then treated with sodium hydroxide in ethanol to furnish Compound 2.

In some embodiments, Compound 2 is prepared from compound VI by performing a one-step hydrolysis and salt forming reaction. In some embodiments, the one-step hydrolysis and salt forming reaction includes treatment of compound VI with sodium hydroxide in a suitable solvent In some embodiments, the compound of Formula V is prepared by:
reacting a compound of Formula IV:

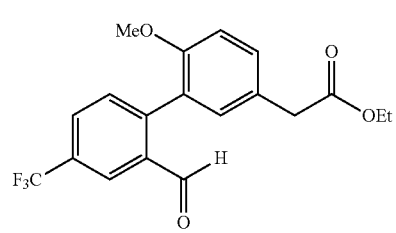

Formula IV wherein R is $C_1$-$C_6$alkyl;
with ethylamine, or a salt thereof, in the presence of a reducing agent in a suitable solvent.

In some embodiments, the reducing agent is hydride reagent. In some embodiments, the reducing agent is sodium cyanoborohydride.

In some embodiments, the compound of Formula IV is prepared by:
(a) reacting a compound of Formula III:

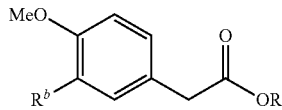

Formula III wherein R is $C_1$-$C_6$alkyl, and $R^b$ is a boronic acid or boronic ester,
with

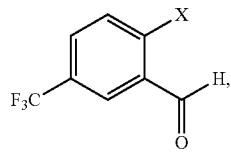

wherein X is a leaving group,
in the presence of a coupling catalyst, a suitable base, and in a suitable solvent, to provide a compound of Formula IV; or
(b) reacting a compound of Formula VII

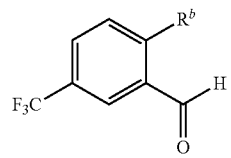

Formula VII wherein, $R^b$ is a boronic acid or boronic ester,
with a compound of Formula II

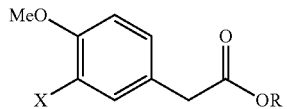

Formula II wherein, R is $C_1$-$C_6$alkyl, and X is a leaving group,
in the presence of a coupling catalyst, a suitable base, and in a suitable solvent, to provide a compound of Formula V.

In some embodiments, the coupling catalyst is a palladium catalyst.

In some embodiments, the suitable base is an organic base or inorganic base. In some embodiments, the suitable base is an organic base. In some embodiments, the suitable base is an inorganic base. In some embodiments, the suitable base is triethylamine, diisopropylethylamine, 1,2,2,6,6-pentamethylpiperidine, tributylamine, sodium bicarbonate, sodium carbonate, potassium carbonate, cesium carbonate, sodium acetate, potassium acetate, sodium phosphate or potassium phosphate.

In some embodiments, the suitable solvent is a solvent used in Suzuki reactions. In some embodiments, the suitable solvent is dimethylformamide, tetrahydrofuran, dioxane, water, or combinations thereof. In some embodiments, the suitable solvent is tetrahydrofuran, dioxane, water, or combinations thereof.

In some embodiments, R is $C_1$-$C_4$alkyl. In some embodiments, R is —$CH_3$, —$CH_2CH_3$, —$CH_2CH_2CH_3$, —$CH(CH_3)_2$, —$CH_2CH_2CH_2CH_3$, or —$C(CH_3)_3$. In some embodiments, R is —$CH_3$ or —$CH_2CH_3$.

In some embodiments, X is halide or triflate. In some embodiments, X is Cl, Br, I, or —$OSO_2CF_3$.

In some embodiments, $R^b$ is

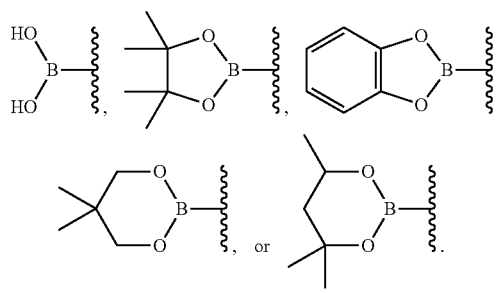

In some embodiments, $R^b$ is

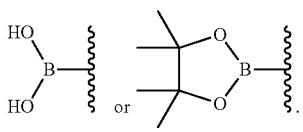

In some embodiments, $R^b$ is

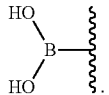

In some embodiments, $R^b$ is

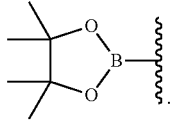

The disclosed processes provide for the synthesis of Compound 1 and pharmaceutically acceptable salts thereof (e.g. Compound 2). The processes disclosed herein are particularly applicable to large scale chemical production of Compound 1 and pharmaceutically acceptable salts thereof. Also described herein are processes for the preparation of Compound 2, in good yield that have good solubility and good oral bioavailability.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

BRIEF DESCRIPTION OF THE FIGURES

FIG. 1 illustrates the ex vivo PGD$_2$-stimulated eosinophil shape change in whole blood after single dose administration of oral solutions of Compound 2 to humans.

FIG. 2 illustrates the ex vivo PGD$_2$-stimulated eosinophil shape change in whole blood after multiple dose administration of oral solutions of Compound 2 to humans.

FIG. 3 illustrates the plasma concentrations of Compound 1 after single dose administration of oral solutions of Compound 2 to humans.

FIG. 4 illustrates the plasma concentrations of Compound 1 after multiple dose administration of oral solutions of Compound 2 to humans.

DETAILED DESCRIPTION OF THE INVENTION

Prostaglandin D$_2$ (PGD$_2$) is an acidic lipid derived from the metabolism of arachidonic acid by cyclooxygenases and PGD$_2$ synthases. PGD$_2$ is produced by mast cells, macrophages and Th2 lymphocytes in response to local tissue damage as well as in response allergic inflammation observed in diseases such as asthma, rhinitis, and atopic dermatitis. More specifically, exogenous PGD$_2$ applied to bronchial airways elicits many responses that are characteristic of acute asthma.

PGD$_2$ is a major mast cell product that acts via two receptors, the D-type prostanoid (DP, also known as DP$_1$) and the chemoattractant receptor-homologous molecule expressed on Th2 cells (CRTH2, also known as DP$_2$) receptors. DP$_2$ mediates the chemotaxis of eosinophils, basophils, and Th2 lymphocytes, and DP$_1$ receptor plays an important role in eosinophil trafficking. DP$_1$ antagonists do not inhibit the release of eosinophils when induced by the DP$_2$-selective agonists. However, eosinophils in human bone marrow specimens express DP$_1$ and DP$_2$ receptors at similar levels and human peripheral blood expresses both DP$_1$ and DP$_2$, but the DP$_1$ receptor is expressed at lower levels. In agreement with this, the chemotaxis of human peripheral blood eosinophils is inhibited by both DP$_1$ and DP$_2$ antagonists. Accordingly, DP$_1$, DP$_2$ and dual DP$_1$/DP$_2$ antagonists are useful in the treatment of allergic inflammation.

Activation of DP$_2$ is associated with chemotaxis and activation of Th2 lymphocytes, eosinophils and basophils. In particular, PGD$_2$ binds to DP$_2$ and mediates many of its effects through a G$_i$-dependent elevation of intracellular calcium levels and reduction of cyclic AMP. In Th2 lymphocytes, IL4, IL5 and IL13 cytokine production are also stimulated by DP$_2$ activation. These cytokines have been implicated in numerous biological actions including, by way of example only, immunoglobulin E production, airway response, mucous secretion, and eosinophil recruitment.

The terms CRTH2 and DP$_2$, refer to the same receptor and are used interchangeably herein. Likewise, another common name for DP is DP$_1$, and the two terms are used interchangeably herein. DP$_2$ and DP$_2$ receptor are used interchangeably.

In asthma and other allergic inflammatory conditions, mast cells produce PGD$_2$, an inflammatory mediator in the prostaglandin pathway which mediates a number of signs of asthma. The DP$_2$ receptor mediates pro-inflammatory responses of PGD$_2$ that are important in asthma including the activation and chemotaxis of eosinophils, basophils, Th2 cells, and the release of Th2 cytokines such as IL-4, IL-5, and IL-13.

In patients with cystic fibrosis, the DP$_2$ receptor is expressed on sputum neutrophils and not on circulating neutrophils (Tirouvanziam, R., et al., 2008. *Proc. Nat. Acad. Sci. USA* 105:4335-4339), which indicate a role for DP$_2$ in neutrophil-mediated airway inflammation such as observed in severe, non-allergic asthma, corticosteroid-resistant asthma, and chronic obstructive pulmonary disease (COPD).

Blocking the PGD$_2$-mediated activation of the DP$_2$ receptor has not been associated with any specific safety concerns in preclinical studies using DP$_2$ antagonists. Knock-out mice are healthy and fertile, and multiple studies have shown the DP$_2$ deficient mice to be protected from allergic inflammatory responses (Pettipher, R., et al., 2007. *Nature Drug Discovery* 6: 313-325).

Although there are a number of selective DP$_2$ antagonists in clinical trials for asthma, allergic rhinitis, and COPD, there is no marketed selective DP$_2$ antagonist.

Compound 1 is a selective, orally bioavailable, small molecule DP$_2$ antagonist. Compound 1 binds competitively to the DP$_2$ receptor with high affinity (IC$_{50}$=12.2 nM with human serum albumin), and is a full antagonist. Compound 1 inhibits the functional activity of the DP$_2$ receptor as measured by inhibiting the eosinophil shape change (ESC) stimulated by the addition of PGD$_2$ to human whole blood (IC$_{50}$=2.7 nM). In vitro scintillation proximity assay (SPA) experiments with the DP$_2$ receptor have demonstrated that Compound 1 has a longer off-rate than PGD$_2$. In some embodiments, a longer off-rate from the DP$_2$ receptor than PGD$_2$ provides a prolonged pharmacodynamic effect in vivo.

Compound 1 has been shown to be active in preclinical and clinical pharmacology models of allergic rhinitis, asthma, and leukocyte recruitment. In one embodiment, the data support a once a day oral administration.

Diseases or Conditions

Compound 1, or a pharmaceutically salt thereof (e.g. Compound 2), is used in the treatment or prevention of PGD$_2$-dependent or PGD$_2$-mediated diseases or conditions in mammals. The term "PGD$_2$-dependent", as used herein, refers to conditions or disorders that would not occur, or would not occur to the same extent, in the absence of PGD$_2$. The term "PGD$_2$-mediated", as used herein, refers to refers to conditions or disorders that might occur in the absence of PGD$_2$ but can occur in the presence of PGD$_2$.

In one aspect, PGD$_2$-dependent or PGD$_2$-mediated diseases or conditions include, but are not limited to, asthma, rhinitis, allergic conjuctivitis, atopic dermatitis, chronic obstructive pulmonary disease (COPD), pulmonary hypertension, interstitial lung fibrosis, cystic fibrosis, arthritis, allergy, psoriasis, inflammatory bowel disease, adult respiratory distress syndrome, myocardial infarction, stroke, arthritis, wound healing, endotoxic shock, cancer, pain, eosinophilic esophagitis, eosinophil-associated gastrointestinal disorders (EGID), idiopathic hypereosinophilic syndrome, otitis, airway constriction, mucus secretion, nasal congestion, increased microvascular permeability and recruitment of eosinophils, urticaria, sinusitis, uveitis, angioedema, anaphylaxia, chronic cough and Churg Strauss syndrome.

In some embodiments, Compound 1, or a pharmaceutically salt thereof (e.g. Compound 2), is used in the treatment of respiratory disease or conditions, allergic diseases or conditions, and/or inflammatory diseases or conditions.

In some embodiments, Compound 1, or a pharmaceutically salt thereof (e.g. Compound 2), is used in the treatment of respiratory diseases or conditions.

The term "respiratory disease," as used herein, refers to diseases affecting the organs that are involved in breathing, such as the nose, throat, larynx, eustachian tubes, trachea, bronchi, lungs, related muscles (e.g., diaphram and intercostals), and nerves. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, neutrophilic asthma, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

In some embodiments, respiratory disease or condition is asthma. The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause. In some embodiments, the type of asthma is allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, child-onset asthma, adult-onset asthma, cough-variant asthma, neutrophilic asthma, occupational asthma, steroid-resistant asthma, or seasonal asthma.

Asthma is a chronic inflammatory disorder of the airways in which many cells and cellular elements play a role. The chronic inflammation associated with airway hyperresponsiveness leads to recurrent episodes of wheezing, breathlessness, chest tightness, and coughing, particularly at night or in the early morning. These episodes are usually associated with widespread, but variable, airflow obstruction that is often reversible either spontaneously, or with treatment.

There are still significant medical needs in persistent, mild, moderate, and severe asthma. The control of asthma is not always achieved despite the step-wise approach to treatment. In the long-term, pulmonary function can be modified with the development of non-reversible obstruction. The evolution of the disease can be unpredictable, precipitating admission to the emergency room. The patients who are uncontrolled on inhaled or oral corticosteroids exhibit many of the following signs: symptoms at least twice weekly, limitations on activity, frequent nocturnal symptoms and awakenings, frequent use of a rescue inhaler, exacerbations up to once in a week, and reduced lung function (FEV1<80% predicted). There is a need for novel, oral controller medicine to provide new treatment options for patients with uncontrolled asthma.

Because of the mechanism of action of Compound 1 on allergic inflammation, Compound 1 is a therapeutic option for patients with allergic asthma who are not adequately controlled with current therapies. In some embodiments, a treatment effect is obtained in non-allergic asthma.

In one embodiments, Compound 1, or a pharmaceutically salt thereof (e.g. Compound 2), is used in the chronic treatment of persistent, uncontrolled asthma. Persistent, uncontrolled asthma is characterized as asthma that is not adequately controlled with current therapies (e.g. steroid resistant asthma).

In some embodiments, Compound 1, or a pharmaceutically salt thereof (e.g. Compound 2), is used in the treatment of allergic diseases or conditions.

Allergic diseases or conditions include, but are not limited to, ocular inflammation and conjunctivitis, vernal keratoconjunctivitis, papillary conjunctivitis, rhinitis, asthma, dermatitis.

In some embodiments, Compound 1, or a pharmaceutically salt thereof (e.g. Compound 2), is used in the treatment of ocular diseases or conditions. The term "ocular disease or condition" as used herein, refers to diseases or conditions which affect the eye or eyes and potentially the surrounding tissues as well. Ocular disease or condition includes, but is not limited to, ocular inflammation, conjunctivitis, retinitis, scleritis, uveitis, allergic conjuctivitis, vernal conjunctivitis, pappillary conjunctivitis, uveoretinitis.

In one aspect, the allergic disease or condition is rhinitis. The term "rhinitis" as used herein refers to any disorder of the nose in which there is inflammation of the mucous lining of the nose by whatever cause (intrinsic, extrinsic or both; allergic or non-allergic). In some embodiments, the rhinitis includes, but is not limited to, allergic (extrinsic) rhinitis, non-allergic (intrinsic) rhinitis, chronic rhinitis, allergen-induced rhinitis, aspirin-sensitive rhinitis, child-onset rhinitis, adult-onset rhinitis, occupational rhinitis, steroid-resistant rhinitis, seasonal rhinitis, perennial rhinitis, rhinosinusitis, and rhinopolyposis.

In one embodiment, Compound 1, or a pharmaceutically salt thereof (e.g. Compound 2), is used in the treatment of allergic rhinitis in a mammal.

In one embodiment, Compound 1, or a pharmaceutically salt thereof (e.g. Compound 2), is used in the treatment of type I hypersensitivity in a mammal. Type I hypersensitivity is an allergic reaction provoked by exposure to an allergen. Exposure may be by ingestion, inhalation, injection, or direct contact. Non-limiting examples of type I hypersensitivity include allergic asthma, allergic conjunctivitis, allergic rhinitis, anaphylaxis, angioedema, allergic dermatitis, urticaria, eosinophilia, penicillin allergy, cephalosporin allergy, food allergy.

In one embodiment, Compound 1, or a pharmaceutically salt thereof (e.g. Compound 2), is used in the treatment of skin disease. Skin disease includes but is not limited to eczema, psoriasis, pruritis, uticaria, pemphigus, allergic dermatitis, atopic dermatitis, neurodermatitis, exfoliative dermatitis, irritant dermatitis, seborrheic dermatitis, thermal induced dermatitis, drug induced dermatitis, atopic eczema, seborrhoeic dermatitis, dyshidrotic dermatitis (also known as Pompholyx), papular urticaria (a pattern of dermatitis often presenting after insect bite reactions), and hypersensitivity reactions Allergic dermatitis is typically a result of contact with external compounds, preservatives, fragrances, or plants.

In some embodiments, Compound 1, or a pharmaceutically salt thereof (e.g. Compound 2), is used in the treatment of chronic obstructive pulmonary disease. Chronic obstructive pulmonary disease includes, but is not limited to, chronic bronchitis and/or emphysema, pulmonary hypertension, interstitial lung fibrosis and/or airway inflammation and cystic fibrosis.

In one aspect, Compound 1, or a pharmaceutically acceptable salt thereof is used in the treatment of neutrophilic inflammation. Neutrophilic inflammation is involved in many inflammatory diseases or conditions. Neutrophilic inflammation is involved in many inflammatory diseases or conditions, such as respiratory diseases or conditions or allergic diseases or conditions.

In one aspect, assays described herein diagnose individuals as suitable candidates for therapy with $DP_2$ antagonist compounds. In one aspect, the individuals include those individuals with an inflammatory disease or condition. In one aspect, the inflammatory disease or condition is a respiratory disease or condition. In another aspect, the inflammatory disease or condition is an allergic disease or condition.

In some embodiments, Compound 1, or a pharmaceutically salt thereof (e.g. Compound 2), is used in the treatment of an inflammatory disease or condition in a mammal. "Inflammatory disease or condition" refers to those diseases or conditions that are characterized by one or more of the signs of pain, heat, redness, swelling, and loss of function (temporary or permanent). In one aspect, the inflammatory disease or condition is triggered by $PGD_2$.

Inflammation takes many forms and includes, but is not limited to, inflammation that is characterized by one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative.

Inflammatory diseases or conditions include those affecting the blood vessels (polyarteritis, temporal arteritis); joints (arthritis: crystalline, osteo-, psoriatic, reactive, rheumatoid, Reiter's); gastrointestinal tract (colitis); skin (dermatitis); organs (lungs, liver, pancreas); or multiple organs and tissues (systemic lupus erythematosus).

Inflammatory diseases or conditions include, but are not limited to, respiratory diseases or conditions, allergic diseases or conditions, psoriasis, inflammatory bowel disease, adult respiratory distress syndrome, myocardial infarction, congestive heart failure, stroke, arthritis, wound healing, endotoxic shock, cancer, pain, eosinophilic esophagitis, eosinophil-associated gastrointestinal disorders (EGID), idiopathic hypereosinophilic syndrome, otitis, airway constriction, mucus secretion, nasal congestion, increased microvascular permeability and recruitment of eosinophils, urticaria, sinusitis, uveitis, angioedema, anaphylaxia, chronic cough, Churg Strauss syndrome, rheumatoid arthritis, ankylosing spondylitis, osteoarthritis, lupus, graft versus host disease, tissue transplant rejection, ischemic conditions, epilepsy, Alzheimer's disease, Parkinson's disease, vitiligo, Wegener's granulomatosis, gout, eczema, dermatitis, coronary infarct damage, chronic inflammation, smooth muscle proliferation disorders, multiple sclerosis, and acute leukocyte-mediated lung injury. In some embodiments, inflammatory conditions are immune or anaphylactic disorders associated with infiltration of leukocytes into inflamed tissues or organs. In other embodiments, inflammatory conditions are associated with T-lymphocyte activation.

In some embodiments, Compound 1, or a pharmaceutically salt thereof (e.g. Compound 2), is used to desensitize the immune system of a mammal to one or more allergens responsible for an allergic disease or condition. Desensitizing the immune system to one or more allergens refers to the reduction in the atopic state of the patient. A reduction in the atopic state of the patient is achieved by, e.g. a reduction in the levels of cells reactive to allergen the body of the mammal.

In some embodiments, described herein is a method for preventing and/or treating eosinophil and/or basophil and/or dendritic cell and/or neutrophil and/or monocyte recruitment in comprising administering at least once to the mammal an effective amount of Compound 1, or a pharmaceutically acceptable salt thereof (e.g. Compound 2).

Described herein are compositions, pharmaceutical compositions, methods for treating, methods for formulating, methods for producing, methods for manufacturing, treatment strategies, pharmacokinetic strategies using Compound 1, or pharmaceutically acceptable salts thereof.

Compound 1, and Pharmaceutically Acceptable Salts Thereof

"Compound 1" or "[2'-(3-benzyl-1-ethyl-ureidomethyl)-6-methoxy-4'-trifluoromethyl-biphenyl-3-yl]-acetic acid" refers to the compound with the following structure:

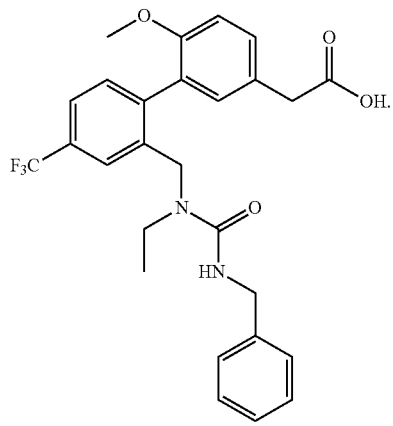 [SMILES: CCN(Cc1cc(C(F)(F)F)ccc1-c1cc(CC(=O)O)ccc1OC)C(=O)NCc1ccccc1]

Included within the scope of the term "Compound 1" are all pharmaceutically acceptable solvates (including hydrates), amorphous phases, partially crystalline and crystalline forms (including all polymorphs). In some embodiments, Compound 1 is amorphous, partially crystalline, crystalline, or mixtures thereof. In some embodiments, Compound 1 is amorphous. In some embodiments, Compound 1 is partially crystalline. In some embodiments, Compound 1 is crystalline.

Included within the scope of the term "pharmaceutically acceptable salt of Compound 1" are all pharmaceutically acceptable solvates (including hydrates), amorphous phases, partially crystalline and crystalline forms (including all polymorphs). In some embodiments, a pharmaceutically acceptable salt of Compound 1 is amorphous, partially crystalline, crystalline, or mixtures thereof. In some embodiments, a pharmaceutically acceptable salt of Compound 1 is amorphous. In some embodiments, a pharmaceutically acceptable salt of Compound 1 is partially crystalline. In some embodiments, a pharmaceutically acceptable salt of Compound 1 is crystalline.

"Compound 2" or "[2'-(3-benzyl-1-ethyl-ureidomethyl)-6-methoxy-4'-trifluoromethyl-biphenyl-3-yl]-acetic acid, sodium salt" or "sodium [2'-(3-benzyl-1-ethyl-ureidomethyl)-6-methoxy-4'-trifluoromethyl-biphenyl-3-yl]-acetate" refers to the compound with the following structure:

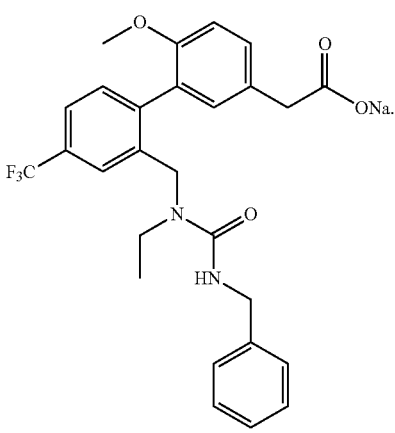

Included within the scope of the term "Compound 2" are all pharmaceutically acceptable solvates (including hydrates), amorphous phases, partially crystalline and crystalline forms (including all polymorphs). In some embodiments, Compound 2 is amorphous, partially crystalline, crystalline, or mixtures thereof. In some embodiments, Compound 2 is amorphous. In some embodiments, Compound 2 is partially crystalline. In some embodiments, Compound 2 is crystalline.

A wide variety of pharmaceutically acceptable salts are formed from Compound 1 and include:

salts formed when the acidic proton of the carboxylic acid of Compound 1 is replaced by a metal ion, such as for example, an alkali metal ion (e.g. lithium, sodium, potassium), an alkaline earth ion (e.g. magnesium, or calcium), or an aluminum ion, or is replaced by an ammonium cation ($NH_4^+$);

salts formed by reacting Compound 1 with a pharmaceutically acceptable organic base, which includes alkylamines, such as choline, ethanolamine, diethanolamine, triethanolamine, tromethamine, N-methylglucamine, dicyclohexylamine, tris(hydroxymethyl)methylamine, and salts with amino acids such as arginine, lysine, and the like.

In some embodiments, Compound 1 is treated with an amino acid to form a salt.

In other embodiments, Compound 1 is treated with choline, ethanolamine, diethanolamine, triethanolamine, tromethamine, N-methylglucamine, arginine, lysine, ammonium hydroxide, calcium hydroxide, potassium hydroxide, sodium carbonate, sodium hydroxide, and the like.

The term "pharmaceutically acceptable salt" in reference to Compound 1 refers to a salt of Compound 1, which does not cause significant irritation to a mammal to which it is administered and does not substantially abrogate the biological activity and properties of the compound.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methyl tert-butyl ether, isopropanol, acetonitrile, heptane, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005). Hydrates are formed when the solvent is water, or alcoholates are formed when the solvent is alcohol. In one embodiment, solvates of Compound 1, or salts thereof, are conveniently prepared or formed during the processes described herein. In addition, Compound 1, or salts thereof, exist in unsolvated form.

In yet other embodiments, Compound 1, or a pharmaceutically acceptable salt thereof (e.g. Compound 2) is prepared in various forms, including but not limited to, amorphous phase, milled forms and nano-particulate forms.

Amorphous Compound 1

In some embodiments, Compound 1 is amorphous. In some embodiments, Amorphous Phase of Compound 1 has an XRPD pattern showing a lack of crystallinity. In some embodiments, Amorphous Phase of Compound 1 exhibits an endotherm at 54° C., which corresponds to enthalpic relaxation as the material goes through its glass transition. In some embodiments, Amorphous Phase of Compound 1 is hygroscopic (from 0% to 90% relative humidity with a 1.7% weight change). Amorphous Phase of Compound 1 is chemically stable. Amorphous Phase of Compound 1 is sparingly soluble in water.

Amorphous Compound 2

In some embodiments, Compound 2 is amorphous. In some embodiments, Amorphous Phase of Compound 2 has an XRPD pattern showing a lack of crystallinity. In some embodiments, Amorphous Phase of Compound 2 does not exhibit any major endotherm as observed by differential scanning calorimetry (DSC); a glass transition is seen at about 100° C. In some embodiments, Amorphous Phase of Compound 2 is hygroscopic (from 0% to 90% relative humidity with a 36% weight change). Amorphous Phase of Compound 2 is chemically stable. Amorphous Phase of Compound 2 is soluble in water.

XRPD patterns are obtained in any manner, including by way of non-limiting example, (a) on a Siemens D5000 diffractometer; or (b) on a Bruker AXS C2 GADDS diffractometer. In specific embodiments, an XRPD pattern is obtained on a Siemens D5000 diffractometer using Cu Kα radiation (40 kV, 40 mA), 0-0 goniometer, divergence of V20 and receiving slits, a graphite secondary monochromator, and/or a scintillation counter. In another specific embodiment, an XRPD pattern is obtained on a Bruker AXS C2 GADDS diffractometer using Cu Kα radiation (40 kV, 40 mA), automated XYZ stage, laser video microscope for auto-sample positioning, a HiStar 2-dimensional area detector, a Göbel multilayer mirror coupled with a pinhole collimator of 0.3 mm, a beam divergence of approximately 4 mm, a 0-0 continuous scan mode, a sample detector distance of 20 cm, an effective 2θ range of 3.2°-29.7° and/or a sample exposure to the X-ray beam for about 120 seconds.

Prodrugs of Compound 1

In some embodiments, Compound 1 is prepared as a prodrug. A "prodrug of Compound 1" refers to a compound that is converted into Compound 1 in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, prodrugs facilitate transmittal across a cell membrane where water solubility is detrimental to mobility but which then is metabolically hydrolyzed to the carboxylic acid, the active entity, once inside the cell where water-solubility is beneficial. An example, without limitation, of a prodrug would be an ester of Compound 1 (the "prodrug").

A further example of a prodrug might be a short peptide (polyaminoacid) bonded to an acid group where the peptide is metabolized to reveal the active moiety.

Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. In certain embodiments, the prodrug of Compound 1 increases the bioavailability of Compound 1 when orally administered. In some embodiments, the prodrug of Compound 1 has improved solubility in pharmaceutical compositions over Compound 1.

In some embodiments, a prodrug of Compound 1 is an alkyl ester of Compound 1, such as, for example, methyl ester, ethyl ester, n-propyl ester, iso-propyl ester, n-butyl ester, sec-butyl ester, tert-butyl ester.

Non-limiting examples of prodrugs of Compound 1 include:

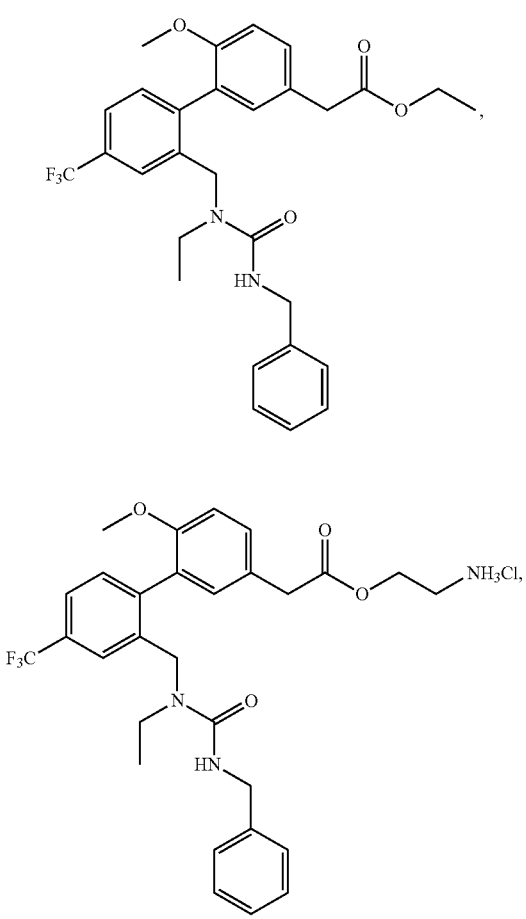

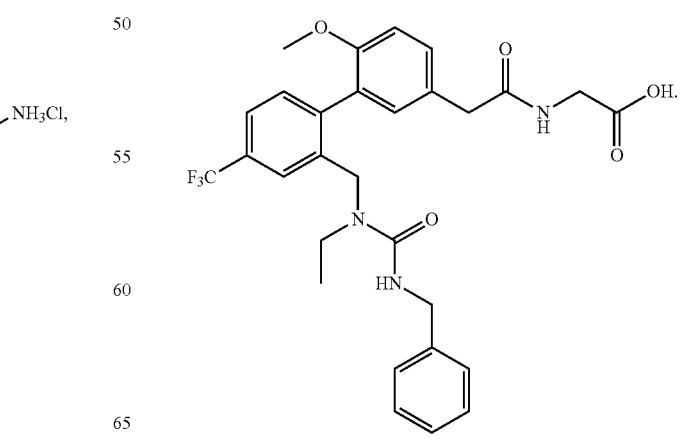

-continued

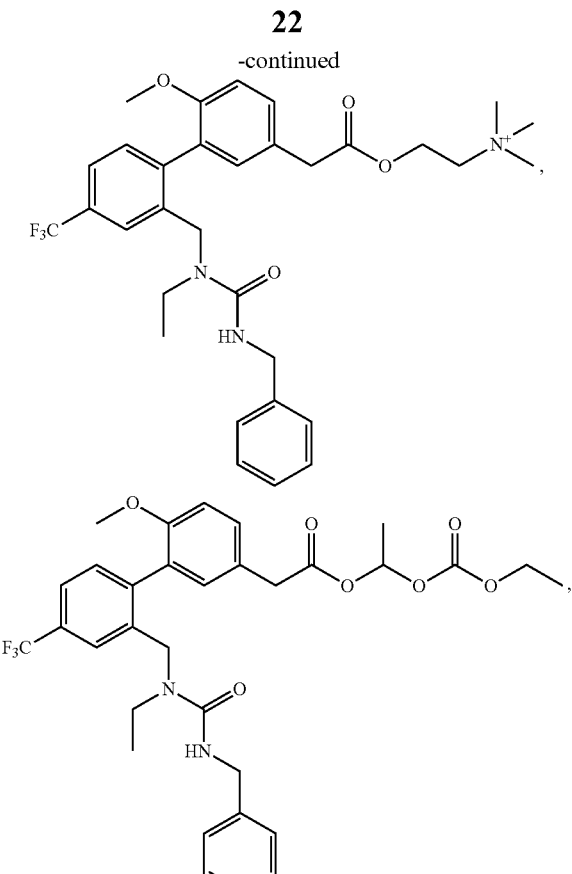

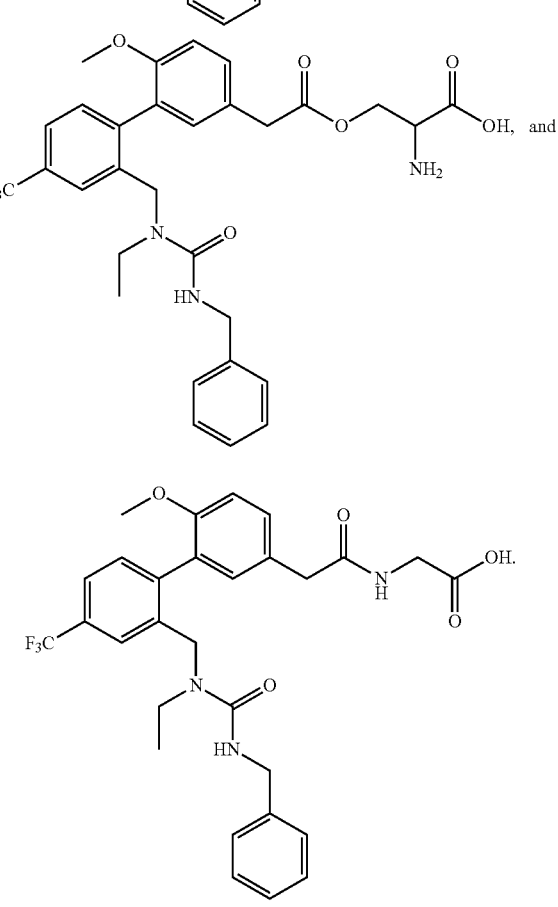

Metabolites of Compound 1

Compound 1 metabolites formed during incubation of Compound 1 with rat, dog, and human liver microsomes, rat and human hepatocytes, as well as those generated in vivo and isolated from rat bile and rat and dog plasma have been investigated. Authentic standards of the majority of the metabolites have been chemically synthesized. The identity of the in vitro and in vivo metabolites were confirmed by comparison with the authentic standard and/or by the fragmentation pattern observed following LC-MS/MS analysis. The major metabolites generated in vitro appear to be an acyl-glucuronide, de-benzylation, hydroxylation and N-de-ethylation. Following intravenous dosing of Compound 1, the major metabolites isolated from rat bile are an acyl-glucuronide, de-benzylation, N-de-ethylation, and O-de-methylation. In urine from these animals, the only metabolite found was the free amine. Metabolites circulating in rat plasma are the glucuronide, de-benzylation, and N-de-ethylation metabolites and all are greater than 10% of the parent AUC in rat. In dog plasma the major metabolites are the acyl-glucuronide and N-de-ethylation with both being greater than 10% parent AUC. All other metabolites in rat and dog plasmas appear to be 5% parent AUC.

In some embodiments, sites on Compound 1 are susceptible to various metabolic reactions. Therefore incorporation of appropriate substituents on Compound 1 will reduce, minimize or eliminate this metabolic pathway. In specific embodiments, the appropriate substituent to decrease or eliminate the susceptibility of the aromatic ring to metabolic reactions is, by way of example only, a halogen, deuterium or an alkyl group (e.g. methyl, ethyl).

In some embodiments, Compound 1 is isotopically labeled (e.g. with a radioisotope) or by another other means, including, but not limited to, the use of chromophores or fluorescent moieties, bioluminescent labels, or chemiluminescent labels. In some embodiments, Compound 1 is isotopically-labeled, which is identical to Compound 1 but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on Compound 1 are deuterated. In some embodiments, substitution with deuterium affords certain therapeutic advantages resulting from greater metabolic stability, such as, for example, increased in vivo half-life or reduced dosage requirements.

In one aspect, described is a compound with the following structure:

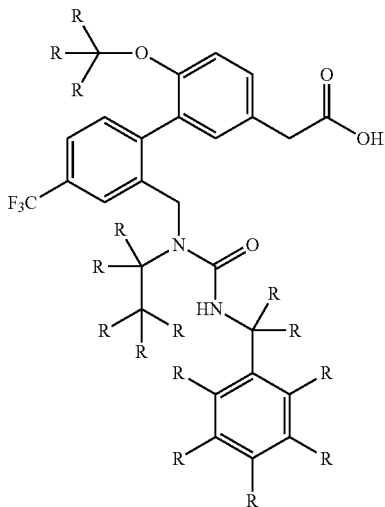

wherein, each R is independently selected from hydrogen or deuterium, or a pharmaceutically acceptable salt thereof.

In some embodiments, the pharmaceutically acceptable salt of the compound is a sodium salt.

Synthesis of Compound 1, and Pharmaceutically Acceptable Salts Thereof

Compounds 1, and pharmaceutically acceptable salts thereof, are synthesized as described herein. In additions, solvents, temperatures and other reaction conditions presented herein may vary.

Described herein are processes for the preparation of Compound 1, and pharmaceutically acceptable salts thereof (e.g. Compound 2).

In one aspect, Compound 1, or pharmaceutically acceptable salts thereof (e.g. sodium salt) are prepared as outlined in Scheme 1.

Scheme 1.

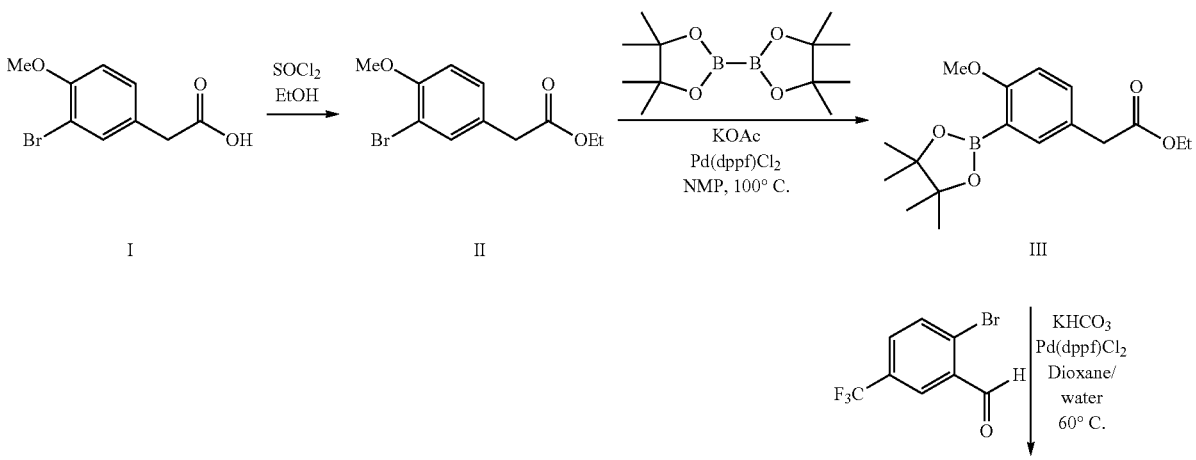

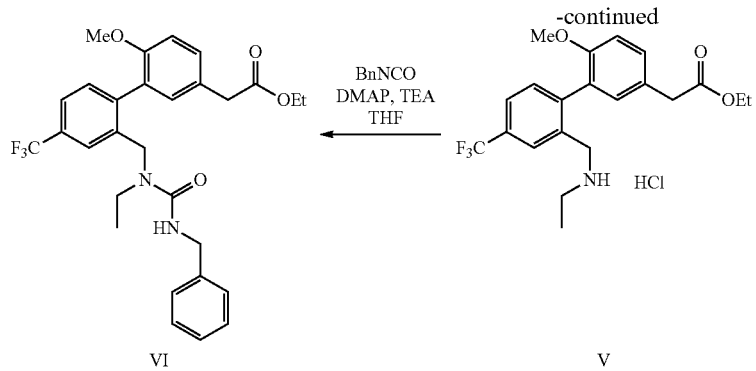

VI

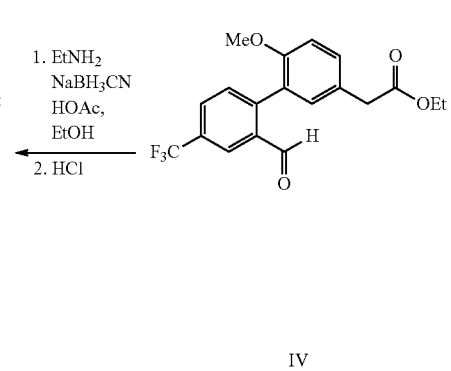

V

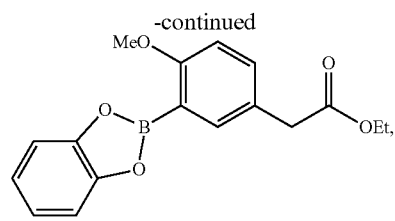

IV

Conversion of the bromide of compound II to a boronate ester or boronic acid, such as compound III, is achieved with bis(pinacolato)diboron, potassium acetate, and a metal catalyst. In some embodiments, the metal catalyst is a palladium catalyst. In one aspect, the palladium catalyst is Pd(dppf)Cl$_2$. Compound III may also be prepared by using alternative forms of compound II such as the iodo, the chloro or the triflate in place of the bromo. Compound III is then coupled with 2-bromo-5-(trifluoromethyl)benzaldehyde under Suzuki mediated coupling conditions to provide compound IV. In one aspect, the Suzuki mediated coupling conditions include an inorganic base and a palladium catalyst. In some embodiments, the Suzuki mediated coupling conditions include potassium bicarbonate and Pd(dppf)Cl$_2$. In some embodiments, the Suzuki mediated coupling conditions include potassium carbonate and tetrakis(triphenylphosphine)palladium.

Bases used in palladium mediated reactions include, but are not limited to, cesium carbonate, triethylamine, diisopropylethylamine, 1,2,2,6,6-pentamethylpiperidine, tributylamine, sodium carbonate, potassium carbonate, sodium acetate, potassium acetate, and potassium phosphate.

Bis(pinacolato)diboron can be replaced with other borylating agents to provide other boronic esters or boronic acids that are coupled with 2-bromo-5-(trifluoromethyl)benzaldehyde under Suzuki mediated coupling conditions to provide compound IV. Borylating reagents include, but are not limited to, pinacolborane, catecholborane, bis(neopentyl glycolato)diboron, bis(pinacolato)diboron, bis(hexylene glycolato)diboron, and bis(catecholato)diboron. Other coupling partners include in place of compound III include:

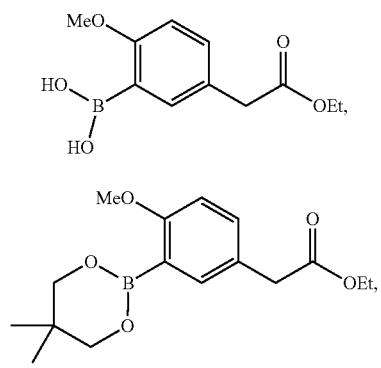

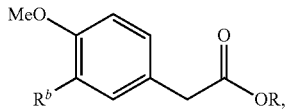

or any other suitable boronic acid or boronic ester with the general structure:

where R is a C$_1$-C$_4$ alkyl, and R$^b$ is a boronic acid or boronic ester.

Although the ethyl ester is shown in Scheme 1, other alkyl ester are contemplated. In some embodiments, the methanol is used instead of ethanol in the first step of Scheme 1 to provide the methyl ester. In some embodiments, the isopropanol is used in the first step of Scheme 1 to provide the isopropyl ester.

Other metal mediated coupling reactions to form biaryls include, but are not limited to Suzuki reactions, Stille cross couplings, Negishi couplings, Kumada couplings, Ullmann reactions, Hiyama Coupling, and variants thereof (Metal-Catalyzed Cross-Coupling Reactions, Armin de Meijere (Editor), François Diederich (Editor), John Wiley & Sons; 2nd edition, 2004; Özdemir, et al., *Tetrahedron*, 2005, 61, 9791-9798; Ackermann, et al., *Org. Lett.*, 2006, 8, 3457-3460; Blakey, et al., *J. Am. Chem. Soc.*, 2003, 125, 6046-6047; Dai, et al., *Org. Lett.*, 2004, 6, 221-224; Yoshikai, et al, *J. Am. Chem. Soc.*, 2005, 127, 17978-17979; Tang, et al, *J. Org. Chem.*, 2006, 71, 2167-2169; Murata, et al., *Synthesis*, 2001, 2231-2233).

In some embodiments, the synthesis of compound IV includes a purification step to reduce the amount of palladium in the product. Purification steps to reduce the amount of palladium in a product are conducted so that active pharmaceutical ingredients meet palladium specification guidelines. ("Guideline on the Specification Limits for Residues of Metal Catalysts" European Medicines Agency *Pre-authorisation Evaluation of Medicines for Human Use*, London, January 2007, Doc. Ref. CPMP/SWP/QWP/4446/00 corr.). In some embodiments, purification steps to reduce the amount of palladium in a product includes, but is not limited to, treatment with solid trimercaptotriazine (TMT), polystyrene-bound TMT, mercapto-porous polystyrene-bound TMT, polystyrene-bound ethylenediamine, activated carbon, glass bead sponges, Smopex™, silica bound scavengers, thiol-derivatized silica gel, N-acetylcysteine, n-Bu₃P, crystallization, extraction, 1-cysteine, n-Bu₃P/lactic acid. (Garrett et al., *Adv. Synth. Catal.* 2004, 346, 889-900). In some embodiments, activated carbon includes but is not limited to DARCO® KB-G, DARCO® KB-WJ. In one aspect silica bound scavengers include but are not limited to

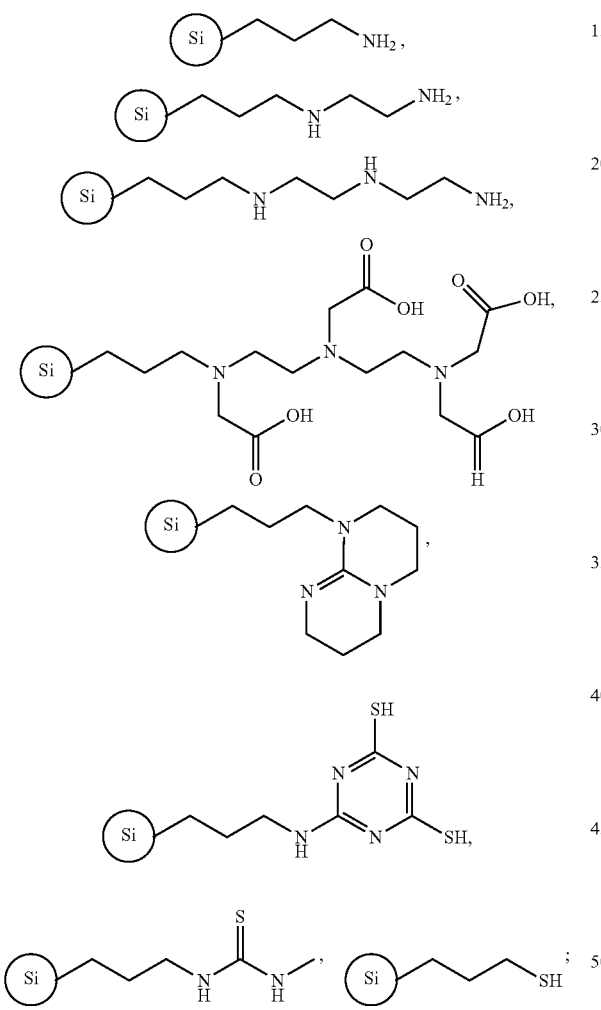

where denotes silica gel.

In some embodiments, compound IV is treated with activated carbon. In some embodiments, compound IV is treated with derivatized silica gel. In some embodiments, compound IV is treated with thiol derivatized silica gel.

In some embodiments, Compound VI is then hydrolyzed to provide Compound 1 as outlined in Scheme 2.

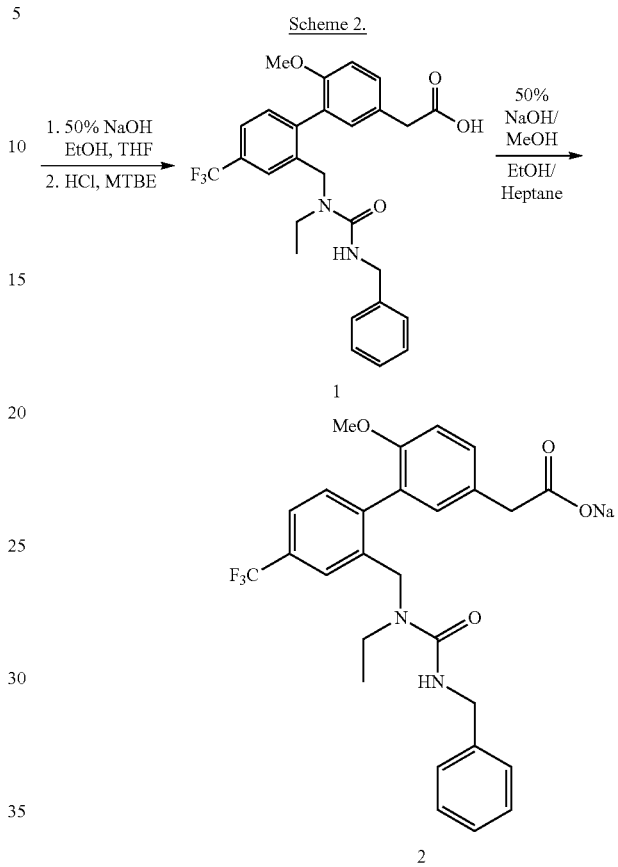

Hydrolysis of ester of structure VI with a suitable base in a suitable solvent yields compound 1 after pH adjustment. Suitable bases for the hydrolysis include, but are not limited to, lithium hydroxide and sodium hydroxide. Suitable solvents for the hydrolysis include, but are not limited to, water, methanol, ethanol, tetrahydrofuran, methyl tert-butyl ether, or combinations thereof. Compound 1 is then treated with sodium hydroxide to furnish Compound 2.

To ensure proper amorphous solids for Compound 2 and the removal of residual solvents to meet ICH residual solvent specifications, Compound 2 is isolated from a ethanol:heptane slurry.

In some embodiments, compound IV is prepared as outlined in Scheme 3.

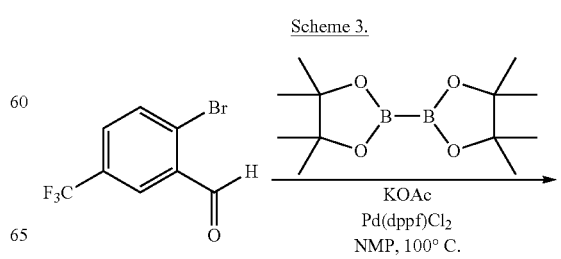

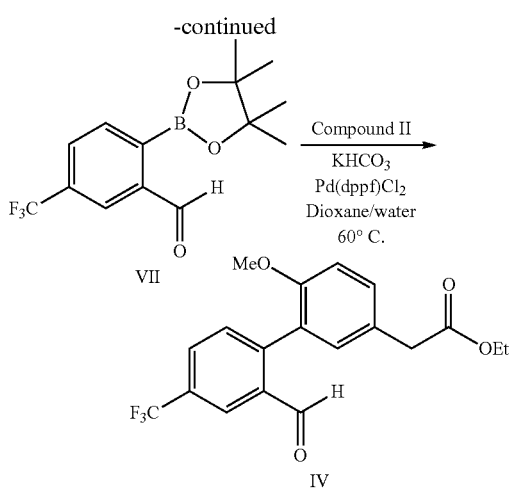

2-Bromo-5-(trifluoromethyl)benzaldehyde is reacted with a borylating agent under palladium mediated reaction conditions as described for Scheme 1 to provide compound VII. Other borylating agents are contemplated as described above for Scheme 1. Coupling of compound II with compound VII provides compound IV. Compound IV is the used in the synthesis of Compound 1 or Compound 2 as described above.

In some embodiments, compound VI is prepared as outlined in Scheme 4.

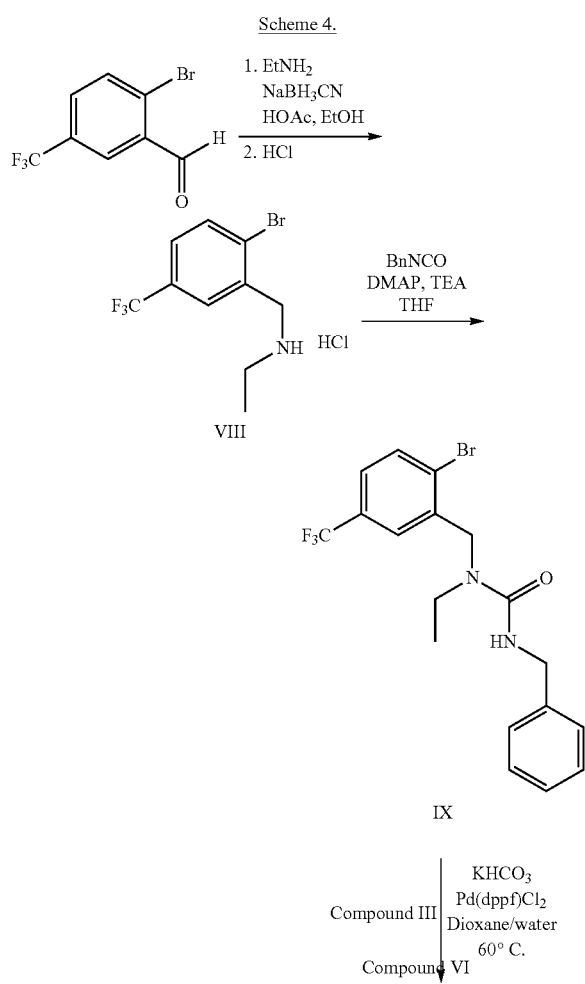

Reductive amination of 2-bromo-5-(trifluoromethyl)benzaldehyde provides compound VIII, which is then treated with benzylisocyanate to provide compound IX. Compound IX is then coupled with compound III under Suzuki reaction conditions. In some embodiments, other metal mediated reaction conditions are used to couple compound IX with compound III.

In some embodiments, compound VI is prepared as outlined in Scheme 5.

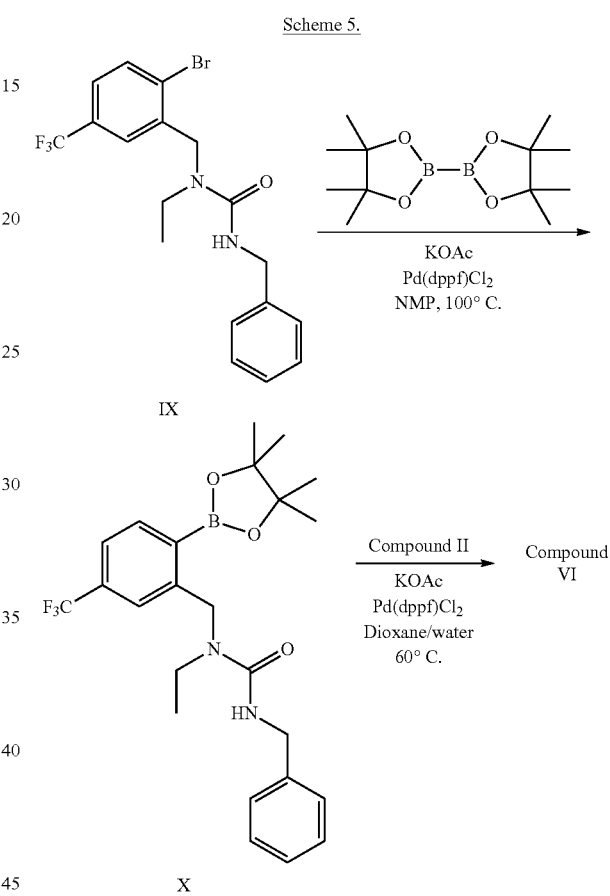

Compound IX is treated with a borylating agent in the presence of a palladium catalyst to provide compound X. Compound X is then coupled with compound II under Suzuki reaction conditions to provide compound VI. In some embodiments, other metal mediated reaction conditions are used to couple compound X with compound II to provide compound VI.

In some embodiments, Compound 1 is treated with potassium hydroxide in a solvent to form Compound 1, potassium salt. In some embodiments, Compound 1 is treated with lithium hydroxide in a solvent to form Compound 1, lithium salt. In some embodiments, Compound 1 is treated with calcium hydroxide in a solvent to form Compound 1, calcium salt.

In some embodiments, Compound 1 is treated with dicyclohexylamine in a solvent to form the corresponding salt. In some embodiments, Compound 1 is treated with N-methyl-D-glucamine in a solvent to form the corresponding salt. In some embodiments, Compound 1 is treated with choline in a solvent to form the corresponding salt. In some embodiments, Compound 1 is treated with tris(hydroxymethyl) methylamine in a solvent to form the corresponding salt.

In some embodiments, Compound 1 is treated with arginine in a solvent to form the corresponding salt. In some embodiments, Compound 1 is treated with lysine in a solvent to form the corresponding salt.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethane; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

Residual solvents in active pharmaceutical ingredients (APIs) originate from the manufacture of API. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising salts of Compound 1 comprise an organic solvent(s). In some embodiments, compositions comprising salts of Compound 1 comprise a residual amount of an organic solvent(s). In some embodiments, compositions comprising salts of Compound 1 comprise a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is selected from ethyl acetate, isopropyl acetate, tert-butylmethylether, heptane, isopropanol, and ethanol.

In some embodiments, the compositions comprising a salt of Compound 1 include a detectable amount of an organic solvent. In some embodiments, the salt of Compound 1 is a sodium salt (i.e. Compound 2). In some embodiments, the organic solvent is a Class 3 solvent.

In one aspect, the salt of Compound 1 is a sodium salt, potassium salt, lithium salt, calcium salt, magnesium salt, ammonium salt, choline salt, protonated dicyclohexylamine salt, protonated N-methyl-D-glucamine salt, protonated tris (hydroxymethyl)methylamine salt, arginine salt, or lysine salt. In one aspect, the salt of Compound 1 is a sodium salt.

In other embodiments are compositions comprising Compound 2, wherein the composition comprises a detectable amount of solvent that is less than about 1%, wherein the solvent is selected from 1,2-dimethoxyethane, acetonitrile, ethyl acetate, tetrahydrofuran, methanol, ethanol, heptane, and 2-propanol. In a further embodiment are compositions comprising Compound 2, wherein the composition comprises a detectable amount of solvent which is less than about 5000 ppm. In yet a further embodiment are compositions comprising Compound 2, wherein the detectable amount of solvent is less than about 5000 ppm, less than about 4000 ppm, less than about 3000 ppm, less than about 2000 ppm, less than about 1000 ppm, less than about 500 ppm, or less than about 100 ppm.

Certain Terms

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, organic synthesis, biochemistry, recombinant DNA techniques and pharmacology, within the skill of the art are employed. In this application, the use of "or" means "and/or" unless stated otherwise. Furthermore, use of the term "including" as well as other forms, such as "include", "includes," and "included," is not limiting.

The term "pharmaceutically acceptable excipient," as used herein, refers to a material, such as a carrier, diluent, stabilizer, dispersing agent, suspending agent, thickening agent, etc. which allows processing the active pharmaceutical ingredient (API) into a form suitable for administration to a mammal. In one aspect, the mammal is a human. Pharmaceutically acceptable excipients refer to materials which do not substantially abrogate the desired biological activity or desired properties of the compound (i.e. API), and is relatively nontoxic, i.e., the material is administered to an individual without causing undesirable biological effects or interacting in a deleterious manner with any of the components of the composition in which it is contained.

"Active pharmaceutical ingredient" or API refers to a compound that possesses a desired biological activity or desired properties. In some embodiments, an API is Compound 1. In some embodiments, an API is Compound 2. Provided herein is an active pharmaceutical ingredient (API), Compound 1, or pharmaceutically acceptable salt thereof (e.g. Compound 2), with a purity of greater than 80%, greater than 85%, greater than 90%, greater than 95%, greater than 96%, greater than 97%, greater than 98%, greater than 98%, or greater than 99%. In specific embodiments, provided herein is an active pharmaceutical ingredient (API), Compound 2, with a purity of greater than 80%, greater than 85%, greater than 90%, greater than 95%, greater than 96%, greater than 97%, greater than 98%, or greater than 99%.

The term "pharmaceutical combination" as used herein, means a product that results from the mixing or combining of more than one active ingredient and includes both fixed and non-fixed combinations of the active ingredients. The term "fixed combination" means that the active ingredients, e.g. Compound 1, and a co-agent, are both administered to a patient simultaneously in the form of a single entity or dosage. The term "non-fixed combination" means that the active ingredients, e.g. Compound 1, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of Compound 1, or pharmaceutically acceptable salt and/or solvate thereof, with other chemical components, such as carriers, stabilizers, diluents, dispersing agents, suspending agents, thickening agents, excipients, etc. The pharmaceutical composition facilitates administration of the compound to a mammal.

Administration of a combination of agents, as used herein, includes administration of the agents described in a single composition or in a combination therapy wherein one or more agent is administered separately from at least one other agent.

An "alkyl" group refers to an aliphatic hydrocarbon group. The alkyl moiety is branched, straight chain, or cyclic. The alkyl group may be designated as "$C_1$-$C_6$ alkyl". In one aspect, an alkyl is selected from methyl, ethyl, propyl, isopropyl, butyl, isobutyl, tert-butyl, pentyl, neopentyl, hexyl, ethenyl, propenyl, allyl, butenyl, cyclopropyl, cyclobutyl, cyclopentyl, cyclohexyl, and the like.

"Detectable amount" refers to an amount that is measurable using standard analytic methods (e.g. ion chromatography, mass spectrometry, NMR, HPLC, gas chromatography, elemental analysis, IR spectroscopy, inductively coupled plasma atomic emission spectrometry, USP<231>Method II, etc) (ICH guidances, *Q2A Text on Validation of Analytical Procedures* (March 1995) and *Q2B Validation of Analytical Procedures: Methodology* (November 1996)).

The term "acceptable" with respect to a formulation, composition or ingredient, as used herein, means having no persistent detrimental effect on the general health of the subject being treated.

The terms "effective amount" or "therapeutically effective amount," as used herein, refer to a sufficient amount of an agent being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. The term "therapeutically effective amount" includes, for example, a prophylactically effective amount. The effective amount will be selected based on the particular patient and the disease level. It is understood that "an effect amount" or "a therapeutically effective amount" varies from subject to subject, due to variation in metabolism of drug, age, weight, general condition of the subject, the condition being treated, the severity of the condition being treated, and the judgment of the prescribing physician. In one embodiment, an appropriate "effective" amount in any individual case is determined using techniques, such as a dose escalation study The terms "co-administration" or the like, as used herein, are meant to encompass administration of the selected therapeutic agents to a single patient, and are intended to include treatment regimens in which the agents are administered by the same or different route of administration or at the same or different time.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized (biotransformed). The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases (UGT) catalyze the transfer of an activated glucuronic-acid molecule to aromatic alcohols, aliphatic alcohols, carboxylic acids, amines and free sulphydryl groups (e.g. conjugation reactions). Further information on metabolism is available in The Pharmacological Basis of Therapeutics, 9th Edition, McGraw-Hill (1996). In one embodiment, metabolites of the compounds disclosed herein are identified either by administration of compounds to a host and analysis of tissue samples from the host, or by incubation of compounds with hepatic cells in vitro and analysis of the resulting compounds.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "agonist," as used herein, refers to a molecule such as a compound, a drug, an enzyme activator or a hormone modulator that binds to a specific receptor and triggers a response in the cell. An agonist mimics the action of an endogenous ligand (such as prostaglandin, hormone or neurotransmitter) that binds to the same receptor.

The term "antagonist," as used herein, refers to a molecule such as a compound, which diminishes, inhibits, or prevents the action of another molecule or the activity of a receptor site. Antagonists include, but are not limited to, competitive antagonists, non-competitive antagonists, uncompetitive antagonists, partial agonists and inverse agonists.

Competitive antagonists reversibly bind to receptors at the same binding site (active site) as the endogenous ligand or agonist, but without activating the receptor.

Non-competitive antagonists (also known as allosteric antagonists) bind to a distinctly separate binding site from the agonist, exerting their action to that receptor via the other binding site. Non-competitive antagonists do not compete with agonists for binding. The bound antagonists may result in a decreased affinity of an agonist for that receptor, or alternatively may prevent conformational changes in the receptor required for receptor activation after the agonist binds.

Uncompetitive antagonists differ from non-competitive antagonists in that they require receptor activation by an agonist before they can bind to a separate allosteric binding site.

Partial agonists are defined as drugs which, at a given receptor, might differ in the amplitude of the functional response that they elicit after maximal receptor occupancy. Although they are agonists, partial agonists can act as a competitive antagonist if co-administered with a full agonist, as it competes with the full agonist for receptor occupancy and producing a net decrease in the receptor activation observed with the full agonist alone.

An inverse agonist can have effects similar to an antagonist, but causes a distinct set of downstream biological responses. Constitutively active receptors which exhibit intrinsic or basal activity can have inverse agonists, which not only block the effects of binding agonists like a classical antagonist, but inhibit the basal activity of the receptor.

The term "subject" or "patient" encompasses mammals. In one aspect, the mammal is a human. In another aspect, the mammal is a non-human primate such as chimpanzee, and other apes and monkey species. In one aspect, the mammal is a farm animal such as cattle, horse, sheep, goat, or swine. In one aspect, the mammal is a domestic animal such as rabbit, dog, or cat. In one aspect, the mammal is a laboratory animal, including rodents, such as rats, mice and guinea pigs, and the like.

"Bioavailability" refers to the percentage of the weight of Compound 1, or a pharmaceutically acceptable salt and/or solvate thereof, dosed that is delivered into the general circulation of the animal or human being studied. The total exposure ($AUC_{(0-\infty)}$) of a drug when administered intravenously is usually defined as 100% Bioavailable (F %). "Oral bioavailability" refers to the extent to which Compound 1, or a pharmaceutically acceptable salt and/or solvate thereof, is absorbed into the general circulation when the pharmaceutical composition is taken orally as compared to intravenous injection.

"Blood plasma concentration" refers to the concentration Compound 1, in the plasma component of blood of a mammal. It is understood that the plasma concentration of Compound 1 may vary significantly between subjects, due to variability with respect to metabolism and/or interactions with other therapeutic agents. In one aspect, the blood plasma concentration of Compound 1 varies from subject to subject. Likewise, values such as maximum plasma concentration ($C_{max}$) or time to reach maximum plasma concentration ($T_{max}$), or total area under the plasma concentration time curve ($AUC_{(0-\infty)}$) vary from subject to subject. Due to this variability, in one embodiment, the amount necessary to constitute "a therapeutically effective amount" of Compound 1 varies from subject to subject.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

"Serum concentration" or "Plasma concentration" describes the blood serum or blood plasma concentration, typically measured in mg, μg, or ng of therapeutic agent per ml, dl, or l of blood serum, absorbed into the bloodstream after administration. Plasma concentrations are typically measured in ng/ml or μg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Steady state," as used herein, is when the amount of drug administered is equal to the amount of drug eliminated within one dosing interval resulting in a plateau or constant plasma drug exposure.

"Treat" or "treatment" as used herein refers to any treatment of a disorder or disease, such as preventing the disorder or disease from occurring in a subject predisposed to the disorder or disease, but has not yet been diagnosed as having the disorder or disease; inhibiting the disorder or disease, e.g., arresting the development of the disorder or disease, relieving the disorder or disease, causing regression of the disorder or disease, relieving a condition caused by the disease or disorder, or stopping the symptoms of the disease or disorder either prophylactically and/or therapeutically. Thus, as used herein, the term "treat" is used synonymously with the term "prevent."

Pharmaceutical Compositions/Formulations

Pharmaceutical compositions are formulated in a conventional manner using one or more physiologically acceptable carriers comprising excipients and auxiliaries which facilitate processing of the active compounds into preparations which are used pharmaceutically. Suitable techniques, carriers, and excipients include those found within, for example, *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

For oral administration, Compound 1, or a pharmaceutically acceptably salt thereof (e.g. Compound 2), are formulated by combining the active compound with pharmaceutically acceptable carriers or excipients. Such carriers enable Compound 1, or a pharmaceutically acceptably salt thereof (e.g. Compound 2) to be formulated as tablets, powders, pills, dragees, capsules, liquids, gels, syrups, elixirs, slurries, suspensions and the like, for oral ingestion by a patient to be treated.

The pharmaceutical compositions will include at least one pharmaceutically acceptable carrier, diluent or excipient and Compound 1 as an active ingredient in free-acid or free-base form, or in a pharmaceutically acceptable salt form.

The pharmaceutical compositions described herein include Compound 1, or a pharmaceutically acceptable salt thereof (e.g. Compound 2). In some embodiments, the pharmaceutical compositions described herein include Compound 1. In some embodiments, the pharmaceutical compositions described herein include amorphous Compound 1. In some embodiments, the pharmaceutical compositions described herein include Compound 2. In some embodiments, the pharmaceutical compositions described herein include amorphous Compound 2.

The pharmaceutical compositions described herein include: (a) Compound 1, or a pharmaceutically acceptable salt thereof (e.g. Compound 2); and one or more of the following: (b) binders; (c) disintegrants; (d) fillers (diluents); (e) lubricants; (f) glidants (flow enhancers); (g) compression aids; (h) colors; (i) sweeteners; (j) preservatives; (k) suspensing/dispersing agents; (l) film formers/coatings; (m) flavors; (o) printing inks; (p) solubilizers; (q) alkalizing agents; (r) buffering agents; (s) antioxidants; (t) effervescent agents.

In some embodiments, pharmaceutical compositions described herein include one or more of the following in addition to Compound 1, or a pharmaceutically acceptable salt thereof (e.g. Compound 2): (a) magnesium stearate; (b) lactose; (c) microcrystalline cellulose; (d) silicified microcrystalline cellulose; (e) mannitol; (f) starch (corn); (g) silicon dioxide; (h) titanium dioxide; (i) stearic acid; (j) sodium starch glycolate; (k) gelatin; (l) talc; (m) sucrose; (n) aspartame; (o) calcium stearate; (p) povidone; (q) pregelatinized starch; (r) hydroxy propyl methylcellulose; (s) OPA products (coatings & inks); (t) croscarmellose; (u) hydroxy propyl cellulose; (v) ethylcellulose; (w) calcium phosphate (dibasic); (x) crospovidone; (y) shellac (and glaze); (z) sodium carbonate.

In one embodiment, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, silicified microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate.

In one embodiment, the pharmaceutical compositions described herein are formulated into any suitable dosage form, including but not limited to, aqueous oral dispersions, solid oral dosage forms, fast melt formulations, effervescent formulations, lyophilized formulations, tablets, capsules, controlled release formulations, enteric coated tablets, inhaled powder, inhaled dispersion, IV formulations.

In further embodiments, the pharmaceutical compositions provided herein may be provided as compressed tablets, tablet triturates, rapidly dissolving tablets, multiple compressed tablets, or enteric-coated tablets, sugar-coated, or film-coated tablets.

Pharmaceutical dosage forms can be formulated in a variety of methods and can provide a variety of drug release profiles, including immediate release, sustained release, and delayed release. In some cases it may be desirable to prevent drug release after drug administration until a certain amount of time has passed (i.e. timed release), to provide substantially continuous release over a predetermined time period (i.e. sustained release) or to provide release immediately following drug administration (i.e., immediate release).

In some embodiments, formulations provide a therapeutically effective amount of Compound 1, or a pharmaceutically acceptable salt thereof (e.g. Compound 2), enabling, for example, once a week, twice a week, three times a week, four times a week, five times a week, once every other day, once-a-day, twice-a-day (b.i.d.), or three times a day (t.i.d.) administration if desired. In one embodiment, the formulation provides a therapeutically effective amount of Compound 1, or a pharmaceutically acceptable salt thereof (e.g. Compound 2) enabling once-a-day administration.

In one embodiment, Compound 1, or a pharmaceutically acceptable salt thereof (e.g. Compound 2) is formulated into an immediate release form that provides for once-a-day administration. Generally speaking, one will desire to administer an amount of Compound 1, or a pharmaceutically acceptable salt thereof (e.g. Compound 2) that is effective to achieve a plasma level commensurate with the concentrations found to be effective in vivo for a period of time effective to elicit a therapeutic effect.

In some embodiments, Compound 1, or a pharmaceutically acceptable salt thereof (e.g. Compound 2) and one or more excipients are dry blended and compressed into a mass, such as a tablet, having a hardness sufficient to provide a pharmaceutical composition that substantially disintegrates within less than about 10 minutes, less than about 15 minutes, less than about 20 minutes, less than about 25 minutes, less than about 30 minutes, less than about 35 minutes, or less than about 40 minutes, after oral administration, thereby releasing the Compound 1, or a pharmaceutically acceptable salt thereof (e.g. Compound 2) formulation into the gastrointestinal fluid.

In some embodiments, the pharmaceutical compositions provided herein in an immediate release dosage form are capable of releasing not less than 75% of the therapeutically active ingredient or combination and/or meet the disintegration or dissolution requirements for immediate release tablets of the particular therapeutic agents or combination included in the tablet core, as set forth in USP XXII, 1990 (The United States Pharmacopeia.). Immediate release pharmaceutical compositions include capsules, tablets, oral solutions, powders, beads, pellets, particles, and the like.

Excipients used in pharmaceutical compositions should be selected on the basis of compatibility with Compound 1, or a pharmaceutically acceptable salt thereof (e.g. Compound 2) and the release profile properties of the desired dosage form. Exemplary excipients include, e.g., binders, suspending agents, disintegration agents, filling agents, surfactants, solubilizers, stabilizers, lubricants, wetting agents, diluents, and the like.

Binders impart cohesiveness to solid oral dosage form formulations: for powder filled capsule formulation, they aid in plug formation that is filled into soft or hard shell capsules and for tablet formulation, they ensure the tablet remaining intact after compression and help assure blend uniformity prior to a compression or fill step.

In some embodiments, solid oral dosage forms include up to 40% of binder. In some embodiments, the binder(s) are selected from starches, sugars, povidone, cellulose or modified cellulose such as microcrystalline cellulose, hydroxypropyl methyl cellulose, lactose, or sugar alcohols like xylitol, sorbitol or maltitol. In some embodiments, the binder is hydroxypropyl methyl cellulose. In some embodiments, the binder is hypromellose (e.g., Methocel E5).

In general, binder levels of 20-70% are used in powder-filled gelatin capsule formulations. Binder usage level in tablet formulations varies whether direct compression, wet granulation, roller compaction, or usage of other excipients such as fillers which itself acts as moderate binder.

Dispersing agents, and/or viscosity modulating agents include materials that control the diffusion and homogeneity of a drug through liquid media or a granulation method or blend method. In some embodiments, these agents also facilitate the effectiveness of a coating or eroding matrix.

Diluents increase bulk of the composition to facilitate compression or create sufficient bulk for homogenous blend for capsule filling.

The term "disintegrate" includes both the dissolution and dispersion of the dosage form when contacted with gastrointestinal fluid. "Disintegration agents or disintegrants" facilitate the breakup or disintegration of a substance. In some embodiments, one aspect, solid oral dosage forms include up to 15% w/w of disintegrant. In some embodiments, the disintegrant is croscarmellose sodium. In another aspect, the disintegrant is sodium starch glycolate or crospovidone.

Filling agents include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

In one aspect, the filler is lactose (e.g. monohydrate). In another aspect, the filler is mannitol, or dicalcium phosphate. In another aspect, the filler is mannitol, microcrystalline cellulose, dicalcium phosphate or sorbitol.

Gastrointestinal fluid is the fluid of stomach secretions of a subject or the saliva of a subject after oral administration of a composition described herein, or the equivalent thereof. An "equivalent of stomach secretion" includes, e.g., an in vitro fluid having similar content and/or pH as stomach secretions such as a 1% sodium dodecyl sulfate solution or 0.1N HCl solution in water. In addition, simulated intestinal fluid (USP) is an aqueous phosphate buffer system at pH 6.8.

Lubricants and glidants are compounds that prevent, reduce or inhibit adhesion or friction of materials. In one aspect, solid oral dosage forms include about 0.25% w/w to about 2.5% w/w of lubricant. In another aspect solid oral dosage forms include about 0.5% w/w to about 1.5% w/w of lubricant.

In some embodiments, the solid dosage forms described herein are in the form of a tablet, (including an immediate release tablet, an extended release tablet, a sustained release tablet, a enteric coated tablet, a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, multiparticulate dosage forms, pellets, or granules.

In other embodiments, the pharmaceutical formulation is in the form of a powder. In still other embodiments, the pharmaceutical formulation is in the form of a tablet, including but not limited to, an immediate release tablet. Additionally, pharmaceutical formulations described herein are administered as a single dosage or in multiple dosages. In some embodiments, the pharmaceutical formulation is administered in two, or three, or four tablets.

In some embodiments, solid dosage forms, e.g., tablets, effervescent tablets, and capsules, are prepared by mixing Compound 1, or a pharmaceutically acceptable salt thereof (e.g. Compound 2) with one or more pharmaceutical excipients to form a bulk blend composition. When referring to these bulk blend compositions as homogeneous, it is meant that the Compound 1, or a pharmaceutically acceptable salt thereof (e.g. Compound 2) particles are dispersed evenly throughout the composition so that the composition is capable of being readily subdivided into equally effective unit dosage forms, such as tablets, pills, or capsules. In one embodiment, the individual unit dosages also include film coatings, which disintegrate upon oral ingestion or upon contact with diluent. In one embodiment, these formulations are manufactured by conventional techniques.

Conventional techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

Compressed tablets are solid dosage forms prepared by compacting the bulk blend formulations described above. In various embodiments, compressed tablets which are designed to dissolve in the mouth will include one or more flavoring agents. In other embodiments, the compressed tablets will include a film surrounding the final compressed tablet. In some embodiments, the film coating aids in patient compliance (e.g., Opadry® coatings or sugar coating). Film coatings comprising Opadry® typically range from about 1% to about 5% of the tablet weight. In other embodiments, the compressed tablets include one or more excipients.

Provided herein are pharmaceutical compositions in film-coated dosage forms, which comprise a combination of an active ingredient, or a pharmaceutically acceptable salt, solvate, or prodrug thereof; and one or more tabletting excipients to form a tablet core using conventional tabletting processes and subsequently coating the core. The tablet cores can be produced using conventional granulation methods, for example wet or dry granulation, with optional comminution of the granules and with subsequent compression and coating.

Further provided herein are pharmaceutical compositions in enteric coated dosage forms, which comprise a combination of an active ingredient, or a pharmaceutically acceptable salt, solvate, or prodrug thereof; and one or more release controlling excipients for use in an enteric coated dosage form. The pharmaceutical compositions also comprise non-release controlling excipients.

Enteric-coatings are coatings that resist the action of stomach acid but dissolve or disintegrate in the intestine.

In one aspect, the oral solid dosage form disclosed herein include an enteric coating(s). Enteric coatings include one or more of the following: cellulose acetate phthalate; methyl acrylate-methacrylic acid copolymers; cellulose acetate succinate; hydroxy propyl methyl cellulose phthalate; hydroxy propyl methyl cellulose acetate succinate (hypromellose acetate succinate); polyvinyl acetate phthalate (PVAP); methyl methacrylate-methacrylic acid copolymers; methacrylic acid copolymers, cellulose acetate (and its succinate and phthalate version); styrol maleic acid co-polymers; polymethacrylic acid/acrylic acid copolymer; hydroxyethyl ethyl cellulose phthalate; hydroxypropyl methyl cellulose acetate succinate; cellulose acetate tetrahydrophtalate; acrylic resin; shellac.

An enteric coating is a coating put on a tablet, pill, capsule, pellet, bead, granule, particle, etc. so that it doesn't dissolve until it reaches the small intestine.

Sugar-coated tablets are compressed tablets surrounded by a sugar coating, which may be beneficial in covering up objectionable tastes or odors and in protecting the tablets from oxidation.

Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets. In some embodiments, tablets are coated with water soluble, pH independent film coating which allows for immediate disintegration for fast, active release (e.g. Opadry products).

In some embodiments, the pharmaceutical compositions provided herein are in the form of a controlled release dosage form. As used herein, the term "controlled release" refers to a dosage form in which the rate or place of release of the active ingredient(s) is different from that of an immediate dosage form when orally administered. Controlled release dosage forms include delayed-, extended-, prolonged-, sustained-, pulsatile-, modified-, targeted-, programmed-release. The pharmaceutical compositions in controlled release dosage forms are prepared using a variety of modified release devices and methods including, but not limited to, matrix controlled release devices, osmotic controlled release devices, multiparticulate controlled release devices, ion-exchange resins, enteric coatings, multilayered coatings, and combinations thereof. The release rate of the active ingredient(s) can also be modified by varying the particle sizes.

In contrast to immediate release compositions, controlled release compositions allow delivery of an agent to a human over an extended period of time according to a predetermined profile. Such release rates can provide therapeutically effective levels of agent for an extended period of time and thereby provide a longer period of pharmacologic response. Such longer periods of response provide for many inherent benefits that are not achieved with the corresponding immediate release preparations. In one aspect, controlled release compositions of Compound 1, or a pharmaceutically acceptable salt thereof, provide therapeutically effective levels of Compound 1 for an extended period of time and thereby provide a longer period of pharmacologic response.

Delayed release as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above.

In some embodiments, the pharmaceutical compositions provided herein is in a modified release dosage form that is fabricated using a matrix controlled release device (see, Takada et al in "Encyclopedia of Controlled Drug Delivery," Vol. 2, Mathiowitz ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

In some embodiments, a matrix controlled release system includes an enteric coating so that no drug is released in the stomach.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include bottles of tablets or capsules.

In other embodiments a powder comprising the Compound 1, or a pharmaceutically acceptable salt thereof (e.g. Compound 2) formulations described herein are formulated to include one or more pharmaceutical excipients and flavors. Such a powder is prepared, for example, by mixing the Compound 1, or a pharmaceutically acceptable salt thereof (e.g. Compound 2) formulation and optional pharmaceutical excipients to form a bulk blend composition. Additional embodiments also comprise a suspending agent and/or a wetting agent. This bulk blend is uniformly subdivided into unit dosage packaging or multi-dosage packaging units. The term "uniform" means the homogeneity of the bulk blend is substantially maintained during the packaging process.

In still other embodiments, effervescent powders are prepared. Effervescent salts have been used to disperse medicines in water for oral administration. Effervescent salts are granules or coarse powders containing a medicinal agent in a dry mixture, usually composed of sodium bicarbonate, citric acid and/or tartaric acid.

The method of preparation of the effervescent granules described herein employs three basic processes: wet granulation, dry granulation and fusion. The fusion method is used for the preparation of most commercial effervescent powders. It should be noted that, although these methods are intended for the preparation of granules, the formulations of effervescent salts described herein, in one embodiment, are also prepared as tablets, according to technology for tablet preparation.

Wet granulation is one method of granule preparation. The individual steps in the wet granulation process of tablet preparation include milling and sieving of the ingredients, dry powder mixing, wet massing, granulation, drying and final grinding. In various embodiments, the composition is added to the other excipients of the pharmaceutical formulation after they have been wet granulated.

Dry granulation involves compressing a powder mixture into a rough tablet or "slug" on a heavy-duty rotary tablet press. The slugs are then broken up into granular particles by a grinding operation, usually by passage through an oscillation granulator. The individual steps include mixing of the powders, compressing (slugging) and grinding (slug reduction or granulation). No wet binder or moisture is involved in any of the steps. In some embodiments, the formulation is dry granulated with other excipients in the pharmaceutical formulation. In other embodiments, the formulation is added to other excipients of the pharmaceutical formulation after they have been dry granulated.

In one embodiment, pharmaceutical preparations which are used orally include push-fit capsules made of gelatin, as well as soft, sealed capsules made of gelatin and a plasticizer, such as glycerol or sorbitol. In one embodiment, the push-fit capsules contain the active ingredients in admixture with filler such as lactose, binders such as starches, and/or lubricants such as talc or magnesium stearate and, optionally, stabilizers. In one embodiment, in soft capsules, the active compounds are dissolved or suspended in suitable liquids, such as fatty oils, liquid paraffin, or liquid polyethylene glycols. In addition, in one embodiment, stabilizers are added. In other embodiments, the formulation is placed in a sprinkle capsule, wherein the capsule is swallowed whole or the capsule is opened and the contents sprinkled on food prior to eating.

All formulations for oral administration should be in dosages suitable for such administration.

In some embodiments, pharmaceutical formulations are provided comprising Compound 1, or a pharmaceutically acceptable salt thereof (e.g. Compound 2) and at least one dispersing agent or suspending agent for oral administration to a subject. In one embodiment, the formulation is a powder and/or granules for suspension, and upon admixture with water, a substantially uniform suspension is obtained.

A suspension is "substantially uniform" when it is mostly homogenous, that is, when the suspension is composed of approximately the same concentration of Compound 1, or a pharmaceutically acceptable salt thereof (e.g. Compound 2) at any point throughout the suspension (USP Chapter 905).

Liquid formulation dosage forms for oral administration are aqueous suspensions or non-aqueous suspensions.

Liquid formulation dosage forms for oral administration are aqueous suspensions selected from, but not limited to, pharmaceutically acceptable aqueous oral dispersions, emulsions, solutions, and syrups. See, e.g., Singh et al., *Encyclopedia of Pharmaceutical Technology*, $2^{nd}$ Ed., pp. 754-757 (2002). In addition to including Compound 1, or a pharmaceutically acceptable salt thereof (e.g. Compound 2), the liquid dosage forms include additives, such as: (a) disintegrating agents; (b) dispersing agents; (c) wetting agents; (d) preservatives; (e) viscosity enhancing agents; (f) sweetening agents; (g) flavoring agents; (h) solibizing agents (bioavailability enhancers).

In one embodiment, the aqueous suspensions and dispersions described herein remain in a homogenous state, as defined above by USP Chapter 905, for at least 4 hours. The homogeneity should be determined by a sampling method consistent with regard to determining homogeneity of the entire composition. In one embodiment, an aqueous suspension is re-suspended into a homogenous suspension by physical agitation lasting less than 1 minute. In another embodiment, an aqueous suspension is re-suspended into a homogenous suspension by physical agitation lasting less than 45 seconds. In yet another embodiment, an aqueous suspension is re-suspended into a homogenous suspension by physical agitation lasting less than 30 seconds. In still another embodiment, no agitation is necessary to maintain a homogeneous aqueous dispersion.

Liquid compositions illustratively take the form of a liquid where the agent (e.g. Compound 1, or a pharmaceutically acceptable salt thereof (e.g. Compound 2)) is present in solution, in suspension or both. In one embodiment, the liquid composition is aqueous.

Liquid compositions illustratively take the form of a liquid where the agent (e.g. Compound 1, or a pharmaceutically acceptable salt thereof (e.g. Compound 2)) is present in solution, in suspension or both. In one embodiment, the liquid composition is non-aqueous.

In one embodiment, the aqueous suspension also contains one or more polymers as suspending agents. Useful polymers include water-soluble polymers such as cellulosic polymers, e.g., hydroxypropyl methylcellulose, and water-insoluble polymers such as cross-linked carboxyl-containing polymers. In one embodiment, useful compositions also comprise an mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

In one embodiment, pharmaceutical compositions also include one or more pH adjusting agents or buffering agents, including acids such as acetic, boric, citric, lactic, phosphoric and hydrochloric acids; bases such as sodium hydroxide, sodium phosphate, sodium borate, sodium carbonate, sodium citrate, sodium acetate, sodium lactate and tris-hydroxymethylaminomethane; and buffers such as citrate/dextrose, sodium carbonate, sodium bicarbonate and ammonium chloride. Such acids, bases and buffers are included in an amount required to maintain pH of the composition in an acceptable range.

In one embodiment, liquid pharmaceutical compositions also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In one embodiment, pharmaceutical compositions also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other compositions include one or more antioxidants to enhance chemical stability where required. Suitable antioxidants include, by way of example only, ascorbic acid, tocopherol, and sodium metabisulfite.

In one embodiment, aqueous compositions are packaged in single-dose non-reclosable containers. Alternatively, multiple-dose reclosable containers are used, in which case it is typical to include a preservative in the composition.

In some embodiments, aqueous pharmaceutical compositions do not include a preservative and are used within 24 hours of preparation.

In some embodiments, aqueous pharmaceutical compositions include one or more solubilizers which aid in enhancing the bioavailability of the active pharmaceutical ingredient. In some embodiments, the solubilizer is selected from Labrasol, Lutrol (macrogels, poloxamers), and others known in the art.

The oral pharmaceutical solutions described herein are beneficial for the administration to infants (less than 2 years old), children under 10 years of age and any patient group that is unable to swallow or ingest solid oral dosage forms.

For buccal or sublingual administration, in one embodiment, the compositions take the form of tablets, lozenges, or gels formulated in a conventional manner (see e.g. U.S. Pat. Nos. 4,229,447, 4,596,795, 4,755,386, and 5,739,136).

In one embodiment, dragee cores are prepared with suitable coatings. For this purpose, concentrated sugar solutions are used, which optionally contain gum arabic, talc, polyvinylpyrrolidone, carbopol gel, polyethylene glycol, and/or titanium dioxide, lacquer solutions, and suitable organic solvents or solvent mixtures. In one embodiment, dyestuffs or pigments are added to the tablets or dragee coatings for identification or to characterize different combinations of active compound doses.

It should be understood that many carriers and excipients may serve several functions, even within the same formulation.

Dose Amounts of Compound 1 or a Pharmaceutically Acceptable Salt Thereof (e.g. Compound 2)

In certain embodiments, the effective amount of Compound 1, or a pharmaceutically acceptable salt thereof (e.g. Compound 2) is about 0.3 mg to about 1 g per dose, about 1 mg to about 1 g per dose, about 3 mg to about 600 mg per dose or about 3 mg to about 300 mg per dose. In some embodiments, the effective amount of Compound 1, or a pharmaceutically acceptable salt thereof (e.g. Compound 2) is about 1 mg to about 5 g per day, about 10 mg to about 2 g per day, about 10 mg to about 1 g per day, about 10 mg to about 0.6 g per day, about 10 mg to about 0.5 g per day, or about 10 mg to about 0.4 g per day.

In one embodiment, the effective amount of Compound 1, or a pharmaceutically acceptable salt thereof (e.g. Compound 2) is about 1 mg per dose, about 5 mg per dose, about 10 mg per dose, about 15 mg per dose, about 30 mg per dose, about 45 mg per dose, about 60 mg per dose, about 100 mg per dose, about 150 mg per dose, about 200 mg per dose, about 300 mg per dose, or about 600 mg per dose.

In some embodiments, oral pharmaceutical solutions include about 0.015 mg/ml to about 20 mg/ml of Compound 2. In some embodiments, oral pharmaceutical solutions include about 1 mg/ml to about 10 mg/ml of Compound 2.

In one aspect, immediate release tablets include about 5% w/w to about 50% w/w of Compound 1, or a pharmaceutically acceptable salt thereof (e.g. Compound 2). In some embodiments, immediate release tablets include about 5% w/w to about 40% w/w, or about 5% w/w to about 30% w/w of Compound 1, or a pharmaceutically acceptable salt thereof (e.g. Compound 2). In some embodiments, immediate release tablets include about 5% w/w, about 10% w/w, about 15% w/w, about 20% w/w, about 25% w/w, about 30% w/w, about 33% w/w, about 35% w/w, about 40% w/w of Compound 1, or a pharmaceutically acceptable salt thereof (e.g. Compound 2).

In one aspect, immediate release capsules include about 1.25% w/w to about 50% w/w of Compound 1, or a pharmaceutically acceptable salt thereof (e.g. Compound 2). In some embodiments, immediate release capsules include about 5% w/w to about 40% w/w, about 10% w/w to about 30% w/w, of Compound 1, or a pharmaceutically acceptable salt thereof (e.g. Compound 2). In some embodiments, immediate release capsules include about 5% w/w, about 10% w/w, about 15% w/w, about 20% w/w, about 25% w/w, or about 30% w/w of Compound 1, or a pharmaceutically acceptable salt thereof (e.g. Compound 2).

Methods of Dosing and Treatment Regimens

In one embodiment, the pharmaceutical compositions including Compound 1, or a pharmaceutically acceptable salt thereof (e.g. Compound 2), described herein is administered for prophylactic and/or therapeutic treatments. In therapeutic applications, the compositions are administered to a patient already suffering from a disease or condition, in an amount sufficient to cure or at least partially arrest at least one of the symptoms of the disease or condition. In certain embodiments, amounts effective for this use depend on the severity and course of the disease or condition, previous therapy, the patient's health status, weight, and response to the drugs, and/or the judgment of the treating physician.

In prophylactic applications, compositions containing Compound 1, or a pharmaceutically acceptable salt thereof (e.g. Compound 2), described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In certain embodiments, administration of the compound, compositions or therapies as described herein includes chronic administration. In certain embodiments, chronic administration includes administration for an extended period of time, including, e.g., throughout the duration of the patient's life in order to ameliorate or otherwise control or limit the symptoms of the patient's disease or condition. In some embodiments, chronic administration includes daily administration.

In some embodiments, administration of the compounds, compositions or therapies described herein is given continuously. In alternative embodiments, the dose of drug being administered is temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

In some embodiments, Compound 1, or a pharmaceutically acceptable salt thereof (e.g. Compound 2) has a long lasting effect in mammals (e.g., the off-rate of the compound from DP2 is slower than its on-rate). In some embodiments, the long lasting effect of Compound 1, or a pharmaceutically acceptable salt thereof (e.g. Compound 2) is a result of the effect of the compound on apoptosis of Th2 cells. In some embodiments, the long lasting effect of Compound 1, or a pharmaceutically acceptable salt thereof (e.g. Compound 2) is a result of the slow off-rate of the compound from the $DP_2$ receptor. In one embodiment, the off-rate of Compound 1 from the $DP_2$ receptor is slower than the off-rate observed for $PGD_2$ from the $DP_2$ receptor. In one embodiment, the off-rate of Compound 1 from the $DP_2$ receptor is at least twice or at least three times as long as the off-rate of $PGD_2$ from the $DP_2$ receptor.

In some embodiments, Compound 1, or a pharmaceutically acceptable salt thereof (e.g. Compound 2) is administered to a mammal in which the following treatment cycle is utilized: (a) a first period during which Compound 1, or a pharmaceutically acceptable salt thereof (e.g. Compound 2) is administered to the mammal; and (b) a second period of at least seven days during which the Compound 1, or a pharmaceutically acceptable salt thereof (e.g. Compound 2) is administered to the mammal in a reduced amount. In some embodiments, the mammal is experiencing at least one symptom of an allergic disease or condition. In further embodiments, the allergic disease or condition is induced by the presence of an allergen. In yet further embodiments, the allergen is presented or suspected to be present during the treatment period. In some embodiments, the first period includes 1 to 10 days. In some embodiments, the first period comprises daily administration of Compound 1, or a pharmaceutically acceptable salt thereof (e.g. Compound 2). In some embodiments, the first period comprises once a day administration Compound 1, or a pharmaceutically acceptable salt thereof (e.g. Compound 2). In some embodiments, the second period includes at least 2 days. In some embodiments, the second period includes at least 7 days, at least 14 days, at least 21 days or at least 28 days. In some embodiments, the daily amount of Compound 1, or a pharmaceutically acceptable salt thereof (e.g. Compound 2) that is administered in the second period is reduced by at least 50% as compared to the first period. In some embodiments, the administration of Compound 1, or a pharmaceutically acceptable salt thereof (e.g. Compound 2) is discontinued in the second period.

In some embodiments, the treatment cycle is used once. In other embodiments, the treatment cycle is repeated until treatment is no longer needed.

In some embodiments, the compounds, compositions or therapies described herein are administered in at least one priming dose, followed by at least one maintenance dose. In certain embodiments, a priming dose of the agent(s) is administered until the symptoms of the disorder, disease or condition treated have been reduced (e.g., to a satisfactory level). Upon reduction, a maintenance dose of the compounds, compositions or therapies described herein is administered if desired or if necessary. In some embodiments, the maintenance dose comprises administration of the agent(s) described herein in an amount sufficient to at least partially maintain the reduction achieved by administration of the priming dose. In various embodiments, the maintenance dose, compared to the priming dose, includes a decrease in dosage and/or frequency of administration of the agent or one or more of the agents administered in the method. In certain embodiments, however, intermittent treatment with increased frequency and/or dosage amounts may be necessary upon any recurrence of symptoms.

In certain embodiments, the amount of a given agent that corresponds to a priming or maintenance amount varies depending upon factors including, by way of non-limiting example, the specific agent(s) utilized, the disease condition and its severity, the identity (e.g., weight) of the subject or host in need of treatment, and/or the route of administration. In various embodiments, the desired dose is conveniently presented in a single dose or in divided doses administered simultaneously (or over a short period of time) or at appropriate intervals, for example as two, three, four or more sub-doses per day.

Pharmacokinetic and Pharmacodynamic Analysis

In one embodiment, any standard pharmacokinetic protocol is used to determine blood plasma concentration profile in humans following administration of a formulation described herein (that include Compound 1, or a pharmaceutically acceptable salt thereof (e.g. Compound 2)). For example, a randomized single-dose crossover study is performed using a group of healthy adult human subjects. The number of subjects is sufficient to provide adequate control of variation in a statistical analysis, and is typically about 10 or greater, although for certain purposes a smaller group suffices. Each subject receives administration at time zero a single dose of a formulation of Compound 1, or a pharmaceutically acceptable salt thereof (e.g. Compound 2) (e.g., a dose containing about 0.3 mg, about 3 mg, about 10 mg, about 30 mg, about 60 mg, about 100 mg, about 300 mg, or about 600 mg of Compound 1, or a pharmaceutically acceptable salt thereof (e.g. Compound 2)), normally at around 8 am following an overnight fast. The subjects continue to fast and remain in an upright position for about 2 hours after administration of the formulation. Blood samples are collected from each subject prior to administration (e.g., 15 minutes) and at several intervals after administration. In certain instances, several samples are taken within the first hour and taken less frequently thereafter. Illustratively, blood samples are collected at 0 (pre-dose), 0.25, 0.5, 1, 2, 3, 4, 6, 8, 12, and 16 hours after administration and, 24, 36, 48, 60 and 72 hours after administration. If the same subjects are to be used for study of a second test formulation, a period of at least 10 days should elapse before administration of the second formulation. Plasma is separated from the blood samples by centrifugation and the separated plasma is analyzed for Compound 1 by a validated high performance liquid chromatography/tandem weight spectrometry (LC/APCI-MS/MS) procedure such as, for example, Ramu et al., *Journal of Chromatography B*, 751 (2001) 49-59).

Any formulation giving the desired pharmacokinetic profile is suitable for administration according to the present methods.

Pharmacodynamic effects following administration of Compound 1, or a pharmaceutically acceptable salt thereof (e.g. Compound 2) can be assessed by a variety of methods. In some embodiments, the $PGD_2$-induced eosinophil shape change (ESC) in human whole blood is used as a pharmacodymanic marker. $DP_2$ is highly expressed on eosinophils, Th2 cells and basophils and has been shown to mediate a proinflammatory and chemotactic effect of $PGD_2$ on these cells. Compounds which antagonize the binding of $PGD_2$ are expected to inhibit the chemotactic and proinflammatory responses induced by $PGD_2$. Blood is collected from the subjects prior to dosing and at various time intervals after dosing. $PGD_2$ is added to the blood, and the blood sample is processed for evaluation of eosinophil shape change by measuring forward scatter using flow cytometry. The inhibition of eosinophil shape change relates to the blood concentration of Compound 1, providing a pharmacodynamic assessment for Compound 1, or a pharmaceutically acceptable salt thereof (e.g. Compound 2), following oral administration.

In some embodiments, pharmacodynamic effects are assessed by allergen skin prick tests. In some embodiments, assessment of pharmacodynamic effects is performed in a Vienna Challenge Chamber experiment in which patients carry out self-assessment and scoring of their symptoms on a scale of 0 to 3. Separate scores may be given for eye symptoms, nasal symptoms (including nasal obstruction, nasal itch, sneeze and rhinorrhea) and other symptoms. Although the symptom score for each patient is subjective, if a sufficient number of patients is used, the total scores are meaningful.

In some embodiments, asthma symptoms are quantified using measurements of lung function such as forced expiratory volume in one second (FEV1) or peak expiratory flow rate (PEF) or using the Juniper quality of life scale.

In some embodiments, the severity of atopic dermatitis symptoms are assessed using the scoring atopic dermatitis (SCORAD) or six area six sign atopic dermatitis (SASSAD) systems.

Combination Therapies

In certain instances, it is appropriate to administer Compound 1, or a pharmaceutically acceptable salt thereof (e.g. Compound 2) in combination with another therapeutic agent.

In one embodiment, the compositions and methods described herein are also used in conjunction with other therapeutic reagents that are selected for their particular usefulness against the condition that is being treated. In general, the compositions described herein and, in embodiments where combinational therapy is employed, other agents do not have to be administered in the same pharmaceutical composition, and are, because of different physical and chemical characteristics, administered by different routes. In one embodiment, the initial administration is made according to established protocols, and then, based upon the observed effects, the dosage, modes of administration and times of administration, further modified.

In various embodiments, the compounds are administered concurrently (e.g., simultaneously, essentially simultaneously or within the same treatment protocol) or sequentially, depending upon the nature of the disease, the condition of the patient, and the actual choice of compounds used. In certain embodiments, the determination of the order of administration, and the number of repetitions of administration of each therapeutic agent during a treatment protocol, is based upon evaluation of the disease being treated and the condition of the patient.

Contemplated pharmaceutical compositions provide a therapeutically effective amount of Compound 1, or a pharmaceutically acceptable salt thereof (e.g. Compound 2) enabling, for example, once-a-day, twice-a-day, three times a day, etc. administration. In one aspect, pharmaceutical compositions provide an effective amount of Compound 1, or a pharmaceutically acceptable salt thereof (e.g. Compound 2) enabling once-a-day dosing.

In specific embodiments, in a treatment for asthma involving administration of Compound 1, or a pharmaceutically acceptable salt thereof (e.g. Compound 2), increased therapeutic benefit results by also providing the patient with other therapeutic agents or therapies for asthma. In various embodiments, administration to an individual of Compound 1, or a pharmaceutically acceptable salt thereof (e.g. Compound 2) in combination with a second agent provides the individual with, e.g., an additive or synergistic benefit.

Therapeutically-effective dosages vary when the drugs are used in treatment combinations. Determination of therapeutically-effective dosages of drugs and other agents when used in combination treatment regimens is achieved in any manner. For example, the use of metronomic dosing, i.e., providing more frequent, lower doses in order to minimize toxic side effects can be utilized. In certain instances, the combination therapy allows for either or both of the Compound 1, or a pharmaceutically acceptable salt thereof (e.g. Compound 2) and the second agent to have a therapeutically effective amount that is lower than would be obtained when administering either agent alone.

A combination treatment regimen encompasses, by way of non-limiting example, treatment regimens in which administration of Compound 1, or a pharmaceutically acceptable salt thereof (e.g. Compound 2) is initiated prior to, during, or after treatment with a second agent, and continues until any time during treatment with the second agent or after termination of treatment with the second agent. It also includes treatments in which Compound 1, or a pharmaceutically acceptable salt thereof (e.g. Compound 2) and the second agent being used in combination are administered simultaneously or at different times and/or at decreasing or increasing intervals during the treatment period. Combination treatment further includes periodic treatments that start and stop at various times to assist with the clinical management of the patient.

In some embodiments, combination therapies described herein are used as part of a specific treatment regimen intended to provide a beneficial effect from the co-action of a DP2 antagonist, e.g Compound 1, or a pharmaceutically acceptable salt thereof (e.g. Compound 2), and a concurrent treatment. It is understood that in certain embodiments, the dosage regimen to treat, prevent, or ameliorate the condition(s) for which relief is sought, is modified, in one embodiment, in accordance with a variety of factors. These factors include, by way of non-limiting example, the type of disease or condition being from which the subject suffers, as well as the age, weight, sex, diet, and/or medical condition of the subject. Thus, in some embodiments, the dosage regimen employed, varies and/or deviates from the dosage regimens set forth herein.

In some embodiments, provided herein are compositions, and methods of administering compositions comprising Compound 1, or a pharmaceutically acceptable salt thereof (e.g. Compound 2) in combination with an therapeutic agent selected from: 5-lipoxygenase-activating protein inhibitors, 5-lipoxygenase inhibitors, CYSLTR1 antagonists, CYSLTR2 antagonists, BLT1 antagonists, BLT2 antagonists, thromboxane antagonists, DP1 receptor antagonists, DP1 receptor agonists, IP receptor agonists, anti-IgE, chemokine receptor antagonists, IL5 antibody, bronchodilators, theophylline, leukotriene receptor antagonists, leukotriene formation inhibitors, decongestants, antihistamines, mucolytics, corticosteroids, glucocorticoids, anticholinergics, antitussives, analgesics, expectorants, and β-2 agonists.

In some embodiments, provided herein are compositions, and methods of administering compositions comprising Compound 1, or a pharmaceutically acceptable salt thereof (e.g. Compound 2) in combination with a therapeutic agent useful for treating respiratory conditions. Therapeutic agents useful for treating respiratory conditions and disorders, include: glucocorticoids; leukotriene modifiers; mast cell stabilizers; antimuscarinics/anticholinergics; methylxanthines; antihistamines; omalizumab, olapatidine and azelastine; an IgE blocker; beta2-adrenergic receptor agonists, such as: short acting beta2-adrenergic receptor agonists, and long-acting beta2-adrenergic receptor agonists.

In some embodiments, Compound 1, or a pharmaceutically acceptable salt thereof (e.g. Compound 2) is used in combination with one or more other therapeutic agents selected from anti-inflammatory agents, anticholinergic agents (particularly an $M_1/M_2/M_3$ receptor antagonist), $β_2$-adrenoreceptor agonists, antiinfective agents, antihistamines, PDE-4 inhibitors, H1 antagonist, H3 antagonist (and/or inverse agonist), H1/H3 dual antagonist (and/or inverse agonist), PDE4 inhibitor, $β_2$-adrenoreceptor agonist, corticosteroid, non-steroidal GR agonist, anticholinergic, antihistamine, leukotriene receptor antagonists, a $CysLT_1$ receptor antagonist, dual $CysLT_1/CysLT_2$ receptor antagonist, NSAIDs and NO-donors or NSAIDs and proton-pump inhibitors, inhibitors of UDP-glucuronosyltransferase (UGT).

In some embodiments, the other therapeutic ingredient(s) are used in the form of salts (e.g. as alkali metal or amine salts or as acid addition salts), or prodrugs (including esters (e.g. alkyl esters)), or as solvates, (e.g. hydrates). In one aspect, if appropriate, the therapeutic ingredients will be used in optically pure form or in racemic form.

The individual compounds of such combinations are administered either sequentially or simultaneously in separate or combined pharmaceutical formulations.

In one aspect, Compound 1, or a pharmaceutically acceptable salt thereof (e.g. Compound 2) is combined with or administered in combination with: one or more agents used to treat used to treat asthma (including, but not limited to: combination Inhalers; inhaled Beta-2 agonists; inhaled corticosteroids; leukotriene modifiers; mast cell stabilizers; monoclonal antibodies; oral Beta-2 agonists; bronchodilator); one or more agents used to treat allergy (including, but not limited to: antihistamine and decongestant combinations; antihistamines; decongestants; leukotriene modifiers; nasal anticholinergics; nasal corticosteroids; nasal decongestants; nasal mast cell stabilizers); one or more agents used to treat chronic obstructive pulmonary disease (COPD) (including, but not limited to: anticholinergics; combination Inhalers; corticosteroids; inhaled Beta-2 Agonists; inhaled Corticosteroids; mukolytics; oral Beta-2 agonists; bronchodilator).

In any of the compositions, combinations, methods of treating or combination methods of treating described herein Compound 2 is used.

In any of the compositions, combinations, methods of treating or combination methods of treating described herein Compound 1 (free acid) is used.

In certain embodiments, co-administration of a UGT inhibitor allows for lower doses of Compound 1, or a pharmaceutically acceptable salt thereof (e.g. Compound 2) to be administered.

Therapeutic agents useful for treating respiratory conditions and disorders, include, by way of non-limiting example: glucocorticoids, such as, ciclesonide, beclomethasone dipropionate, budesonide, flunisolide, fluticasone propionate, fluticasone furoate, mometasone furoate, and triamcinolone; leukotriene modifiers, such as, montelukast, zafirlukast, pranlukast, and zileuton; mast cell stabilizers, such as, cromoglicate (cromolyn), and nedocromil; antimuscarinics/anticholinergics, such as, ipratropium, oxitropium, and tiotropium; methylxanthines, such as, theophylline and aminophylline; antihistamines, such as, mepyramine (pyrilamine), antazoline, diphenhydramine, carbinoxamine, doxylamine, clemastine, dimenhydrinate, pheniramine, chlorphenamine (chlorpheniramine), dexchlorphenamine, brompheniramine, triprolidine, cyclizine, chlorcyclizine, hydroxyzine, meclizine, promethazine, alimemazine (trimeprazine), cyproheptadine, azatadine, ketotifen, acrivastine, astemizole, cetirizine, loratadine, mizolastine, terfenadine, fexofenadine, levocetirizine, desloratadine, fexofenadine; omalizumab, olapatidine and azelastine; an IgE blocker; beta2-adrenergic receptor agonists, such as: short acting beta2-adrenergic receptor agonists, such as, salbutamol (albuterol), levalbuterol, terbutaline, pirbuterol, procaterol, metaproterenol, fenoterol, bitolterol mesylate; and long-acting beta2-adrenergic receptor agonists, such as, salmeterol, formoterol, indacaterol and bambuterol.

In some embodiments, provided herein are combinations therapies that combine treatment with Compound 1, or a pharmaceutically acceptable salt thereof (e.g. Compound 2), with treatment with an inhibitor of leukotriene synthesis or with a leukotriene receptor antagonist.

In some embodiments, the second therapeutic agent is a FLAP inhibitor compound. In some embodiments, the FLAP inhibitor is selected from compounds described in U.S. patent application Ser. No. 11/538,762 (issued as U.S. Pat. No. 7,405,302); U.S. patent application Ser. No. 12/131,828; U.S. patent application Ser. No. 11/553,946 (published as 2007/0105866); U.S. patent application Ser. No. 11/925,841; U.S. patent application Ser. No. 12/089,706; U.S. patent application Ser. No. 12/089,707; U.S. patent application Ser. No. 12/092,570; U.S. patent application Ser. No. 11/744,555 (published as 2007/0219206); U.S. patent application Ser. No. 11/746,010 (published as 2007/0225285); U.S. patent application Ser. No. 11/745,387 (published as 2007/0244128); U.S. patent application Ser. No. 12/257,876; U.S. patent application No. 61/055,887; U.S. patent application No. 61/055,899; International Patent Application no. PCT/US07/86188; WO 07/047207; WO07/056021; WO07/056220; WO07/056228; International Patent Application no. PCT/US08/62310; International Patent Application no. PCT/US08/062793; International Patent Application no. PCT/US08/62580; International Patent Application no. PCT/US2008/052960; International Patent Application no. PCT/US08/81190; International Patent Application no. PCT/US08/76225; each of which is herein incorporated by reference in its entirety.

In some embodiments, the second therapeutic agent is a FLAP inhibitor that is selected from: MK886 (also known as 3-[3-tert-butylsulfanyl-1-(4-chloro-benzyl)-5-isopropyl-1H-indol-2-yl]-2,2-dimethyl-propionic acid); MK591 (also known as 3-[3-tert-butylsulfanyl-1-(4-chloro-benzyl)-5-(quinolin-2-ylmethoxy)-1H-indol-2-yl]-2,2-dimethyl-propionic acid); and DG031 (also known as BAY X1005; cyclopentyl[4-(quinolin-2-ylmethoxy)-phenyl]-acetic acid), (3-[3-tert-Butylsulfanyl-1-[4-(5-methoxy-pyrimidin-2-yl)-benzyl]-5-(5-methyl-pyridin-2-ylmethoxy)-1H-indol-2-yl]-2,2-dimethyl-propionic acid); (3-[3-tert-Butylsulfanyl-1-[4-(5-methoxy-pyrimidin-2-yl)-benzyl]-5-(5-methyl-pyrazin-2-ylmethoxy)-1H-indol-2-yl]-2,2-dimethyl-propionic acid); (3-[5-((S)-1-Acetyl-2,3-dihydro-1H-indol-2-ylmethoxy)-3-tert-butylsulfanyl-1-[4-(5-methoxy-pyrimidin-2-yl)-benzyl]-1H-indol-2-yl}-2,2-dimethyl-propionic acid); (3-[3-tert-Butylsulfanyl-1-[4-(6-methoxy-pyridin-3-yl)-benzyl]-5-(pyridin-2-ylmethoxy)-1H-indol-2-yl]-2,2-dimethyl-propionic acid); (3-[3-tert-Butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid); (3-[3-tert-Butylsulfanyl-1-[4-(5-fluoro-pyridin-2-yl)-benzyl]-5-(quinolin-2-ylmethoxy)-1H-indol-2-yl]-2,2-dimethyl-propionic acid); (2-[3-tert-Butylsulfanyl-1-[4-(5-methoxy-pyrimidin-2-yl)-benzyl]-5-(5-methyl-pyridin-2-ylmethoxy)-1H-indol-2-ylmethyl]-2-ethyl-butyric acid); (3-[3-tert-Butylsulfanyl-1-[4-(6-methoxy-pyridin-3-yl)-benzyl]-5-(5-methyl-pyridin-2-ylmethoxy)-1H-indol-2-yl]-2,2-dimethyl-propionic acid); (3-[5-((S)-1-Acetyl-pyrrolidin-2-ylmethoxy)-3-tert-butylsulfanyl-1-(4-chloro-benzyl)-1H-indol-2-yl]-2,2-dimethyl-propionic acid); (3-[3-tert-butylsulfanyl-1-[4-(5-fluoro-pyridin-2-yl)-benzyl]-5-(pyridin-2-ylmethoxy)-1H-indol-2-yl]-2,2-dimethyl-propionic acid), (3-[5-((S)-1-Acetyl-2,3-dihydro-1H-indol-2-ylmethoxy)-3-tert-butylsulfanyl-1-[4-(5-ethoxy-pyrimidin-2-yl)-benzyl]-1H-indol-2-yl}-2,2-dimethyl-propionic acid), or pharmaceutically acceptable salt or N-oxide thereof.

In some embodiments, the FLAP inhibitor is selected from compounds described in U.S. Pat. Nos. 4,929,626; 4,970,215; 5,081,138; 5,095,031; 5,204,344; 5,126,354; 5,221,678; 5,229,516; 5,272,145; 5,283,252; 5,288,743;

5,292,769; 5,304,563; 5,399,699; 5,459,150; 5,512,581; 5,597,833; 5,668,146; 5,668,150; 5,691,351; 5,714,488; 5,783,586; 5,795,900; and 5,843,968, each of which is herein incorporated by reference for the disclosure of such FLAP inhibitors).

In some embodiments described herein, Compound 1, or a pharmaceutically acceptable salt thereof (e.g. Compound 2) is used in combination with leukotriene receptor antagonists including, but are not limited to, $CysLT_1/CysLT_2$ dual receptor antagonists, and $CysLT_1$ receptor anatagonists. $CysLT_1$ receptor antagonists include, but are not limited to, zafirlukast, montelukast, prankulast, and derivatives or analogs thereof. In one embodiment, such combinations are used to treat respiratory disorders.

In additional embodiments, provided herein are therapies which combine administration of Compound 1, or a pharmaceutically acceptable salt thereof (e.g. Compound 2) with the administration of an anti-inflammatory agent. In specific embodiments, such therapies are used in the treatment of prostaglandin $D_2$-dependent or prostaglandin $D_2$-mediated diseases or conditions.

In certain aspects, Compound 1, or a pharmaceutically acceptable salt thereof (e.g. Compound 2) is combined with or administered in combination with one or more agents used to treat used to treat asthma, including, but not limited to: combination Inhalers (fluticasone propionate and salmeterol xinafoate, budesonide and formoterol fumarate and indacaterol and mometasone furoate); inhaled Beta-2 agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled corticosteroids (beclomethasone oral inhalation; budesonide inhalation solution; budesonide inhaler; flunisolide oral inhalation; fluticasone inhalation aerosol; fluticasone powder for oral inhalation; mometasone inhalation powder; triamcinolone oral inhalation); leukotriene modifiers (montelukast; zafirlukast; zileuton); mast cell stabilizers (cromolyn inhaler; nedocromil oral inhalation); monoclonal antibodies (omalizumab); oral Beta-2 agonists (albuterol oral syrup; albuterol oral tablets; metaproterenol; terbutaline); bronchodilator (aminophylline; oxtriphylline; theophylline).

In one aspect, Compound 1, or a pharmaceutically acceptable salt thereof (e.g. Compound 2) is combined with or administered in combination with one or more agents used to treat allergy, including, but not limited to: antihistamine and decongestant combinations (cetirizine and pseudoephedrine; desloratadine and pseudoephedrine ER; fexofenadine and pseudoephedrine; loratadine and pseudoephedrine); antihistamines (azelastine nasal spray; brompheniramine; brompheniramine oral suspension; carbinoxamine; cetirizine; chlorpheniramine; clemastine; desloratadine; dexchlorpheniramine ER; dexchlorpheniramine oral syrup; diphenhydramine oral; fexofenadine; loratadine; promethazine); decongestants (pseudoephedrine); leukotriene modifiers (montelukast; montelukast granules); nasal anticholinergics (ipratropium); nasal corticosteroids (beclomethasone nasal inhalation; budesonide nasal inhaler; flunisolide nasal inhalation; fluticasone nasal inhalation; mometasone nasal spray; triamcinolone nasal inhalation; triamcinolone nasal spray); nasal decongestants (phenylephrine); nasal mast cell stabilizers (cromolyn nasal spray).

In one aspect, Compound 1 or a pharmaceutically acceptable salt thereof (e.g. Compound 2) is combined with or administered in combination with one or more agents used to treat chronic obstructive pulmonary disease (COPD), including, but not limited to: anticholinergics—ipratropium bromide oral inhalation); combination Inhalers (albuterol and ipratropium (e.g. Combivent, DuoNeb); fluticasone and salmeterol oral inhalation (e.g. Advair)); corticosteroids (dexamethasone tablets; fludrocortisone acetate; hydrocortisone tablets; methylprednisolone; prednisolone liquid; prednisone oral; triamcinolone oral); inhaled Beta-2 Agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled Corticosteroids (beclomethasone oral inhalation; budesonide inhalation solution; budesonide inhaler; flunisolide oral inhalation; fluticasone inhalation aerosol; fluticasone powder for oral inhalation; triamcinolone oral inhalation); mukolytics (guaifenesin); oral Beta-2 agonists (albuterol oral syrup; albuterol oral tablets; metaproterenol; terbutaline); bronchodilator (aminophylline; oxtriphylline; theophylline).

In one aspect, Compound 1, or a pharmaceutically acceptable salt thereof (e.g. Compound 2) is used in combination with one or more other therapeutic agents or the pharmaceutical compositions of Compound 1, or a pharmaceutically acceptable salt thereof (e.g. Compound 2) include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents, or antihistamines. In one case, antiinfective agents include antibiotics and/or antivirals. In a further aspect, a combination comprising Compound 1, or a pharmaceutically acceptable salt thereof (e.g. Compound 2) includes one or more other therapeutically active agent, where the one or more other therapeutically active agents are selected from an anti-inflammatory agent such as a corticosteroid or an NSAID, an anticholinergic agent, a $\beta_2$-adrenoreceptor agonist, an antiinfective agent such as an antibiotic or an antiviral, or an antihistamine. One embodiment encompasses combinations comprising Compound 1, or a pharmaceutically acceptable salt thereof (e.g. Compound 2) together with a $\beta_2$-adrenoreceptor agonist, and/or an anticholinergic, and/or a PDE-4 inhibitor, and/or an antihistamine. Another embodiment encompasses combinations comprising Compound 1, or a pharmaceutically acceptable salt thereof (e.g. Compound 2) together with a corticosteroid or NSAID.

In some embodiments, the other therapeutic ingredient(s) will be used in the form of salts (e.g. as alkali metal or amine salts or as acid addition salts), or prodrugs (such as esters (e.g. alkyl esters)), or as solvates (e.g. hydrates). In one aspect, if appropriate, the therapeutic ingredients will be used in optically pure form. In another aspect, if appropriate, the therapeutic ingredients will be used in racemic form.

Examples of $\beta_2$-adrenoreceptor agonists include salmeterol (as a racemate or a single enantiomer such as the R-enantiomer), salbutamol (as a racemate or a single enantiomer such as the R-enantiomer), formoterol (as a racemate or a single diastereomer such as the R,R-diastereomer), salmefamol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment the $\beta_2$-adrenoreceptor agonists are long-acting β$_2$-adrenoreceptor agonists, for example, compounds which provide effective bronchodilation for about 12 hours or longer.

In one embodiment, Compound 1, or a pharmaceutically acceptable salt thereof (e.g. Compound 2) is combined with or administered in combination with a phosphodiesterase 4 (PDE4) inhibitor, especially in the case of a formulation adapted for inhalation. The PDE4-specific inhibitor useful in this aspect is any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Examples of anticholinergic agents are those compounds that act as antagonists at the muscarinic receptors, in particular those compounds which are antagonists of the M$_1$ or M$_3$ receptors, dual antagonists of the M$_1$/M$_3$ or M$_2$/M$_3$, receptors or pan-antagonists of the M$_1$/M$_2$/M$_3$ receptors. Exemplary compounds for administration via inhalation include ipratropium (for example, as the bromide), oxitropium (for example, as the bromide) and tiotropium (for example, as the bromide). Also of interest are revatropate (for example, as the hydrobromide) and LAS-34273 which is disclosed in WO01/04118. Exemplary compounds for oral administration include pirenzepine, darifenacin (hydrobromide), oxybutynin, terodiline, tolterodine, tolterodine tartrate, otilonium (for example, as the bromide), trospium chloride, solifenacin, and solifenacin succinate.

In one embodiment, Compound 1, or a pharmaceutically acceptable salt thereof (e.g. Compound 2) is combined with or administered in combination with an H1 antagonist. Examples of H1 antagonists include, but are not limited to, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly azelastine, cetirizine, levocetirizine, efletirizine and fexofenadine.

In another embodiment, Compound 1, or a pharmaceutically acceptable salt thereof (e.g. Compound 2) is combined with or administered in combination with an H3 antagonist (and/or inverse agonist).

In another embodiment, Compound 1, or a pharmaceutically acceptable salt thereof (e.g. Compound 2) is combined with or administered in combination with an H1/H3 dual antagonist (and/or inverse agonist).

In another aspect, Compound 1, or a pharmaceutically acceptable salt thereof (e.g. Compound 2) is combined with or administered in combination with a PDE4 inhibitor.

In another aspect, Compound 1, or a pharmaceutically acceptable salt thereof (e.g. Compound 2) is combined with or administered in combination with a β$_2$-adrenoreceptor agonist.

In another aspect, Compound 1, or a pharmaceutically acceptable salt thereof (e.g. Compound 2) is combined with or administered in combination with a corticosteroid.

In another aspect, Compound 1, or a pharmaceutically acceptable salt thereof (e.g. Compound 2) is combined with or administered in combination with a non-steroidal GR agonist.

In another aspect, Compound 1, or a pharmaceutically acceptable salt thereof (e.g. Compound 2) is combined with or administered in combination with an anticholinergic.

In another aspect, Compound 1, or a pharmaceutically acceptable salt thereof (e.g. Compound 2) is combined with or administered in combination with an antihistamine.

In another aspect, Compound 1, or a pharmaceutically acceptable salt thereof (e.g. Compound 2) is combined with or administered in combination with a PDE4 inhibitor and a β$_2$-adrenoreceptor agonist.

In another aspect, Compound 1, or a pharmaceutically acceptable salt thereof (e.g. Compound 2) is combined with or administered in combination with an anticholinergic and a PDE-4 inhibitor.

In one embodiment, Compound 1, or a pharmaceutically acceptable salt thereof (e.g. Compound 2) is combined with or administered to a patient in combination with inhaled corticosteroids.

In one embodiment, Compound 1, or a pharmaceutically acceptable salt thereof (e.g. Compound 2) is combined with or administered to a patient in combination with beta2-adrenergic receptor agonists. In one embodiment, Compound 1, or a pharmaceutically acceptable salt thereof (e.g. Compound 2) is combined with or administered to a patient in combination with short acting beta2-adrenergic receptor agonists. In one embodiment, Compound 1, or a pharmaceutically acceptable salt thereof (e.g. Compound 2) is combined with or administered to a patient in combination with long-acting beta2-adrenergic receptor agonists.

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

Corticosteroids, include, but are not limited to: betamethasone (Celestone), prednisone Deltasone), alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In one embodiment, Compound 1, or a pharmaceutically acceptable salt thereof (e.g. Compound 2) is combined with or administered in combination with one or more agents that are inhibitors of UDP-glucuronosyltransferase (UGT). UGT inhibitors include those described in U.S. 2003/0215462; U.S. 2004/0014648. In some embodiments, co-administration of a UGT inhibitor allows for lower doses of Compound 1, or a pharmaceutically acceptable salt thereof (e.g. Compound 2) to be administered.

The individual compounds of such combinations are administered either sequentially or simultaneously in separate or combined pharmaceutical formulations. In one embodiment, the individual compounds will be administered simultaneously in a combined pharmaceutical formulation. Appropriate doses of known therapeutic agents will be appreciated by those skilled in the art.

The combinations referred to herein are conveniently presented for use in the form of a pharmaceutical compositions together with a pharmaceutically acceptable diluent(s) or carrier(s).

Kits/Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, bags, containers, bottles, and any packaging material suitable for a selected formulation and intended mode of administration and treatment. A wide array of formulations of the compounds and compositions provided herein are contemplated as are a variety of treatments for any disease, disorder, or condition that would benefit by antagonism of DP2 receptors.

For example, the container(s) include Compound 1, or a pharmaceutically acceptable salt thereof (e.g. Compound 2), optionally in a composition or in combination with another agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

It is to be understood that as used herein, pharmaceutical compositions described as comprising a pharmaceutically acceptable salt described herein, e.g., liquid solutions, encompass pharmaceutical compositions comprising the associated and/or disassociated forms of the salt. Thus, for example, a pharmaceutical composition described herein comprising an aqueous solution of Compound 2 encompasses a composition comprising a population of sodium cations and a population of [2'-(3-benzyl-1-ethyl-ureidomethyl)-6-methoxy-4'-trifluoromethyl-biphenyl-3-yl]-acetate anions.

EXAMPLES

The following ingredients, formulations, processes and procedures for practicing the methods disclosed herein correspond to that described above. The procedures below describe with particularity illustrative, non-limiting embodiment of formulations that include a Compound 1, or a pharmaceutically acceptable salt and/or solvate thereof, and pharmacokinetic profiles and pharmacodynamic effects thereof. By way of example only, Compound 1 is optionally prepared as outlined in U.S. patent application Ser. No. 12/362,439, or as outlined herein.

Example 1

Preparation of Compound 1

In one embodiment, [2'-(3-benzyl-1-ethyl-ureidomethyl)-6-methoxy-4'-trifluoromethyl-biphenyl-3-yl]-acetic acid ethyl ester (prepared as described in U.S. patent application Ser. No. 12/362,439) was dissolved in tetrahydrofuran, ethanol and 50% NaOH aqueous solution was added, and the mixture was stirred at room temperature for 1 hour. Water and methyl tert-butyl ether are added and stirred for an additional 10 minutes. The layers are separated and collected independently. Concentrated HCl is added to the aqueous layer. Methyl tert-butyl ether is added to extract Compound 1 from the aqueous layer. The methyl tert-butyl ether layer is then dried with sodium sulfate, filtered, and concentrated to provide Compound 1.

Example 1a

Synthesis of Compound 1

Step 1:
To (3-bromo-4-methoxy-phenyl)-acetic acid (5.226 g, 21.32 mmol) in MeOH (52 mL) was added thionyl chloride (3.1 mL, 42.65 mmol), and the reaction was stirred at room temperature for 2 hours. Once no starting material was seen by analytical LCMS, the mixture was concentrated and then diluted with $CH_2Cl_2$ and aqueous 1N NaOH. The aqueous layer was separated and extracted with $CH_2Cl_2$, and the combined organic layers were washed with $H_2O$, dried over $MgSO_4$, filtered, and concentrated to give (3-bromo-4-methoxy-phenyl)-acetic acid methyl ester.

Step 2:
(3-Bromo-4-methoxy-phenyl)-acetic acid methyl ester (5.1 g, 19.68 mmol), bis(pinacolato)diboron (6.54 g, 25.59 mmol), and potassium acetate (5.80 g, 59.05 mmol) were combined in DMF (100 mL) under $N_2$. The solution was purged with $N_2$, and then (1,1'-bis(diphenylphosphino)ferrocene)-dichloropalladium(II) (0.805 g, 0.98 mmol) was added and the reaction was heated to 85° C. overnight. Starting material was still observed after 16 hours, so additional (1,1'-bis(diphenylphosphino)ferrocene)-dichloropalladium(II) (0.808 g, 0.98 mmol) was added, and the reaction was stirred at 85° C. overnight. Once no starting material was seen by analytical LCMS, the mixture was cooled to room temperature and concentrated. The residue was partitioned between EtOAc and $H_2O$ and filtered through Celite. The aqueous layer was separated and extracted with EtOAc, and the combined organic layers were washed with brine, dried over $MgSO_4$, filtered, and concentrated. The residue was purified by silica gel chromatography (0-100% EtOAc in hexanes) to give [4-methoxy-3-(4,4,5,5-tetramethyl-[1,3,2]dioxaborolan-2-yl)-phenyl]-acetic acid methyl ester.

Step 3:

To (2-bromo-5-trifluoromethyl-phenyl)-methanol (2.216 g, 8.69 mmol) and N-methylmorpholine N-oxide (2.051 g, 17.38 mmol) in $CH_2Cl_2$ (44 mL) and MeCN (2.2 mL) was added tetrapropylammonium perruthenate (0.311 g, 0.87 mmol), and the reaction was stirred at room temperature for 20 minutes. Once no starting material was seen by analytical tlc, the mixture was concentrated and purified by silica gel chromatography to give 2-bromo-5-trifluoromethyl-benzaldehyde.

Step 4: 2-Bromo-5-trifluoromethyl-benzaldehyde (4.152 g, 16.41 mmol), [4-methoxy-3-(4,4,5,5-tetramethyl-[1,3,2]dioxaborolan-2-yl)-phenyl]-acetic acid methyl ester (4.988 g, 16.41 mmol), and potassium carbonate (5.67 g, 41.03 mmol) were combined in DME (40 mL) and $H_2O$ (20 mL) under $N_2$. The mixture was purged with $N_2$, and then tetrakis(triphenylphosphine)palladium(0) (1.9 g, 1.64 mmol) was added, and the reaction was heated to 90° C. for 10 hours. Once no starting material was seen by analytical LCMS, the mixture was cooled to room temperature and diluted with $CH_2Cl_2$ and $H_2O$. The aqueous layer was separated and extracted with $CH_2Cl_2$, and the combined organic layers were dried over $MgSO_4$, filtered, and concentrated. The residue was purified by silica gel chromatography (0-100% EtOAc in hexanes) to give (2'-formyl-6-methoxy-4'-trifluoromethyl-biphenyl-3-yl)-acetic acid methyl ester.

Step 5:

To (2'-formyl-6-methoxy-4'-trifluoromethyl-biphenyl-3-yl)-acetic acid methyl ester (1.0 g, 2.89 mmol) and ethylamine (2M in THF; 3.6 mL, 7.23 mmol) in $CH_2Cl_2$ (10 mL) was added sodium cyanoborohydride (0.587 g, 8.6 mmol), followed by acetic acid (0.1 mL). The reaction was stirred at room temperature until deemed to be complete by analytical HPLC. The solution was neutralized with saturated aqueous $NaHCO_3$ and extracted with $CH_2Cl_2$, and the combined organic layers were dried over $MgSO_4$, filtered, and concentrated to give (6-methoxy-2'-ethylaminomethyl-4'-trifluoromethyl-biphenyl-3-yl)-acetic acid methyl ester.

Step 6:

To (2'-ethylaminomethyl-6-methoxy-4'-trifluoromethyl-biphenyl-3-yl)-acetic acid methyl ester (0.207 g, 0.54 mmol) in $CH_2Cl_2$ (2 mL) at 0° C. was added diisopropylethylamine (0.21 mL, 1.19 mmol), followed by phosgene (20% in toluene; 0.34 mL, 0.65 mmol), and the reaction was stirred for 2 hours at 0° C. Benzylamine (0.09 mL, 0.81 mmol) was then added, and the reaction was stirred for 15 minutes. Triethylamine (0.1 mL, 0.72 mmol) was added, and the reaction was stirred for 1 hour. Additional benzylamine (0.09 mL, 0.81 mmol) and diisopropylethylamine (0.21 mL, 1.19 mmol) were added, and the reaction was stirred for 3 hours, until no starting material was seen by analytical LCMS. The mixture was partitioned between $H_2O$ and $CH_2Cl_2$, and the aqueous layer was separated and extracted twice with $CH_2Cl_2$. The combined organic layers were dried and concentrated, and the residue was purified by silica gel chromatography (20-40% EtOAc in hexanes) to give [2'-(3-benzyl-1-ethyl-ureidomethyl)-6-methoxy-4'-trifluoromethyl-biphenyl-3-yl]-acetic acid methyl ester.

Step 7:

[2'-(3-benzyl-1-ethyl-ureidomethyl)-6-methoxy-4'-trifluoromethyl-biphenyl-3-yl]-acetic acid methyl ester (0.1 g) in THF (2 mL) was treated with 1N aqueous LiOH (2 mL) for 2 hours at room temperature. The mixture was acidified with 1N aqueous HCl and extracted three times with EtOAc. The combined organic layers were dried and concentrated, and the residue was purified by preparative HPLC to give [2'-(3-benzyl-1-ethyl-ureidomethyl)-6-methoxy-4'-trifluoromethyl-biphenyl-3-yl]-acetic acid. M+H is 501.

Example 1b

Alternative Synthesis of Compound 1

Step 1:

(3-Bromo-4-methoxy-phenyl)-acetic acid ethyl ester was prepared according to the procedure described in Example 1a, Step 1, using 3-bromo-4-methoxyphenylacetic acid and ethanol.

Step 2:

(3-Bromo-4-methoxy-phenyl)-acetic acid ethyl ester (27.4 g, 100.3 mmol), bis(pinacolato)diboron (25.47 g, 100.3 mmol), and potassium acetate (24.6 g, 250.8 mmol) were combined in 1,4-dioxane (250 mL) under $N_2$. The solution was purged with $N_2$, and then (1,1'-bis(diphenylphosphino)ferrocene)-dichloropalladium(II) (4.10 g, 5.02 mmol) was added and the reaction was heated to 110° C. overnight. The mixture was filtered through Celite and partitioned between EtOAc and brine. The aqueous layer was separated and extracted twice with EtOAc, and the combined organic layers were dried and concentrated. The residue was purified by silica gel chromatography (20-60% EtOAc in hexanes) to give [4-methoxy-3-(4,4,5,5-tetramethyl-[1,3,2]dioxaborolan-2-yl)-phenyl]-acetic acid ethyl ester.

Step 3: 2-Bromo-5-(trifluoromethyl)benzaldehyde and [4-methoxy-3-(4,4,5,5-tetramethyl-[1,3,2]dioxaborolan-2-yl)-phenyl]-acetic acid ethyl ester were used to prepare (2'-Formyl-6-methoxy-4'-trifluoromethyl-biphenyl-3-yl)-acetic acid ethyl ester as described in Example 1a, Step 4.

Step 4:

To (2'-formyl-6-methoxy-4'-trifluoromethyl-biphenyl-3-yl)-acetic acid ethyl ester (1.0 g, 2.73 mmol) in MeOH (8 mL) was added ethylamine (2M in THF; 5 mL, 10 mmol), followed by acetic acid (0.23 mL, 4.09 mmol). Sodium cyanoborohydride (0.260 g, 4.14 mmol) was then added, and the reaction was stirred at room temperature and monitored by analytical LCMS. The reaction never reached completion, so the mixture was concentrated and partitioned between EtOAc and saturated aqueous $NaHCO_3$. The aqueous layer was extracted with EtOAc, and the combined organic layers were dried over $MgSO_4$, filtered, and concentrated. The residue was purified by silica gel chromatography (0-6% MeOH in CH$_2$Cl$_2$) to give (2'-ethylaminomethyl-6-methoxy-4'-trifluoromethyl-biphenyl-3-yl)-acetic acid ethyl ester.

Step 5:

To (2'-ethylaminomethyl-6-methoxy-4'-trifluoromethyl-biphenyl-3-yl)-acetic acid ethyl ester (44.9 g, 0.114 mol) in CH$_2$Cl$_2$ (450 mL) at room temperature was added triethylamine (24 mL, 0.17 mol), followed by benzylisocyanate (16.7 mL, 0.136 mol), and the reaction was stirred for 2 hours until no starting material was seen by analytical LCMS. The mixture was partitioned between H$_2$O and CH$_2$Cl$_2$, and the aqueous layer was separated and extracted with CH$_2$Cl$_2$. The combined organic layers were dried (MgSO$_4$) and concentrated, and the residue was purified by silica gel chromatography (0-60% EtOAc in hexanes) to give [2'-(3-benzyl-1-ethyl-ureidomethyl)-6-methoxy-4'-trifluoromethyl-biphenyl-3-yl]-acetic acid ethyl ester.

Step 6:

[2'-(3-Benzyl-1-ethyl-ureidomethyl)-6-methoxy-4'-trifluoromethyl-biphenyl-3-yl]-acetic acid ethyl ester (46.57 g) in THF (470 mL) and ethanol (370 mL) was treated with 1N aqueous NaOH (2 mL) for 45 minutes at room temperature. The mixture was acidified with 1N aqueous HCl (270 mL) and extracted three times with dichloromethane, the organics were dried with magnesium sulfate, filtered and concentrated, and the residue was purified by preparative HPLC to give [2'-(3-benzyl-1-ethyl-ureidomethyl)-6-methoxy-4'-trifluoromethyl-biphenyl-3-yl]-acetic acid.

Example 1c

Kilogram-Scale Synthesis of Compound 1

Step 1:

To a 400 L glass-lined reactor was charged 3-bromo-4-methoxyphenylacetic acid (15.0 kg) and ethanol (35.0 kg). To the reactor was charged concentrated sulfuric acid (0.42 kg; slowly using a diaphragm pump). Rinsed charging line with ethanol (2.0 kg). Heated reactor contents to reflux at ~79° C. Agitated at reflux for 4 hours. Cooled to 20° C. and then vacuum-distilled reactor contents until 31.2 kg of ethanol were removed, maintaining an internal temperature of ≤40° C. during distillation. Methyl t-butyl ether (MTBE; 56.0 kg) was added followed by 75.0 kg of 9% sodium bicarbonate solution and agitated the reactor contents for 10 minutes. Separated the layers and washed the MTBE layer one time with 75.0 kg of 9% sodium bicarbonate solution. The MTBE layer containing (3-bromo-4-methoxy-phenyl)-acetic acid ethyl ester was dried over 5.0 kg of anhydrous sodium sulfate and concentrated to dryness in a rotovap under vacuum at 45° C. bath temperature. Yield is 16.7 kg.

Step 2:

16.8 kg of bis(pinacolato)diboron and 14.7 kg of potassium acetate and a solution of 16.7 kg of (3-bromo-4-methoxy-phenyl)-acetic acid ethyl ester in 38.8 kg of N-methyl pyrrolidinone was charged to a 400 L glass-lined reactor. Also charged 36.2 kg of N-methyl pyrrolidinone. Started the agitator and bubbled nitrogen through the reaction mixture for 1 hour. Charged 1.0 kg of [1,1'-bis(diphenylphosphino)ferrocene]dichloropalladium(II)-DCM. Bubbled nitrogen gas through the reaction mixture for 10 minutes. Heated the reactor contents to 98.4° C. and agitated at the temperature for 17 hours. Reaction mixture was cooled to 20° C., drained and worked up in two portions, each weighing 62.0 kg. Charged to the reactor, 62.0 kg of reaction mixture. Charging line was rinsed with 5.0 kg of ethyl acetate. Charged 170.0 kg of ethyl acetate to reactor, followed by 129.0 kg of 12% sodium chloride solution. After agitating the reactor contents for 20 minutes the layers were separated. Washed the organic layer with 129.0 kg of 12% sodium chloride solution. The organic layer containing [4-methoxy-3-(4,4,5,5-tetramethyl-[1,3,2]dioxaborolan-2-yl)-phenyl]-acetic acid ethyl ester in ethyl acetate was dried over 5.0 kg of sodium sulfate, anhydrous. The second portion of reaction mixture was worked up in a similar way, except that 10.0 kg of sodium sulfate, anhydrous were used to dry the organic layer. The solution of [4-methoxy-3-(4,4,5,5-tetramethyl-[1,3,2]dioxaborolan-2-yl)-phenyl]-acetic acid ethyl ester in ethyl acetate was concentrated to dryness on rotovaps under vacuum at temperature of 45° C. (bath temperature). Yield is 30.3 kg.

Step 3:

Dissolved in round-bottom flasks 21.1 kg of crude [4-methoxy-3-(4,4,5,5-tetramethyl-[1,3,2]dioxaborolan-2-yl)-phenyl]-acetic acid ethyl ester in 73.0 kg of 1,4-dioxane. Charged the [4-methoxy-3-(4,4,5,5-tetramethyl-[1,3,2]dioxaborolan-2-yl)-phenyl]-acetic acid ethyl ester solution to a 400 L GL reactor. Rinsed the flasks with 15.0 kg of 1,4-dioxane and charged rinse to the reactor. Also charged 10.4 kg of 2-bromo-5-(trifluoromethyl)benzaldehyde, 58.0 kg of 25% potassium bicarbonate aqueous solution and 24.3 kg of 1,4-dioxane. Bubbled nitrogen gas through the reaction mixture for 1 hour. Slowly charged 0.9 kg of [1,1'-bis(diphenylphosphino)ferrocene]dichloropalladium(II)-DCM. Bubbled nitrogen gas through the reaction mixture for 10 minutes. Agitated the reaction mixture at 60±5° C. for a period of 1 hour. Cooled the reactor contents to 25° C. and drained the reactor contents into a drum. For the work up the reaction mixture was split into two equal portions of 97.8 kg each. To the reactor charged 97.8 kg of reaction mixture, 54.8 kg of ethyl acetate and 74.3 kg of 12% sodium chloride aqueous solution. Agitated for 20 minutes. Separated the layers and washed the organic layer with 74.3 kg of 12% sodium chloride aqueous solution. Agitated for 20 minutes. Separated the layers and dried the organic layer over 5.0 kg of sodium sulfate, anhydrous. The same work up was repeated for the second portion. The organic layers were concentrated to dryness on rotovap at 45° C. (bath temperature), and empty drums were rinsed with 10.0 kg of ethyl acetate each. Yield of (2'-formyl-6-methoxy-4'-trifluoromethyl-biphenyl-3-yl)-acetic acid ethyl ester is 19.9 kg (83.5% pure by liquid chromatography).

Loading of crude (2'-formyl-6-methoxy-4'-trifluoromethyl-biphenyl-3-yl)-acetic acid ethyl ester on silica gel plug, isolation and crystallization is outlined in Steps 3A-3D.

Step 3A:

Dissolved 19.9 kg of crude (2'-formyl-6-methoxy-4'-trifluoromethyl-biphenyl-3-yl)-acetic acid ethyl ester in 50.0 kg of dicloromethane (DCM). The solution was divided into 8 equal portions of 8.8 kg each. 4.0 kg silica gel was charged to a rotovap flask and 8.8 kg of 1 portion of crude (2'-formyl-6-methoxy-4'-trifluoromethyl-biphenyl-3-yl)-acetic acid ethyl ester solution was charged to the rotovap flask. The solvent was concentrated to dryness. This was repeated for the remaining seven portions of crude (2'-formyl-6-methoxy-4'-trifluoromethyl-biphenyl-3-yl)-acetic acid ethyl ester solution.

Step 3B:

To a clean Nutsche filter, 28.0 kg of silica gel was charged. On top of this silica bed, 25.9 kg of crude (2'-formyl-6-methoxy-4'-trifluoromethyl-biphenyl-3-yl)-acetic acid ethyl ester loaded on silica from Step 3A was spread on the silica bed. The bed was eluted with 35.0 kg hexanes. This was followed by 100.0 kg of hexanes, followed by 151.0 kg 5:95 (v/v) ethyl acetate:hexanes and 819.6 kg 1:9 (v/v) ethyl acetate:hexanes and fractions of 15 to 20 L were collected. The eluates were separated as pure fractions, mixed fractions and waste fractions. This was repeated for two more batches of Step 3B, with the only variation being the amount of 1:9 (v/v) ethyl acetate:hexanes, which was reduced to 511.2-544.6 kg.

Step 3C:

Mixed fractions were concentrated to dryness in rotovap and crystallized in Step 3D. Pure fractions of (2'-formyl-6-methoxy-4'-trifluoromethyl-biphenyl-3-yl)-acetic acid ethyl ester were concentrated to dryness on rotovap to isolate (2'-formyl-6-methoxy-4'-trifluoromethyl-biphenyl-3-yl)-acetic acid ethyl ester, followed by drying under vacuum at 45° C. to constant weight. Yield of (2'-formyl-6-methoxy-4'-trifluoromethyl-biphenyl-3-yl)-acetic acid ethyl ester is 12.2 kg (95.2% pure by liquid chromatography) from this step.

Step 3D:

(Recovery of pure (2'-formyl-6-methoxy-4'-trifluoromethyl-biphenyl-3-yl)-acetic acid ethyl ester from mixed fractions)—To a 22 L multi-neck round bottom flask dissolved 1.5 kg of (2'-formyl-6-methoxy-4'-trifluoromethyl-biphenyl-3-yl)-acetic acid ethyl ester, recovered from mixed fractions, in 4.7 kg 2-propanol (IPA) at 60±5° C. Charged 2.8 kg of water and heated to 65±10° C. until a clear solution was obtained, cooled to 0±5° C. Agitated at this temperature for 15 minutes. Filtered, washed with 1 L of 63:37 (v/v) 2-propanol/water, precooled to 0±5° C. Dried under vacuum at 45° C. to constant weight. Yield of (2'-formyl-6-methoxy-4'-trifluoromethyl-biphenyl-3-yl)-acetic acid ethyl ester is 1.1 kg (97.9% pure by liquid chromatography) from this step.

Step 4:

Charged to a 200 L glass-lined reactor 13.3 kg or (2'-formyl-6-methoxy-4'-trifluoromethyl-biphenyl-3-yl)-acetic acid ethyl ester and 95.0 kg of ethanol. Started agitation and set up a scrubber in line with vapor line of reactor containing 50.0 kg of 2M hydrochloric acid. Using a diaphragm pump, charged slowly 26.5 kg of 2M ethylamine in THF to the reactor. Rinsed charging line with 10.0 kg of ethanol. Agitated the reactor contents at 30±5° C. for a period of 3 hours. Charged to the reactor a total of 4.3 kg of sodium cyanoborohydride in five portions every three hours. After each charge of sodium cyanoborohydride, charged 1.1 kg of acetic acid to the reactor. Stirred for 3 hours. Distilled off the solvent under vacuum at ≤40° C. until the rate of distillation decreased and 105.8 kg of solvent was distilled. Charged 50.0 kg MTBE and cooled the reactor contents to 20° C. Reaction mixture was brought up to a pH of 8 by charging 120.0 kg of 5% sodium bicarbonate solution. Agitated for 10 minutes and separated the layers. The organic layer containing (2'-ethylaminomethyl-6-methoxy-4'-trifluoromethyl-biphenyl-3-yl)-acetic acid ethyl ester was washed with 102.0 kg of 25% sodium chloride solution. The organic layer containing (2'-ethylaminomethyl-6-methoxy-4'-trifluoromethyl-biphenyl-3-yl)-acetic acid ethyl ester was dried over 10.0 kg anhydrous sodium sulfate and concentrated under vacuum at 40° C. until the rate of distillation significantly decreased.

Exchanged solvents into MTBE by charging 70.0 kg MTBE to reactor and distilling the solvent until the rate of distillation significantly decreased. This was repeated once more. Charged 50.0 kg MTBE to reactor. Cooled to 15° C. and charged 11.4 kg of 4M hydrogen chloride in dioxane over a period of 1.1 hours. Rinsed charging line with 1.0 kg MTBE. Agitated at 20° C. for a total of 4.1 hours. Filtered, washed with 2.0 kg of MTBE and dried under vacuum at 45° C. to constant weight over a period of 10.5 hours. Yield of (2'-ethylaminomethyl-6-methoxy-4'-trifluoromethyl-biphenyl-3-yl)-acetic acid ethyl ester, HCl salt is 11.6 kg (95.2% pure by liquid chromatography).

Step 5:

To a 400 L glass-lined reactor, 12.0 kg of (2'-ethylaminomethyl-6-methoxy-4'-trifluoromethyl-biphenyl-3-yl)-acetic acid ethyl ester, HCl salt, 0.2 kg of 4-dimethylaminopyridine (DMAP) and 107.0 kg of tetrahydrofuran was added. Cooled and agitated the reactor contents at internal temperature of 6.8° C. Charged to the reactor 7.1 kg of triethylamine maintaining reactor temperature of ≤10° C. Also charged 0.9 kg of tetrahydrofuran to rinse charging line, followed by 3.9 kg of benzylisocyanate maintaining reactor temperature of ≤10° C. and 1.0 kg of tetrahydrofuran to rinse charging line. The reactor contents were agitated at internal temperature of 20° C. for 1 hour. Upon completion of reaction, the reaction mixture was filtered through a bag filter. The reactor was rinsed with 20.0 kg of tetrahydrofuran and the rinse was also used as the bag filter wash, ultimately charged to the filtered [2'-(3-benzyl-1-ethyl-ureidomethyl)-6-methoxy-4'-trifluoromethyl-biphenyl-3-yl]-acetic acid ethyl ester solution. The solution was then concentrated until the rate of distillation significantly decreased and liquid level was below the agitator. A total of 110.8 kg of solvent were removed at this point. Charged 89.0 kg of MTBE to reactor followed by 125.0 kg 1M of hydrochloric acid. Reactor contents were agitated for 15 minutes at 20±5° C. and the layers separated. The organic layer containing [2'-(3-benzyl-1-ethyl-ureidomethyl)-6-methoxy-4'-trifluoromethyl-biphenyl-3-yl]-acetic acid ethyl ester was dried over 5.0 kg of sodium sulfate, anhydrous, and concentrated to dryness. Yield of [2'-(3-benzyl-1-ethyl-ureidomethyl)-6-methoxy-4'-trifluoromethyl-biphenyl-3-yl]-acetic acid ethyl ester is 14.5 kg (91.4% pure by liquid chromatography). Purification is outlined in steps 5A-5C.

Step 5A:

Dissolved 14.5 kg of crude [2'-(3-benzyl-1-ethyl-ureidomethyl)-6-methoxy-4'-trifluoromethyl-biphenyl-3-yl]-acetic acid ethyl ester in 52.0 kg of ethyl acetate. Split solution into 8 equal portions of 8.3 kg each. 4.0 kg silica gel was charged to a rotovap flask along with 8.3 kg of one portion of crude [2'-(3-benzyl-1-ethyl-ureidomethyl)-6-methoxy-4'-trifluoromethyl-biphenyl-3-yl]-acetic acid ethyl ester solution. The solvent was concentrated to dryness.

Step 5B:

To a clean Nutsche filter was charged 28.0 kg of silica gel. On top of this silica bed, 17.3 kg of crude [2'-(3-benzyl-1-ethyl-ureidomethyl)-6-methoxy-4'-trifluoromethyl-biphenyl-3-yl]-acetic acid ethyl ester loaded on silica from Step 5A was spread on the silica bed. The bed was eluted with 85.0 kg 1:9 (v/v) Ethyl acetate:hexanes followed by 212.2 kg of 15:85 (v/v) ethyl acetate:hexanes and 142 kg of 2:8 (v/v) ethyl acetate:hexanes and 405 kg of 4:6 (v/v) ethyl acetate:hexanes and fractions of 15 to 20 L were collected. The eluates were separated as pure fractions, mixed fractions and waste fractions. This was repeated for two more batches of Step 5B using 19.3 kg and 18.3 crude [2'-(3-benzyl-1-ethyl-ureidomethyl)-6-methoxy-4'-trifluoromethyl-biphenyl-3-yl]-acetic acid ethyl ester loaded on silica.

Mixed fractions from first silica plug were combined and loaded in silica as follows: Dissolved 5.5 kg of crude [2'-(3-benzyl-1-ethyl-ureidomethyl)-6-methoxy-4'-trifluoromethyl-biphenyl-3-yl]-acetic acid ethyl ester in 17.0 kg of ethyl acetate. Split solution into 3 equal portions of 7.5 kg each. 4.0 kg of silica gel was charged to a rotovap flask along with 7.5 kg of one portion of crude [2'-(3-benzyl-1-ethyl-ureidomethyl)-6-methoxy-4'-trifluoromethyl-biphenyl-3-yl]-acetic acid ethyl ester solution. The solvent was concentrated to dryness. This was repeated for the remaining two portions of crude [2'-(3-benzyl-1-ethyl-ureidomethyl)-6-methoxy-4'-trifluoromethyl-biphenyl-3-yl]-acetic acid ethyl ester solution. For this material the elution was performed using the same gradients and volumes as those of the first plug of Step 5B.

Step 5C:

Mixed fractions were combined and concentrated to a minimum volume in a 200 L glass-lined reactor followed by concentration to dryness in a rotovap. Pure fractions of [2'-(3-benzyl-1-ethyl-ureidomethyl)-6-methoxy-4'-trifluoromethyl-biphenyl-3-yl]-acetic acid ethyl ester were concentrated to a minimum volume in a 200 L glass-lined reactor, transferred to rotovaps and concentrated to dryness under vacuum.

Yield of [2'-(3-benzyl-1-ethyl-ureidomethyl)-6-methoxy-4'-trifluoromethyl-biphenyl-3-yl]-acetic acid ethyl ester is 11.3 kg (99.2% pure by liquid chromatography).

Step 6:

Dissolved in rotovap flasks, 11.3 kg of [2'-(3-benzyl-1-ethyl-ureidomethyl)-6-methoxy-4'-trifluoromethyl-biphenyl-3-yl]-acetic acid ethyl ester in 25.0 kg of tetrahydrofuran and 11.0 kg of ethanol. Charged the solution to the 200 L GL reactor followed by the slow addition of 3.6 kg of 50% sodium hydroxide solution over a period of 1.2 hours. Rinsed charging line with 2.0 kg of ethanol. Agitated the reaction mixture at a jacket temperature of 20° C. for a period of 1 hour.

Distilled off solvents under vacuum at an internal temperature of ≤40° C. until 35.8 kg of solvent were removed. Cooled to 20° C. and charged 114.0 kg of water and 44.0 kg of MTBE. Agitated the reactor contents for 10 minutes and separated layers. Charged back the aqueous layer containing Compound 2 and washed with 44.0 kg of MTBE five more times. Rinsed reactor wall with 10.0 kg of MTBE. Charged 4.4 kg of concentrated HCl to acidify reaction mixture to a pH of 2. Charged to the reactor, 84.0 kg of MTBE. Agitated the reactor contents for 10 minutes and separated layers. Charged back the MTBE layer containing Compound 2 and rinsed reactor wall with the same 10.0 kg MTBE used for first reactor rinse, and combined rinse with MTBE/[2'-(3-benzyl-1-ethyl-ureidomethyl)-6-methoxy-4'-trifluoromethyl-biphenyl-3-yl]-acetic acid solution. Dried the solution over 5.0 kg of sodium sulfate, anhydrous. Concentrated the MTBE layer to a minimum volume in the reactor and then transferred into rotovap flasks for concentration to dryness under vacuum at an internal temperature of ≤40° C. Yield is 11.0 kg (99.2% pure by liquid chromatography).

Example 2

Preparation of Compound 2 (Sodium Salt)

Methanol and Compound 1 are mixed to form a solution. An appropriate amount of a 50% sodium hydroxide solution is added and the resulting solution is mixed. When a pH of approximately 9 is achieved, the solution is concentrated to dryness to provide Compound 2. The dried material is dissolved in ethanol and agitated. The solution is concentrated. Compound 2 is charged and slurried with heptane. The contents are filtered and dried to a constant weight. The final API is passed through a 20 mesh screen.

Example 2a

Kilogram Preparation of Compound 2

Dissolved in rotovap flasks 11.0 kg of [2'-(3-benzyl-1-ethyl-ureidomethyl)-6-methoxy-4'-trifluoromethyl-biphenyl-3-yl]-acetic acid in 28.0 kg of methanol. Charged solution to a 200 L GL reactor and began agitation. Rinsed with 4.0 kg of methanol. Set jacket temperature to 15° C. Charged 1.643 kg of 50% sodium hydroxide solution over a period of 30 minutes. Agitated for 20 minutes. At this point pH was 9.4. Split reaction mixture into 6 portions of ~1.5 kg of Compound 2. Charged each portion through a 0.45μ polish filter into rotovaps and concentrated each portion until ~1.5 kg of Compound 2 remained. To each portion charged 5.2 kg of ethanol through a 0.45μ polish filter and concentrated to dryness. Pulled high vacuum until free solids appeared. The solids were charged to a 200 L reactor and charged 51.0 kg of heptane through a polish filter and agitated at 45° C. with no vacuum for 2 hours. Removed 17.4 kg of solvent by vacuum distillation and charged 17.0 kg of heptane. Repeated the heptane cycle one more time and agitated at 40° C. with no vacuum for 8 hours. Filtered, washed with 10.0 kg of heptane. Dried to constant weight under vacuum at 45° C. Dried wet Compound 2 to constant weight under vacuum at ≤50° C. Continued drying at 60° C. to reduce residual ethanol content to <5000 ppm. Yield of Compound 2 is 9.6 kg (98.2% pure by liquid chromatography).

Example 3

Synthesis of Potassium Salt 20 mg of Compound 1 in 100 μl of ethanol was added to one molar equivalent of potassium hydroxide and then heated to 50° C. for approximately 10-12 hours to assist with the dissolution of the base. The solvent was removed to provide the potassium salt of Compound 1.

Example 4

Synthesis of Calcium Salt 20 mg of Compound 1 in 100 μl of ethanol was added to one molar equivalent of calcium hydroxide and then heated to 50° C. for approximately 10-12 hours to assist with the dissolution of the base. The calcium salt of Compound 1 was isolated by filtration under vacuum.

Example 5

Synthesis of L-Arginine Salt 20 mg of Compound 1 in 100 μl of ethanol was added to one molar equivalent of L-arginine potassium hydroxide and then heated to 50° C. for approximately 10-12 hours to assist with the dissolution of the base. The L-arginine salt of Compound 1 was isolated by filtration under vacuum.

Example 6

Synthesis of L-Lysine Salt 20 mg of Compound 1 in 100 μl of ethanol was added to one molar equivalent of L-lysine and then heated to 50° C.

for approximately 10-12 hours to assist with the dissolution of the base. The L-lysine salt of Compound 1 was isolated by filtration under vacuum.

Example 7

Synthesis of Ammonium Salt 20 mg of Compound 1 in 100 μl of ethanol was added to one molar equivalent of ammonium hydroxide and then heated to 50° C. for approximately 10-12 hours to assist with the dissolution of the base. The solvent was removed to provide the ammonium salt of Compound 1.

Example 8

Synthesis of N-Methyl-D-Glucamine Salt 20 mg of Compound 1 in 100 μl of ethanol was added to one molar equivalent of N-methyl-D-glucamine and then heated to 50° C. for approximately 10-12 hours to assist with the dissolution of the base. The solvent was removed to provide the N-methyl-D-glucamine salt of Compound 1.

Example 9

Synthesis of Choline Salt 20 mg of Compound 1 in 100 μl of ethanol was added to one molar equivalent of choline hydroxide and then heated to 50° C. for approximately 10-12 hours to assist with the dissolution of the base. The solvent was removed to provide the choline salt of Compound 1.

Example 10

Water Determination by Karl Fischer Titration (KF)

The water content of each sample was measured on a Mettler Toledo DL39 Coulometer using Hydranal Coulomat AG reagent and an argon purge. Weighed solid samples were introduced into the vessel on a platinum TGA pan which was connected to a subaseal to avoid water ingress. Approx 10 mg of sample was used per titration and duplicate determinations were made.

The content of water in samples of Compound 1 was determined to be less than 5%, less than 4%, less than 3%, less than 2%, or less than 1% by Coulometric Karl Fisher analysis. In one embodiment, samples of Compound 1 were found to include about 1.2% of water.

The content of water in samples of Compound 2 was determined to be less than 10%, less than 8%, less than 7%, less than 6%, less than 5%, less than 4%, less than 3%, less than 2%, or less than 1% by Coulometric Karl Fisher analysis. In one embodiment, samples of Compound 2 were found to include about 5.9% of water.

Example 11

Thermodynamic Aqueous Solubility

Aqueous solubility was determined by suspending sufficient compound in water to give a maximum final concentration of $\geq 10$ mg·ml$^{-1}$ of the parent free-form of the compound. The suspension was equilibrated at 25° C. for 24 hours then the pH was measured. The suspension was then filtered through a glass fibre C filter into a 96 well plate. The filtrate was then diluted by an appropriate factor. Quantitation was by HPLC with reference to a standard solution of approximately 0.1 mg·ml$^{-1}$ in DMSO. Different volumes of the standard, diluted and undiluted sample solutions were injected. The solubility was calculated using the peak areas determined by integration of the peak found at the same retention time as the principal peak in the standard injection.

TABLE 1

| HPLC Method Parameters for Solubility Measurements | |
|---|---|
| Type of method: | Reverse phase with gradient elution |
| Column: | Phenomenex Luna, C18 (2) 5 μm 50 × 4.6 mm |
| Column Temperature (° C.): | 25 |
| Standard Injections (μl): | 1, 2, 3, 5, 7, 10 |
| Test Injections (μl): | 1, 2, 3, 10, 20, 50 |
| Detection: Wavelength, Bandwidth (nm): | 260, 80 |
| Flow Rate (ml · min − 1): | 2 |
| Phase A: | 0.1% TFA in water |
| Phase B: | 0.085% TFA in acetonitrile |

| Timetable | | |
|---|---|---|
| Time (min) | % Phase A | % Phase B |
| 0.0 | 95 | 5 |
| 1.0 | 80 | 20 |
| 2.3 | 5 | 95 |
| 3.3 | 5 | 95 |
| 3.5 | 95 | 5 |
| 4.4 | 95 | 5 |

Analysis was performed on an Agilent HP1100 series system equipped with a diode array detector and using ChemStation software vB.02.01-SR1.

TABLE 2

| Solubility of Various Salts | |
|---|---|
| Compound | Solubility |
| Compound 1 | 0.21 mg/mL at pH 6.1 |
| Compound 2 | ≥10 mg/mL at pH 8.9 |
| Compound 1, arginine salt | 46 mg/mL at pH 8.57 |
| Compound 1, lysine salt | ≥50 mg/mL at pH 7.53 |

Example 12

Solubility Profiling at Various pHs

The aqueous solubility was determined using the method described in Table 1. The pH was varied by the suspensions being made up in 0.15 M NaCl (aq) and the pH adjusted to the appropriate value with either dilute HCl or NaOH. The suspension was then allowed to equilibrate for two hours followed by checking the pH and readjustment if required, using either HCl or NaOH as appropriate. The suspension was then allowed to equilibrate for 24 hrs.

TABLE 3 pH solubility profile of Compound 1

| Media | Volume of Media (mL) | Original pH | Final pH | Appearance | Solubility (mg/mL) |
|---|---|---|---|---|---|
| pH 1 | 0.619 | 1.15 | 1.15 | Solid on surface | 0.0069 |
| pH 2 | 0.290 | 2.0 | 2.0 | Residual solid | 0.0016 |
| pH 3 | 0.289 | 3.01 | 3.1 | Residual solid | 0.0022 |
| pH 4 | 0.297 | 3.97 | 4.22 | Residual solid | 0.0035 |
| pH 5 | 0.255 | 5.0 | 5.07 | Residual solid | 0.053 |
| pH 6 | 0.267 | 6.02 | 5.60 | Residual solid | 0.16 |
| pH 7 | 0.258 | 7.03 | 6.47 | Residual solid | 0.59 |
| pH 8 | 0.273 | 8.09 | 7.07 | Suspension | 2.2 |

Example 13

Chemical Purity Determination

Purity analysis was performed by HPLC on an Agilent HP1100 series system equipped with a diode array detector and using ChemStation software vB.02.01-SR1.

TABLE 4

HPLC Method Parameters for Chemical Purity Determinations

| | |
|---|---|
| Sample Preparation: | 0.4-1.4 mg/ml in acetonitrile:water 1:1 v/v |
| Column: | Phenomenex Luna C18 (2), 150 × 4.6 mm, 5 μm |
| Column Temperature (° C.): | 25 |
| Injection (μl): | 5 |
| Detection: Wavelength, Bandwidth( nm): | 255, 90 |
| Flow Rate (ml · min − 1): | 1 |
| Phase A: | 0.1%TFA in water |
| Phase B: | 0.085% TFA in acetonitrile |

Timetable:

| Time (min) | % Phase A | % Phase B |
|---|---|---|
| 0 | 95 | 5 |
| 25 | 5 | 95 |
| 25.2 | 95 | 5 |
| 30 | 95 | 5 |

Samples of Compound 1 and Compound 2 were found to be greater than 90% pure. In some embodiments, samples of Compound 1 were found to be greater than 95% pure, greater than 96% pure, greater than 97% pure, greater than 98% pure, greater than 99% pure, greater than 99.5% pure. In some embodiments, samples of Compound 2 were found to be greater than 94% pure, greater than 95% pure, greater than 96% pure, greater than 97% pure, greater than 98% pure, greater than 99% pure.

Residual Solvents

The test for Residual Solvents is performed to detect trace amounts of solvents used in the synthesis that may be present in the API. The analysis is performed via headspace or direct injection analysis using a gas chromatograph equipped with a flame ionization detector (FID). All residual solvents used in the synthesis are capable of being detected by this method.

Potential residual solvents include acetone, ethanol, methanol, dichloromethane, methyl-tert-butyl-ether (MTBE), ethyl acetate, tetrahydrofuran, heptane, hexane, n-methylpyrrolidinone (NMP), acetic acid.

TABLE 10

Residual Solvents by GC Headspace

| Residual Solvent | Amount (ppm) |
|---|---|
| Acetone | ≤5000 ppm |
| ethanol | ≤5000 ppm |
| methanol | ≤3000 ppm |
| MTBE | ≤5000 ppm |
| THF | ≤720 ppm |
| heptane | ≤5000 ppm |
| Ethyl acetate | ≤5000 ppm |
| hexane | ≤290 ppm |
| dichloromethane | ≤600 ppm |
| 1,4-dioxane | ≤380 ppm |
| NMP | ≤530 ppm |
| Acetic Acid | ≤5000 ppm |

Example 14

Heavy Metals (Pd) by ICP-AES

Trace palladium (Pd) resulting from the use of catalytic amounts of Pd in the synthesis is assayed by inductively coupled plasma atomic emission spectrometry (ICP-AES). Pd content by ICP-AES is a detectable amount of palladium that is less than about 20 ppm. Pd content by ICP-AES is less than about 20 ppm. Pd content by ICP-AES is a detectable amount of palladium that is less than 20 ppm, less than 15 ppm, less than 10 ppm, less than 9 ppm, less than 8 ppm, less than 7 ppm, less than 6 ppm, or less than 5 ppm. Pd content by ICP-AES is less than 20 ppm, less than 15 ppm, less than 10 ppm, less than 9 ppm, less than 8 ppm, less than 7 ppm, less than 6 ppm, or less than 5 ppm. Pd content by ICP-AES is about 10 ppm, about 6 ppm, about 5 ppm, about 4 ppm, about 3 ppm, about 2 ppm, or about 1 ppm. In one aspect, samples or pharmaceutical compositions do not include a detectable amount of palladium.

Example 15

Heavy Metals (as Lead)

This test is performed according to USP<231>Method II.
Pharmaceutical Compositions Pharmaceutical compositions that include Compound 1, including pharmaceutically acceptable salts (e.g. Compound 2) and/or pharmaceutically acceptable solvates thereof include a variety of forms. In one aspect, pharmaceutical compositions are in the form of oral dosage forms. In some embodiments, the oral dosage forms are formulated as: oral solutions, oral suspensions, tablets, pills, or capsules.

Example 16

Oral Solutions

In one aspect, an oral pharmaceutical composition in the form of an oral solution is prepared as outlined below.

Although a 1 L batch size is shown with a 0.015 mg/mL or a 20 mg/mL concentration of Compound 2, other batch sizes and concentrations are contemplated.

TABLE 5

0.015 mg/mL Oral Solution (1 L Batch Size)

| Components | w/w (%) | Amount (mg) per mL | Amount per Batch (g) |
|---|---|---|---|
| Compound 2 | 0.0015 | 0.015 | 0.015 |
| Anhydrous Sodium Carbonate, USP | 0.1 | 1.06 | 1.06 |
| Labrasol, NF | 5.0 | 50 | 50 |
| Orange Oil, FCC | 0.5 | 5 | 5 |
| Sucralose, FCC | 0.5 | 5 | 5 |
| Purified Water, USP, q.s. to | 100 | 1.0 mL | 1.0 L |

TABLE 6

20 mg/mL Oral Solution (1 L Batch Size)

| Components | w/w (%) | Amount (mg) per mL | Amount per Batch (g) |
|---|---|---|---|
| Compound 2 | 2.0 | 20 | 20 |
| Anhydrous Sodium Carbonate, USP | 0.1 | 1.06 | 1.06 |
| Labrasol, NF | 5.0 | 50 | 50 |
| Orange Oil, FCC | 0.5 | 5 | 5 |
| Sucralose, FCC | 0.5 | 5 | 5 |
| Purified Water, USP, q.s. to | 100 | 1.0 mL | 1.0 L |

The manufacturing process for the solutions of Compound 2 described above is as follows: Weigh the required amount of sodium carbonate and transfer to the container. Add the required amount of water and mix until dissolved. Weigh the required amount of Labrasol and add this to the solution and mix until homogenous. Weigh the required amount of orange oil and add this to the solution and mix until homogenous. Weigh the required amount of sucralose and add this to the solution and mix until dissolved. The above prepared solution is considered a placebo solution. Add the required amount of placebo solution into a separate container. Weigh the required amount of Compound 2 and slowly add to the placebo solution. Mix for a minimum of 3 hours until all Compound 2 is dissolved (sonicate, warm, or stir if necessary). Compound 2 may dissolve in a shorter period, however the minimum mix time is needed for reproducibility.

In one aspect, 20 mL of the bulk solution is dispensed in a plastic syringe. The prepared solutions are stored in the refrigerator at approximately 2°-8° C. for up to 24 hours.

Example 17

Immediate Release Tablets

Immediate release tablets were prepared that included either 10 mg of Compound 2 or 30 mg of Compound 2. Other dose amounts were prepares and tested. In some cases, the tablets were coated with a thin film as described below.

The manufacturing process includes blending, compression and coating. The following excipients including Parteck M 200, Prosolv SMCC HD 90, Crospovidone XL, Pruv, Spress B820, Avicel PH 102, Ac-Di-Sol, Magnesium Stearate, and Opadry II, 85F18422 white have been used for manufacturing. Manufacturing/analytical equipment included: formulation (U.S.A. standard testing sieve; V-shell blender; ERWEKA TBH300 MD hardness tester; Vanderkamp friability tester; Manesty beta press, sixteen station); analytical (Agilent 1100 series HPLC with variable wavelength detector; VanKel model VK7000 dissolution apparatus; VanKel model VK8000 dissolution autosampler).

TABLE 7

Immediate Release Tablets

| | 10 mg Coated Tablets | | 10 mg Uncoated Tablets | 30 mg Coated Tablets | | 30 mg Uncoated Tablets |
|---|---|---|---|---|---|---|
| | mg/tablet | | | | | |
| Compound 2 | 10.2 | 10.2 | 10.2 | 30.6 | 30.6 | 30.6 |
| Parteck M 200 (Mannitol) | 111.0 | | 111.0 | 102.6 | | 102.6 |
| Prosolv HD 90 (silicified microcrystalline cellulose) | 166.8 | | 166.8 | 154.8 | | 154.8 |
| Crospovidone XL (cross linked polyvinylpyrollidone) | 9.0 | | 9.0 | 9.0 | | 9.0 |
| Pruv (sodium stearyl fumarate) | 3.0 | | 3.0 | 3.0 | | 3.0 |
| Spress B820 (pregelatinized starch) | | 55.6 | | | 51.2 | |
| Avicel PH 102 (microcrystalline cellulose) | | 223.1 | | | 207.1 | |
| Ac-Di-Sol (croscarmellose sodium) | | 9.0 | | | 9.0 | |
| Magnesium stearate | | 2.1 | | | 2.1 | |
| Opadry II, 85F18422 white | 12.0 | 12.0 | | 12.0 | 12.0 | |
| total | 312.0 | 312.0 | 300.0 | 312.0 | 312.0 | 300.0 |

Method of Manufacture of Immediate Release Tablets

Blending: Screen all excipients (except lubricant) through 30 mesh. Screen Compound 2 through 60 mesh (for 10 mg dosage) or 40 mesh (for 30 mg dosage). Mix in a V-shell blender for 15 minutes. Screen lubricant through 60 mesh, add into V-shell blender and blend for 2 minutes.

Tableting: Tablet cores were all compressed to a target weight of 300 mg (±5%) on a Manesty Betapress sixteen station with two sets of ⅜" round standard concave tooling. During compression, individual and average tablet weight, hardness, thickness, and friability were monitored.

Coating: 15% (w/w) Opadry II white suspension was prepared by suspending 30 g of Opadry II white in 200 g of purified water with an overhead stirrer. The suspension was stirred for 45 minutes and then passed through 60 mesh screen before using for coating. The suspension was stirred gently by a stir bar and magnetic plate during coating.

Approximately 525 g core tablets were pre-heated at working exhaust temperature (38-43° C.) in a Vector LDCS5 pan coater by jogging the coating pan for 5-10 minutes. Average weight of ten tablets was measured. 15% (w/w) Opadry II white suspension was slowly coated onto core tablets to gain approximately 4% mass of coating. In-process coating parameters were recorded. Average tablet weight was monitored with an interval of 10-15 minutes after 1 hour of coating. Once target weight gain was attained, coating was stopped. Coated tablets were dried by jogging the coating pan for 10 minutes.

Dissolution Results

All cores and coated tablets were tested for dissolution using the following parameters:

| Dissolution Parameters | |
|---|---|
| Apparatus: | USP2 Paddles |
| Speed: | 50 rpm |
| Dissolution Media: | $KH_2PO_4$ buffer, 0.05M, pH 6.8 |
| Dissolution volume: | 900 mL |
| Medium temperature: | 37 ± 0.5° C. |
| Sampling volume: | 1.5 mL |

Based on the testing, all the formulations described in Table 7 showed immediate release profiles, and met the proposed specification of no less than (NLT) 80% released in 10 minutes.

The tablets were packaged in 40 count in 50 cc HDPE bottles, with CRC caps and heat induction seal. At one month and three months, all tablets showed stability data at 25° C./60% RH and 40° C./60% RH within acceptable ranges.

Example 18

Sustained Release Tablets

The blend of the formulation is prepared in the same manner as the immediate release tablets (e.g. sieving, blending, and compression). Other preparations are acceptable, such as wet granulation, fluidized bed, high shear granulation, etc. The formulation includes drug modifying release excipients. These excipients include but not limited to HPMC (hydroxy propyl methylcellulose or hypromellose), methacrylic polymers, polyvinyl acetate, and povidone. The amount of drug release modifying excipient ranges from about 10% to about 80% in the formulation. The drug release profile ranges from 0 to 4 hours, 0 to 6 hours, 0 to 8 hours, 0 to 12 hours, 0 to 24 hours, 2 to 4 hours, 2 to 6 hours, etc. In some embodiments, the formulations are coated with the Opadry coatings after direct compression. Example sustained release formulations are listed below.

TABLE 8

| Sustained Release Tablet | | | |
|---|---|---|---|
| | Amount per tablet (mg) | %, w/w | Batch Size (g) |
| Compound 2 | 30 | 10 | 10 |
| Prosolv HD 90 | 198 | 66 | 66 |
| METHOCEL K4M[1] | 60 | 20 | 20 |

TABLE 8-continued

| Sustained Release Tablet | | | |
|---|---|---|---|
| | Amount per tablet (mg) | %, w/w | Batch Size (g) |
| Crospovidone XL | 9 | 3 | 3 |
| Sodium Stearyl Fumarate | 3 | 1 | 1 |
| Total | 300 | 100 | 100 |

[1]—hydroxypropyl methyl cellulose, supplied by DOW Chemical

TABLE 9

| Sustained Release Tablet | | | |
|---|---|---|---|
| | Amount per tablet (mg) | %, w/w | Batch Size (g) |
| Compound 2 | 30 | 10 | 10 |
| Lactose | 156 | 52 | 52 |
| METHOCEL K4M[1] | 105 | 35 | 35 |
| Crospovidone XL | 6 | 2 | 2 |
| Magnesium Stearate | 3 | 1 | 1 |
| Total | 300 | 100.0 | 100 |

[1]—hydroxypropyl methyl cellulose, supplied by DOW Chemical

TABLE 10

| Sustained Release Tablet | | | |
|---|---|---|---|
| | Amount per tablet (mg) | %, w/w | Batch Size (g) |
| Compound 2 | 30 | 10 | 10 |
| Microcystalline cellulose | 141 | 47 | 47 |
| METHOCEL K4M[1] | 60 | 20 | 20 |
| METHOCEL K100M[1] | 60 | 20 | 20 |
| Crosscarmellose Sodium | 6 | 2 | 2 |
| Magnesium Stearate | 3 | 1 | 1 |
| Total | 300 | 100 | 100 |

[1]—hydroxypropyl methyl cellulose, supplied by DOW Chemical

Example 19

Enteric Coated Tablets

Enteric coated tablets were prepared with the ingredients listed in Table 11.

TABLE 11

| Enteric Coated tablets | | | |
|---|---|---|---|
| | Tablet #1 | Tablet #2 | Tablet #3 |
| Ingredient | Amount per Tablet | | |
| Compound 2 immediate release tablet 30 mg | 312.0 | 312.0 | 312.0 |
| Eudragit L 100-55 | 18.7 | | |
| Eudragit S 100 | | 18.7 | |
| Eudragit L 100 | | | 18.7 |
| Triethyl Citrate | 2.8 | 2.8 | 2.8 |
| Acetone | | | |
| Purified Water | | | |
| Total | 333.5 | 333.5 | 333.5 |

The preparation of the enteric coated tablets is as follows: Weigh 388.0 g of acetone and 12.0 g of purified water and mix them in a beaker with an overhead stirrer. Weigh 40 g of the Eudragit and pour into the solvent mixture slowly in portions to prevent lump formation. Stir until a clear solution is made. Then weigh 6 g of triethyl citrate and add into the clear solution and keep stirring until a homogeneous solution is made. Mix around 500 g of placebo tablets with about 80 of the 30 mg immediate release tablets and coat with the coating mixture.

Canine studies using the formulations described herein showed that the absorption profile can be modified by using the different formulations. Canine studies showed that Compound 2 is rapidly absorbed in the stomach and upper gastrointestinal tract. The Tmax can be delayed by the use of enteric coated tablets.

Example 20

Identification of Metabolic Pathways

The metabolic profile of Compound 1 was investigated using: (1) rat, dog, and human liver microsomes; (2) rat and human hepatocytes; (3) bile collected from rats; and (4) rat and dog plasma after dosing.

Materials

Male Sprague-Dawley rat, male beagle dog, and mixed pool human liver microsomes were purchased from Xenotech (Kansas City, Mo.). Rat and human hepatocytes and InVitroGRO HI medium were purchased from In Vitro Technologies (Gaithersburg, Md.).

Microsomes

To determine the qualitative metabolic profile, 30 μM of Compound 1 was incubated aerobically with rat, dog, or human liver microsomes (1 mg/mL). The incubations were performed in phosphate buffer at pH7.4, 37° C., with the reaction initiated by the addition of 13-NADPH and UDPGA (1 mM and 3 mM final concentration, respectively). The reaction was terminated by the addition of an equal volume of acetonitrile with 1.5% acetic acid after 60 min. The sample was centrifuged and the supernatant was transferred for LC/MS analysis.

Hepatocytes

Rat, dog or human hepatocytes were thawed according to the supplier's instructions. Cells were counted using the Trypan Blue method, and then diluted to $1 \times 10^6$ viable cells/ml with KB medium. Compound 1 was tested at 30 μM and incubated for up to 2 hours in rat hepatocytes and 4 hours in human hepatocytes at 37° C. Fresh human hepatocytes were from a single male donor lot Hu0778 (CellsDirect, Raleigh, N.C.). Reactions were terminated with addition of an equal volume of acetonitrile with 1.5% acetic acid, centrifuged, and supernatants were transferred for LC-MS/MS analysis.

Rat Bile Duct Cannulation

Rats with surgically placed bile duct and jugular vein cannula were purchased from Charles River Laboratories and allowed to acclimate for 2 days. Compound 1 was intravenously dosed (2 mg/kg) to three rats as a solution in 0.9% saline (2 mg/mL; 1 mL/kg). Bile was collected at time-points 0-2, 2-5, 5-8, and 8-24 hrs post-dose in 8 mL scintillation vials and stored at −40° C. until LC-MS/MS analysis. Urine was collected at time points 0-4, 4-8 and 8-24 hrs post-dose in 5 mL scintillation vials and stored at −40° C. until analysis by LC-MS/MS.

LC-MS Analysis

Analyses were performed using a Waters YMC ODS-AQ column (2.1×150 mm; 3 μm) linked to a Shimadzu LC-10AD VP with SCL-10A VP system controller. Tandem mass spectrometric (MS/MS) detection was carried out on a Sciex ABI3200 QTrap in the positive ion mode (ESI) by multiple reaction monitoring, precursor ion scan, and enhanced product ion scan. The mobile phases contained 10 mM ammonium acetate in water with 0.05% formic acid (solvent A) and 10 mM ammonium acetate in 50% acetonitrile/50% methanol with 0.05% formic acid (solvent B). The flow rate was maintained at 0.25 mL/min and the total run time was 65 min. Analytes were separated using a linear gradient as follows:

1. Mobile phase was held for 5 min at 5% B,
2. B was increased from 5% to 95% over then next 50 min,
3. B was held constant for 5 min at 95%, and
4. B was returned to the initial gradient conditions.

For metabolite quantification, the same analysis was performed as above, but the flow rate was maintained at 0.25 mL/min and the total run time was 18 min. Analytes were separated using a linear gradient as follows:

1. mobile phase was held for 3 min at 5% B,
2. B was increased from 5% to 95% over then next 2 min,
3. B was held constant for 9 min at 95%, and
4. B was returned to the initial gradient conditions.

Results

Compound 1 was incubated in rat, dog, and human liver microsomes fortified with 13-NADPH and UDPGA. Metabolites of Compound 1 include: including an amine (M1; 2-(2'-((ethylamino)methyl)-6-methoxy-4'-(trifluoromethyl)biphenyl-3-yl)acetic acid), acyl-glucuronide (M2), de-benzylation (M3; [2'-(1-ethyl-ureidomethyl)-6-methoxy-4'-trifluoromethyl-biphenyl-3-yl]-acetic acid) and several hydroxlation products, N-de-ethylation (M6; [2'-(3-benzyl-ureidomethyl)-6-methoxy-4'-trifluoromethyl-biphenyl-3-yl]-acetic acid) and O-de-methylation (M8; [2'-(3-benzyl-1-ethyl-ureidomethyl)-6-hydroxy-4'-trifluoromethyl-biphenyl-3-yl]-acetic acid). Rat microsomes formed M9 (dehydrogenation; 2-(2'-((3-benzylidene-1-ethylureido) methyl)-6-methoxy-4'-(trifluoromethyl)biphenyl-3-yl)acetic acid), and this metabolite was not seen in dog or human microsomes. Rat, dog and human cryopreserved hepatocytes incubated with Compound 1 provided a similar metabolite profile as microsomes, although M9 is not observed in rat hepatocytes.

In vitro studies: metabolites were semi-quantitatively measured using peak area of the parent (Compound 1). Microsomes formed metabolites to a greater extent compared to hepatocytes and the rank order in vitro between microsomes and hepatocytes in all species appears similar with M5 (a mixture of hydroxylated products of Compound 1) being the most abundant metabolite formed in microsomes while it is the second most abundant in hepatocytes. Hepatocytes generate the acyl-glucuronide (M2) to the greatest extent in cryopreserved rat and fresh and cryopreserved human hepatocytes. Dog cryopreserved hepatocytes generated M1, M3, M5 and M6 to a similar extent (<0.2% of the parent).

Samples taken from rat bile exhibit metabolites consistent with those observed in rat microsomes, with an additional metabolite (M11) observed and identified as the glucuronide of M9. Metabolites were semi-quantitatively measured using peak area of the parent (Compound 1), and the glucuronide is the dominant metabolite (273% of parent), while all others are less than 30% of parent. In rat urine, only M1 was observed.

In plasma taken from rat and dog following oral dosing with Compound 1 for pharmacokinetic studies (10 mg/kg in rat, 5 mg/kg in dog), metabolites were quanified (expressed as area under the curve (AUC). In rat plasma, the glucuronide (M2), de-benzyl (M3), and de-ethyl (M6) are greater than 10% of parent AUC, while in dog plasma the glucuronide (M2) and de-ethyl (M6) are greater than 10% of parent AUC.

Compound 1 metabolites formed during incubation of Compound 1 with with rat, dog, and human liver microsomes, rat and human hepatocytes, as well as those generated in vivo and isolated from rat bile and rat and dog plasma have been investigated. Authentic standards of the majority of the metabolites have been chemically synthesized. The identity of the in vitro and in vivo metabolites were confirmed by comparison with the authentic standard and/or by the fragmentation pattern observed following LC-MS/MS analysis. The major metabolites generated in vitro appear to be an acyl-glucuronide, de-benzylation, hydroxylation and N-de-ethylation. Following intravenous dosing of Compound 1, the major metabolites isolated from rat bile are an acyl-glucuronide, de-benzylation, N-de-ethylation, and O-de-methylation. In urine from these animals, the only metabolite found was the free amine. Metabolites circulating in rat plasma are the glucuronide, de-benzylation, and N-de-ethylation metabolites and all are greater than 10% of the parent AUC in rat. In dog plasma the major metabolites are the acyl-glucuronide and N-de-ethylation with both being greater than 10% parent AUC. All other metabolites in rat and dog plasmas appear to be 5% parent AUC.

Example 21

Extracellular Cytochrome P450 Inhibition

To investigate whether Compound 2 would likely cause any drug-drug interactions, microsomes were incubated test substrates, which were known to be metabolized by CYP enzymes, with or without Compound 2.

Specific aspects of the incubation conditions for each assay (e.g., protein concentration, incubation time, etc.) are defined in Walsky & Obach, 2004 (Walsky, R. L., and Obach, R. S. Validated assays for human Cytochrome P450 activities. *Drug Met. Disp.* 32:647-660, 2004.). In general, microsomes at protein concentrations as defined in Table 12 were mixed with buffer (100 mM $KH_2PO_4$, pH 7.4), $MgCl_2$ (6 mM)) and substrate, and were kept on ice. Aliquots of this mixture (89 µL) were delivered to each well of a 96-well polypropylene plate which contained an aliquot of inhibitor (1 µL) in acetonitrile:water (1:1). Final solvent concentrations were less than 1% (v/v). Incubations were initiated with the addition of 10 µL β-NADPH (10 mM stock) to a final volume of 100 µL. Incubations were terminated by the addition of 1.5-2× volume of acetonitrile containing internal standard (buspirone). Samples were centrifuged at 4° C., and supernatant was transferred for LC-MS/MS analysis.

The results are presented in Table 12.

TABLE 12

Lack of Extracellular Cytochrome P450 Inhibition

| Cytochrome P450 Enzyme | CYP Reaction | Compound 2 $IC_{50}$ (µM) | Inhibitor Control ($IC_{50}$ (µM)) |
|---|---|---|---|
| 3A4 | testosterone 6β-hydroxylation | >50 | Ketoconazole (0.02) |

TABLE 12-continued

Lack of Extracellular Cytochrome P450 Inhibition

| Cytochrome P450 Enzyme | CYP Reaction | Compound 2 $IC_{50}$ (µM) | Inhibitor Control ($IC_{50}$ (µM)) |
|---|---|---|---|
| 3A4 | midazolam 1-hydroxylation | 40 | Ketoconazole (0.02) |
| 2C9 | diclofenac 4'-hydroxylation | >50 | Sulfaphenazole (0.17) |
| 2C19 | mephenytoin 4'-hydroxylation | >50 | (-)-N-3-benzyl-phenobarbital (1.2) |
| 2D6 | dextromethorphan O-demethylation | >50 | Quinidine (0.03) |
| 1A2 | phenacetin O-deethylation | >50 | Furafylline (2.5) |

Compound 2 was not an inhibitor of P450 (CYP) enzymes according to conversion of substrates to known metabolites with and without Compound 2 in the incubation. No apparent inhibition is observed at concentrations up to and exceeding 40 µM for CYP3A4, 1A2, 2C9, 2C19, and 2D6 enzymes.

Example 22

Lack of Cellular Cytochrome P450 Induction

Compound 1 was not an inducer of P450 CYP3A4 or CYP2C9 in cryopreserved human hepatocytes, according to conversion of substrates to known metabolites with and without Compound 1 in the incubation. Briefly, cryopreserved human hepatocytes thawed and plated according to the manufacturer's instructions (In Vitro Technologies, Gathersburg, Md.). The cells were warmed and then poured into pre-warmed InVitroGRO CP medium, gently resuspended, and then the cells were counted using Trypan Blue exclusion. Cells were then diluted to $0.7 \times 10^{-6}$ viable cells/ml with CP medium. Each well received 0.2 ml of the viable cell mixture. The plate was gently shaken to disperse the cells evenly in the well, and the plate was incubated at 37° C., 5% carbon dioxide. At 24 hrs, medium was replaced with fresh CP medium. After 48 hrs, CP medium is replaced with HI medium containing Compound 1 tested at 10 µM, and the positive control, rifampicin was tested at 25 µM. Medium was replaced with fresh medium plus test article 24 hrs later. At 48 hrs, midazolam (50 µM) and diclofenac (50 µM) were incubated in 0.15 mL of K—H buffer for 4 hrs. Reactions were terminated with addition of 0.15 mL of acetonitrile containing internal standard (buspirone), material centrifuged, and supernatants were transferred for LC-MS analysis.

Rifampicin produced an 11-fold increase in 1-hydroxymidazolam (CYP3A4) and 1.6-fold increase in 4-hydroxydiclofenac (CYP2C9) production in hepatocytes when compared to native cells, while Compound 1 produced a 2.7-fold increase in 1-hydroxymidazolam and 1.1-fold increase in 4-hydroxydiclofenac. These data indicate that Compound 1 is not a strong inducer of CYP3A4 or CYP2C9 in human hepatocytes when tested at a concentration of 10 µM. (U.S. FDA Guidance for Industry, "Drug Interaction Studies—Study Design, Data Analysis, and Implications for Dosing and Labeling", September 2006).

Example 23

In Vitro $DP_2$/CRTH2 Binding Assay

The ability of Compound 1 to bind to the human $DP_2$ receptor was assessed via a radioligand binding assay using

[³H]PGD₂. HEK293 cells stably expressing recombinant human DP₂ are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol to approximately 5 mg protein/ml. Membranes (2-10 μg protein/well) are incubated in 96-well plates with 1 nM [³H] PGD₂ and Compound 1 in Assay Buffer (50 mM Hepes, 10 mM MnCl₂, 1 mM EDTA, plus or minus 0.2% human serum albumin, pH 7.4) for 60 minutes at room temperature. The reactions are terminated by rapid filtration through Whatman GF/C glass fibre filter plates. The filter plates were pre-soaked in 0.33% polythylenimine for 30 minutes at room temperature then washed in Wash Buffer (50 mM Hepes, 0.5 M NaCl pH 7.4) prior to harvesting. After harvesting, the filter plates are washed 3 times with 1 ml cold Wash Buffer then dried. Scintillant is then added to the plates and the radioactivity retained on the filters is determined on a Packard TopCount (Perkin Elmer). Specific binding is determined as total radioactive binding minus non-specific binding in the presence of 10 μM PGD₂. $IC_{50}$s were determined using GraphPad prism analysis of drug titration curves. Mouse, rat and guinea pig DP2 receptors were also investigated.

Using radioligand membrane binding experiments, Compound 1 was shown to bind with high affinity to DP2. Compound 1 showed potent inhibition of radiolabeled PGD₂ binding to mouse, rat, guinea pig and human DP2 with average $IC_{50}$ values of 7.8 nM, 10.4 nM, 4.9 nM and 4.9 nM, respectively.

Example 24

In Vitro GTPγS Binding Assay

The ability of Compound 1 to inhibit binding of GTP to DP₂ is assessed via a membrane GTPγS assay. CHO cells stably expressing the recombinant human CRTH2 receptor are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol. Membranes (~12.5 μg per well) are incubated in 96-well plates with 0.05 nM [³⁵S]-GTPγS, 80 nM PGD₂, 5 μM GDP, and Compound 1 in Assay Buffer (50 mM Hepes, pH 7.4, 100 mM NaCl, 5 mM MgCl₂ and 0.2% human serum albumin) for 60 minutes at 30° C. The reactions are terminated by rapid filtration through Whatman GF/B glass fibre filter plates. The filter plates are washed 3 times with 1 ml cold Assay Buffer and dried. Scintillant is then added to the plates and the radioactivity retained on the filters is determined on a Packard TopCount (Perkin Elmer). Specific binding is determined as total radioactive binding minus non-specific binding in the absence of the ligand (80 nM PGD₂). $IC_{50}$s were determined using Graphpad prism analysis of drug titration curves. Compound 1 had an $IC_{50}$ of less than 20 nM in this assay.

Example 25

In Vitro Whole Blood Esoinophil Shape Change Assay

Compound 1 was evaluated in a whole blood assay of eosinophil shape change (ESC) to determine the ability of Compound 1 to antagonize a PGD₂-stimulated functional response in the context of whole blood.

Blood is drawn from consenting human volunteers in EDTA vacutainer tubes and used within 1 hr of draw. A 98 μl aliquot of blood is mixed with 2 μl of Compound 1 (in 50% DMSO) in 1.2 ml polypropylene tubes. The blood is vortexed and incubated at 37° C. for 5 minutes. 5 μl of 1 μM PGD₂ in PBS is added for a final concentration of 50 nM and the tubes briefly vortexed. The reactions are incubated for exactly 5 minutes at 37° C. and then terminated by placing the tubes on ice and immediately adding 250 μl of ice-cold 1:4 diluted Cytofix (BD Biosciences). The reactions are transferred to 12×75 mM polystyrene round bottom tubes and the red blood cells lysed by the addition of 3 ml ammonium chloride lysing solution (150 mM NH₄Cl, 10 mM KHCO₃, 0.1 mM EDTA disodium salt) and incubation at room temperature for 15 minutes. The cells are pelleted by spinning at 1300 rpm for 5 minutes at 4° C. and washed once with 3 ml ice-cold PBS. The cells are resuspended in 0.2 ml of ice-cold 1:4 diluted Cytofix (BD Biosciences) and analyzed on a FACSCalibur (BD Biosciences) within 2 hours. Eosinophils were gated on the basis of autofluorescence in the FL2 channel and shape change on 500 eosinophils was assayed by forward scatter and side scatter analysis. The specific change in shape induced by PGD₂ was calculated as the difference between the percentage of high forward scatter eosinophils in the presence and absence of PGD₂. $IC_{50}$s were determined using Graphpad Prism® analysis of drug titration curves.

Compound 1 showed potent antagonism of DP₂ receptor activation in human and guinea pig whole blood. Compound 1 inhibited PGD₂-induced eosinophil shape change in human and guinea pig whole blood with average $IC_{50}$ values of 2.7 nM and 21.5 nM.

The potency of Compound 1 in the human ESC assay ($IC_{50}$ of 2.7 nM and $IC_{90}$ of 7.5 nM) is relevant to clinical efficacy in asthmatics since eosinophil activation requires initial shape change and because eosinophil mediated damage has been correlated with severe exacerbations of asthma (Wardlaw, A. J., et al., 2002, *Clin. Sci.* 103:201-211).

Example 26

Mouse Allergic Rhinitis Model

Compound 2 was evaluated in a mouse model of ovalbumin (OVA)-induced allergic rhinitis in which nasal ovalbumin challenges to OVA-primed mice elicits an increase in sneezing and nasal rubs (Methods were adapted from those detailed in Nakaya, M., et al. 2006, *Laboratory Investigation*, 86:917-926). OVA-primed mice received an intranasal challenge of OVA daily for 5 consecutive days. On days 1, 3 and 5 of this OVA challenge phase the number of sneezes and nasal rubs were recorded during 8 minute sessions. Daily administration of Compound 2 at a dose of 10 mg/kg PO significantly reduced sneezing behavior. A trend toward a decrease in nasal rubs was observed. Plasma concentrations of Compound 1 taken from a separate group were 280 nM, 150 nM, 70 nM, 30 nM and <8 nM for sampling times 1 hr, 2 hr, 4 hr, 8 hr and 24 hour post-dose, respectively. In radioligand membrane binding experiments from cells expressing the mouse DP₂ receptor, Compound 1 had an $IC_{50}$ of 20.1 nM in the presence of 0.2% mouse serum albumin. Together, these results indicate that in the setting of mouse allergic rhinitis, Compound 1 or a pharmaceutically acceptable salt thereof (e.g. Compound 2) improves nasal symptoms.

Example 27

Guinea Pig IV-DKPGD$_2$-Induced Peripheral Blood Leukocyte Influx

Compound 2's ability to inhibit leukocyte migration in vivo was assessed using intravenous injection of 13,14-dihydro-15-keto-prostaglandin D2 (DK-PGD$_2$). Methods were adapted from those detailed Shichijo et al., 2003, *Journal of Pharmacology and Experimental Therapeutics*, 307:518-525. Male Hartley guinea pigs were immunized with ovalbumin (OVA) on day 0 by intraperitoneal (IP) injection of 1 ml of a 100 µg/ml solution in Imject Alum. They were then used in the DK-PGD$_2$ procedure between days 14 and 21. Subjects were randomly assigned to receive either vehicle (0.5% methyl cellulose, 4 ml/kg, oral (PO)) or one of three to four doses of test compound. Two hours or eighteen hours after dosing, animals were anesthetized with ketamine and challenged with DK-PGD$_2$ (1 mg/kg, IV). Thirty minutes after IV administration, blood was collected via the marginal ear vein into EDTA tubes for cell analysis. 10 µl blood was lysed in 190 µl water followed by a further 20-fold dilution in PBS. A 10 µl fraction was mixed with equal parts trypan blue and loaded on a hemocytometer. Cells were visualized at a magnification of 40× using a LabPro light microscope and totals counted and recorded. Cells are expressed as total cells×10$^8$ per ml of blood. Inhibition of this effect by select compounds is determined statistically using Graphpad prism.

In the 2 hr study, intravenous (IV) DK-PGD$_2$ increased the number of peripheral blood leukocytes, mainly lymphocytes, which likely reflects recruitment from bone marrow. This response was dose-dependently reduced by oral Compound 2 resulting in 21%, 59%, 62% and 80% inhibition at doses of 0.1 mg/kg, 1 mg/kg, 10 mg/kg and 30 mg/kg, respectively. Significant inhibition was achieved in the 1 mg/kg, 10 mg/kg and 30 mg/kg dose groups (p<0.05). Plasma concentrations taken 2.5 hours following oral Compound 2 were 22 nM±3, 61 nM±29, 222 nM±98 and 727 nM±313 in the 0.1 mg/kg, 1 mg/kg, 10 mg/kg and 30 mg/kg dose groups, respectively. Based on these results the ED$_{50}$ is calculated to be 0.85 mg/kg with an associated EC$_{50}$ of 55 nM.

In the 18 hr study, a significant increase in peripheral blood leukocytes was also observed following IV DK-PGD$_2$ challenge. This response was dose-dependently reduced by oral Compound 2 administered 18 hr prior to DK-PGD2 resulting in 0%, 29%, 50% and 77% inhibition of peripheral blood leukocyte numbers at doses of 1 mg/kg, 10 mg/kg, 30 mg/kg and 100 mg/kg, respectively. Significant inhibition was achieved in the 30 mg/kg and 100 mg/kg dose groups (p<0.05) with a calculated ED50 of 30 mg/kg. The concentrations of Compound 1 in plasma recovered 18.5 hr following oral doses of Compound 2 were below the lower limit of quantitation of 40 nM for all animals in the 0.1 mg/kg, 1 mg/kg, and 10 mg/kg dose groups. The observed EC$_{50}$ is <40 nM.

In radioligand membrane binding experiments using cells expressing the guinea pig DP$_2$ receptor, Compound 1 has an IC$_{50}$ of 22.9 nM in the presence of 0.2% guinea pig serum albumin. In the guinea pig whole blood ESC assay, Compound 1 has an IC$_{50}$ of 21.5 nM. Based on the study results, the in vitro and in vivo potencies of Compound 1 are in good agreement suggesting that in vitro binding and/or ESC is a good predictor of the plasma concentration needed to achieve functional activity in an in vivo setting.

In the guinea pig leukocytosis model, the EC$_{50}$s for inhibition of leukocyte emigration from bone marrow or tissue to blood correlated well with the IC$_{50-90}$ range for inhibition of ESC in guinea pig blood (~22-54 nM). These data suggest that therapeutic effects in asthmatics will be achieved with trough concentrations of Compound 1 at the IC$_{50-90}$ range for inhibition of human ESC.

Example 28

Guinea Pig Allergic Asthma Model

Compound 2 was evaluated in a guinea pig OVA model in order to determine efficacy in a setting of allergen-induced asthma. Aerosolized OVA challenge to OVA-primed guinea pigs causes a significant influx of cells into the bronchoalveolar lavage fluid taken 24 hours after challenge. This increase is primarily from influx of eosinophils and neutrophils with a small proportion from macrophages. Compound 2 at 3 mg/kg and 30 mg/kg b.i.d. by mouth (PO) dose-dependently reduced total cellular influx including eosinophils and neutrophils. In the guinea pig allergic asthma model, Compound 1 exhibited anti-inflammatory activity in the lungs.

Example 31

Phase I Study

This is a phase 1, Single-Center, Double-Blind Study of Compound 2 in healthy volunteers.

Objective:

To assess: (1) the safety and tolerability of single and multiple doses of Compound 2 following oral administration; and (2) the pharmacokinetics (PK) of Compound 2 after single and multiple doses; and (3) the effects of the pharmacodynamic (PD) responses in healthy subjects to Compound 2 as measured by a PGD2-induced eosinophil shape change assay (ESC).

The single dose ascending dose (SAD) study will include 5 cohorts with 8 subjects each, 6 receiving the active treatment and 2 receiving the placebo. The SAD study will explore doses of 0.3, 3, 10, 30 mg/day and a fifth dose level to be determined (up to 100 mg/day), administered as an oral solution. Safety monitoring will include: a "how do you feel" (HDYF) question, adverse events reporting, physical examinations, vital signs, ECG's, and a biological assessment (clinical chemistry, hematology and urinalysis). The decision to escalate to the next dose level will be based on the results of medical monitoring. A blinded interim analysis of PK parameters and PD response (ex vivo PGD2-stimulated eosinophil shape change in whole blood, hESC) will be performed after cohort 1 and cohort 2 to confirm dose selection assumptions. Doses may be adjusted based on the occurrence of adverse events. Subjects will be followed for 72 hours after dose administration.

The multiple ascending dose (MAD) study will include 4 cohorts with 8 subjects each, 6 receiving active and 2 receiving placebo. Three cohorts will evaluate doses of 3, 10, 30 mg/day, respectively. The dose level of the fourth cohort is 300 mg/day. Safety monitoring will include: a "how do you feel" (HDYF) question, adverse events reporting, physical examinations, vital signs, ECG's, and a biological assessment (clinical chemistry, hematology and urinalysis). Dose progression will be based on the clinical safety profile of the prior cohort. Subjects will be followed for 72 hours after final dose administration.

Procedure Evaluate Effects of Compound 1 on Ex Vivo PGD$_2$-Induced Blood Eosinophil Shape Change (ESC)

Pre dose blood is drawn and challenged with PGD$_2$ to determine baseline shape change as described above in Example 25. At varying times after dosing blood is drawn for both pharmacokinetic analyses of drug concentration in blood, and also for PGD$_2$ challenge and eosinophil shape change determination. The extent of receptor blockage is determined from the relationship between drug blood concentration and percentage inhibition of eosinophil shape change.

The plasma concentrations of Compound 1 are determined by LC-MS/MS, giving a detection limit of 0.25 ng*mL$^{-1}$.

Pharmacokinetic measurements of Compound 2 includes measurement of the protonated form (Compound 1).

Results

The PK and PD effects of Compound 2 after single and multiple doses are present in FIGS. 1 to 4 and in Tables 13 and 14. FIG. 1 illustrates the ex vivo PGD$_2$-stimulated eosinophil shape change in whole blood after single dose administration of oral solutions of Compound 2 to humans. FIG. 2 illustrates the ex vivo PGD$_2$-stimulated eosinophil shape change in whole blood after multiple dose administration of oral solutions of Compound 2 to humans. FIG. 3 and Table 13 illustrates the plasma concentrations of Compound 1 after single dose administration of oral solutions of Compound 2 to humans. FIG. 4 and Table 14 illustrates the plasma concentrations of Compound 1 after multiple dose administration of oral solutions of Compound 2 to humans.

TABLE 13

Pharmacokinetic parameters of Compound 1 after a single ascending dose.

| Cohort | Dose (mg) | $t_{1/2}$ (hr) | AUC$_{0-24}$(hr*ng*mL$^{-1}$) | C$_{max}$ (ng/mL) |
|---|---|---|---|---|
| 1 | 0.3 | NC | NC | NC |
| 2 | 3 | NC | NC | NC |
| 3 | 10 | NC | NC | NC |
| 4 | 30 | 6.6 | 24.1 | 11.2 |
| 5 | 100 | 8.1 | 118.3 | 81.0 |
| 6 | 300 | 7.0 | 1419.6 | 1398.3 |

Data are average of 6 subjects;
NC—not calculated

TABLE 14

Pharmacokinetic parameters of Compound 1 on days 1 and 7 after multiple dose administration.

| Cohort | Dose (mg) | $t_{1/2}$ (hr) | AUC$_{0-24}$(hr*ng*mL$^{-1}$) | C$_{max}$ (ng/mL) |
|---|---|---|---|---|
| 2—Day 1 | 30 | 10.3 | 32.3 | 16.0 |
| 2—Day 7 | 30 | 11.0 | 44.5 | 15.8 |

The foregoing clinical trial has shown that Compound 1, after single ascending doses, has a terminal half-life value of 6.6-11.0 hr, and an AUC and C$_{max}$ values that increased with increasing dose (Table 13). After 7 days of administration of Compound 1, the terminal half-life, AUC and C$_{max}$ values remain relatively unchanged (Table 14).

The foregoing clinical trial has shown that Compound 1, or a pharmaceutically acceptable salt thereof (e.g. Compound 2), provides a dose dependent pharmacodynamic response as measured by the inhibition of the PGD$_2$-induced eosinophil shape change (ESC). A 80-100% inhibition of the PGD$_2$-induced eosinophil shape change assay (ESC) at C$_{max}$ at doses equal to or greater than 30 mg was observed. A 75-90% inhibition of the PGD$_2$-induced eosinophil shape change assay (ESC) at 24 hours was observed for the 100 mg dose.

Inhibition of the DP2 receptor in humans with prostaglandin D$_2$-dependent or prostaglandin D$_2$-mediated conditions or diseases provides benefit in the condition or disease. Compound 1, or a pharmaceutically acceptable salt thereof (e.g. Compound 2) is useful in the treatment or prevention of prostaglandin D$_2$-dependent or prostaglandin D$_2$-mediated conditions or diseases.

Study 2: Clinical Trial Evaluating Effect of Compound 1 on Mild to Moderate Asthma In this randomized, parallel, double-blind, placebo-controlled study in individuals with childhood onset, atopic, mild to moderate asthma the control of asthma (Asthma Control Questionnaire) and reduction of asthma symptoms is determined following 4 weeks treatment, once daily with Compound 2. One hundred subjects (50 active, 50 placebo) are used. Subjects are dosed once daily for 4 weeks with either placebo or an amount of Compound 2 that results in complete DP2 receptor block in an ex-vivo PGD$_2$-induced blood eosinophil shape change pharmacodynamic study as described above. After 4 weeks, subjects are evaluated for asthma control using the Asthma Control Questionnaire and for changes in asthma symptoms, exacerbations, Forced Expiratory Volume (FEV), Peak Expiratory Flow Rate (PEFR), Beta-2 agonist use. In addition, changes in serum IgE and ECP (eosinophil cationic protein) concentrations and sputum inflammatory cell differentials, Th2 cytokines and ECP are determined for treated and placebo.

Study 3—Vienna Challenge Chamber Study

Study design: The study is a randomised, double blind, placebo controlled, two way crossover evaluation of compound of Formula (I), given orally for eight days. There is a screening period of one week and a washout period of three weeks between the two treatment periods.

There is a follow up one week after the last dose of study drug. The group of patients who receive the study drug for the first treatment period and placebo for the second are designated group A, while the group of patients who receive placebo for the first treatment period and the study drug for the second treatment period are designated group B.

Treatment plan and methods: The subjects undergo a complete screening assessment to determine a baseline response to allergens. This screening assessment takes place one week prior to the start of dosing.

Subjects commence dosing with compound of Formula (I) or placebo on Day 1 of each treatment period of the study. Adverse events, total nasal symptom score and concomitant medications are noted.

Subjects report back to the clinic on Day 2 of each treatment period for a 6 hour allergen challenge. The following measurements are obtained:

Total nasal symptom score (TNSS) (obstruction, rhinorrhoea, itch, sneeze) with each symptom scored on a categorical scale from 0 to 3 pre-challenge, every 15 mins from 0 to 6 h post-start of challenge Eye symptom score (watery eyes, itchy eyes, red eyes) with each symptom scored on a categorical scale from 0 to 3 pre-challenge, every 15 mins from 0 to 6 h post-start of challenge Other symptoms (cough, itchy throat, itchy ears) with each symptom scored on a categorical scale from 0 to 3 pre-challenge and every 15 mins from 0 to 6 h post-start of challenge Subjects report back to the clinic on Day 8 of each treatment period for a 6 hour allergen challenge and the measurements obtained on Day 2 are repeated.

A final follow-up visit is conducted one week after the last dose of test article in Treatment Period 2.

The examples and embodiments described herein are illustrative and various modifications or changes suggested to persons skilled in the art are to be included within this disclosure. As will be appreciated by those skilled in the art, the specific components listed in the above examples may be replaced with other functionally equivalent components, e.g., diluents, binders, lubricants, fillers, and the like.

What is claimed is:

1. A pharmaceutically acceptable salt of [2'-(3-benzyl-1-ethyl-ureidomethyl)-6-methoxy-4'-trifluoromethyl-biphenyl-3-yl]-acetic acid (Compound 1), wherein the pharmaceutically acceptable salt is a calcium salt, potassium salt, sodium salt, ammonium salt, L-arginine salt, or a N-methyl-D-glucamine salt.

2. The pharmaceutically acceptable salt of claim 1, wherein the pharmaceutically acceptable salt has the structure of Compound 2:

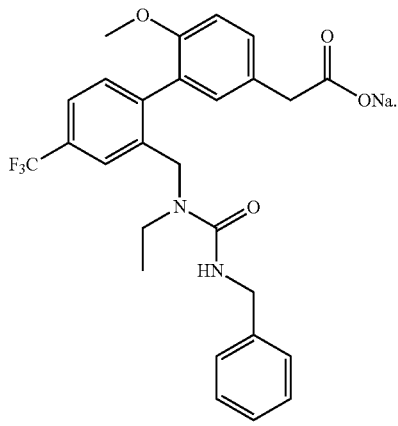

(Compound 2)

3. The pharmaceutically acceptable salt of claim 2, wherein Compound 2 is amorphous.

4. The pharmaceutically acceptable salt of claim 2, wherein the Compound 2 was obtained from a solution containing heptane and ethanol.

5. A pharmaceutical composition comprising:
   a. [2'-(3-benzyl-1-ethyl-ureidomethyl)-6-methoxy-4'-trifluoromethyl-biphenyl-3-yl]-acetic acid (Compound 1) or a pharmaceutically acceptable salt of Compound 1; and
   b. at least one pharmaceutically acceptable excipient.

6. The pharmaceutical composition of claim 5, wherein the pharmaceutical composition comprises [2'-(3-benzyl-1-ethyl-ureidomethyl)-6-methoxy-4'-trifluoromethyl-biphenyl-3-yl]-acetic acid, sodium salt (Compound 2).

7. The pharmaceutical composition of claim 6, wherein Compound 2 is greater than 96% pure.

8. The pharmaceutical composition of claim 6, wherein the pharmaceutical composition is in a form suitable for oral administration to a mammal.

9. The pharmaceutical composition of claim 8, wherein the pharmaceutical composition is in the form of a pill, capsule, tablet, aqueous solution, aqueous suspension, non-aqueous solution, or non-aqueous suspension.

10. The pharmaceutical composition of claim 9, wherein a single dose of the pharmaceutical composition comprises about 0.3 mg to about 600 mg of Compound 2.

11. The pharmaceutical composition of claim 9, wherein a single dose of the pharmaceutical composition when administered to a healthy adult human subject in the fasted state provides:
   80-100% inhibition of ex vivo $PGD_2$-stimulated eosinophil shape change in whole blood at $C_{max}$;
   about 25-100% inhibition of ex vivo $PGD_2$-stimulated eosinophil shape change in whole blood after about 24 hours following administration; or
   about 30-70% inhibition of ex vivo $PGD_2$-stimulated eosinophil shape change in whole blood after about 24 hours following administration.

12. The pharmaceutical composition according to claim 9, wherein the pharmaceutical composition is in the form of a tablet, pill, or capsule and the pharmaceutical composition comprises about 1 mg, about 3 mg, about 10 mg, about 30 mg, about 60 mg, about 100 mg, about 200 mg, about 250 mg, about 300 mg or about 600 mg of Compound 2.

13. The pharmaceutical composition of claim 5, wherein the pharmaceutical composition provides at least one metabolite of [2'-(3-benzyl-1-ethyl-ureidomethyl)-6-methoxy-4'-trifluoromethyl-biphenyl-3-yl]-acetic acid (Compound 1) after administration to a mammal.

* * * * *